(12) United States Patent
Nishitani et al.

(10) Patent No.: US 6,214,818 B1
(45) Date of Patent: Apr. 10, 2001

(54) CEPHEM COMPOUNDS AND PHARMACEUTICAL COMPOSITIONS CONTAINING THE SAME

(75) Inventors: Yasuhiro Nishitani, Osaka; Koji Ishikura, Nara, both of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/147,074

(22) PCT Filed: Apr. 4, 1997

(86) PCT No.: PCT/JP97/01161

§ 371 Date: Oct. 1, 1998

§ 102(e) Date: Oct. 1, 1998

(87) PCT Pub. No.: WO97/37996

PCT Pub. Date: Oct. 16, 1997

(30) Foreign Application Priority Data

Apr. 4, 1996 (JP) .................................................. 8-082531

(51) Int. Cl.$^7$ ..................... C07D 501/46; C07D 501/38; A61K 31/545; A61K 31/546; A61D 31/04
(52) U.S. Cl. ..................... 514/203; 540/224; 540/225; 546/274.7; 546/275.4; 546/276.4; 546/279.1; 546/280.4; 546/328; 546/341
(58) Field of Search ..................... 540/224, 225; 514/203

(56) References Cited

FOREIGN PATENT DOCUMENTS

| | | | |
|---|---|---|---|
| 57-192394 | * | 11/1982 | (JP) . |
| 58-162592 | * | 9/1983 | (JP) . |
| 60-64988 | * | 4/1985 | (JP) . |
| 60-237090 | * | 11/1985 | (JP) . |
| 62-53993 | * | 3/1987 | (JP) . |
| 62-158290 | * | 7/1987 | (JP) . |
| 62-158291 | * | 7/1987 | (JP) . |
| 4-59730 | * | 2/1992 | (JP) . |
| 5-217239 | * | 10/1993 | (JP) . |
| 7-041485 | * | 2/1995 | (JP) . |

OTHER PUBLICATIONS

"Organic Chemistry, 5th Edition" Morrison and Boyd, p. 832, 1987.*
Derwent Abstract for JP 62–158290, Jul. 1987.*
Derwent Abstract for JP 4–59730, Feb. 1992.*
Derwent Abstract for JP 60–64988, Apr. 1985.*
Derwent Abstract for JP 5–217239, Oct. 1993.*
Derwent Abstract for JP 7–041485, Feb. 1995.*
Derwent Abstract for JP 60–237090, Nov. 1985.*

* cited by examiner

*Primary Examiner*—Mark Berch
(74) *Attorney, Agent, or Firm*—Foley & Lardner

(57) ABSTRACT

A cephem compound, wherein the cephem ring has a substituent at the 3-position, which substituent is shown by the formula II, wherein Het is a mono- or polycyclic heterocyclic group comprising one or more hetero atoms selected from the group consisting of N, O and S which may be the same or different from each other; $R^1$ is hydrogen, an optionally substituted lower alkyl or an optionally substituted lower alkenyl; A is an optionally substituted lower alkylene, an optionally substituted lower alkenylene or a single bond; B is an optionally substituted imino or a single bond; or A and B taken together may form a single bond; and D is a single bond or a group of the formula (a):

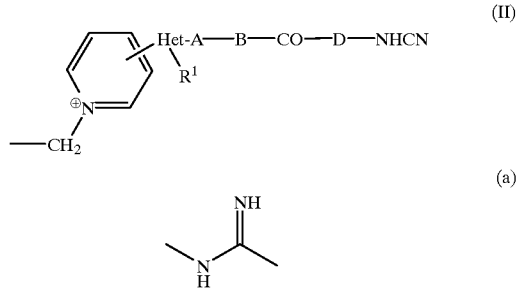

The cephem compounds of the present invention are useful as antibiotic agents.

7 Claims, No Drawings

CEPHEM COMPOUNDS AND PHARMACEUTICAL COMPOSITIONS CONTAINING THE SAME

This application has been filed under 35 U.S.C. § 371 from PCT/JP97/01161, filed Apr. 4, 1997.

TECHNICAL FIELD

The present invention relates to novel cephem compounds, a process for preparing the same, intermediates therefor, and pharmaceutical compositions containing the compounds.

BACKGROUND ART

Compounds having an optionally substituted pyridiniomethyl group at the 3-position of the cephem ring have been disclosed in patent applications such as Japanese Patent Publication (KOKAI) 60-237090 (WO 8505106, EP 160969A2), Japanese Patent Publication (KOKOKU) 1-44190 and also Japanese Patent Publication (KOKOKU) 6-70068 (EP 64740B1, U.S. Pat. No. 5,071,979), Japanese Patent Publication (KOKOKU) 2-44476 (EP 159011B1, U.S. Pat. No. 4,833,242), etc. However, there have not been reported compounds wherein a pyridinium ring is substituted with a heterocyclic group having a substituent of the formula —CONHCN or its analogues.

Although a huge number of antibiotics have been marketed so far, the development and characterization of compounds with higher antibiotic activity have been continuously demanded so as to cope with the appearance of multiple drug resistant bacteria and to provide for the diversification of therapy forms. In particular, it has been demanded to develop cephem compounds of broad spectrum which show a long blood half-life and have an excellent in vivo dynamics such as transfer to a tissue.

DISCLOSURE OF INVENTION

The present inventors have intensively studied with a purpose for developing novel cephem compounds with superior characteristics and found that cephem compounds wherein the cephem ring has a pyridiniomethyl group at the 3-position, and wherein the pyridinium ring is substituted with a heterocyclic group having a substituent -CONHCN or an analogue thereof have an excellent in vivo dynamics properties.

Thus, the present invention provides a cephem compound wherein the cephem ring has a substituent at the 3-position, which substituent is shown by the formula II:

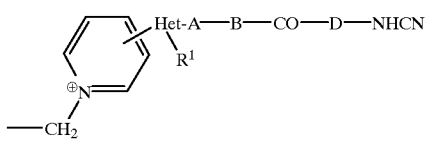

wherein
Het is a mono- or polycyclic heterocyclic group comprising one or more hetero atoms selected from the group consisting of N, O and S which may be the same or different from each other; $R^1$ is hydrogen, an optionally substituted lower alkyl or an optionally substituted lower alkenyl; A is an optionally substituted lower alkylene, an optionally substituted lower alkenylene or a single bond; B is an optionally substituted imino or a single bond; and D is a single bond or a group of the formula:

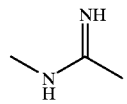

or a salt or a hydrate thereof. The above-mentioned cephem compounds, salts or hydrates may be hereinafter referred to as the compound of the present invention.

The compound of the present invention is preferably represented by the formula I:

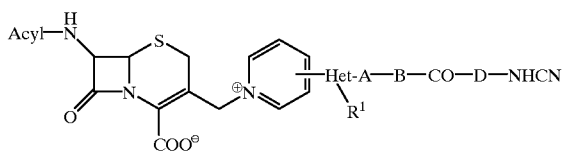

wherein Acyl is an acyl, and Het, $R^1$, A, B and D are as defined above, or an ester, a salt, or a hydrate thereof.

Acyl in the formula I is preferably a group of the formula III:

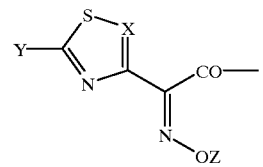

wherein X is CH or N; Y is an optionally protected amino; and Z is an optionally substituted hydrocarbon group.

Het in the formula I or II is preferably a 5- or 6-membered trivalent hetero cyclic group comprising one to four hetero atoms selected from the group consisting of N, O and S which may be the same or different from each other, and, more preferably, a pyrrolyl group of the formula IV:

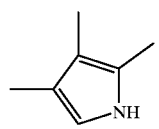

Further, A in the formula I or II is preferably a single bond or a vinyl group; B is a single bond; and D is a single bond.

Example of preferable compounds of the formula I include those wherein Acyl is a group of the formula III:

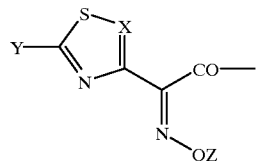

III (wherein X is CH or N, Y is an optionally protected amino and Z is hydrogen or an optionally substituted hydrocarbon group); Het is a 5- or 6-membered hetero cyclic group comprising one to four hetero atoms selected from the group consisting of N, O and S which may be the same or different from each other; A is a single bond or a vinyl group; B is a single bond; and D is a single bond, or an ester, a salt, or a hydrate thereof.

Terms herein used are defined below.

Throughout the present specification, the term "cephem compound" refers to a class of compounds having a double bond between the 3- and 4-positions of the cepham ring and named according to the nomenclature shown under the heading "cephem" in *The Journal of the American Chemical Society*, 84, 3400 (1962). The present invention encompasses compounds of the formula I pharmaceutically acceptable esters, salts, or hydrates thereof (i.e., esters of Compound I, salts of Compound I, salts of an ester of Compound I, or hydrates thereof). The signal "−" in —COO− at the 4-position of a compound of the formula I indicates that a carboxylate anion forms an intramolecular salt by making a pair with the pyridinium cation on the substituent at the 3-position. When the carboxyl group is not ionized, the pyridinium cation can form a salt with an anion or a counter ion on a side-chain. The present invention encompasses all of these embodiments. The "S" at the 1-position of the cephem ring may be oxidized.

The term "mono- or polycyclic heterocyclic group" in the definition of "Het" includes the both aromatic and non-aromatic mono- or polycyclic heterocyclic groups, which is bound to the adjacent three groups. In the case of a mono-cyclic heterocyclic group, examples of a preferred aromatic heterocyclic group include 5- to 6-membered cyclic groups such as furan, thiophene, tetrazole, pyrrole, pyrazole, imidazole, oxazole, thiazole, pyridine, oxazine and triazine. Examples of a preferred non-aromatic heterocyclic group include 5- to 7-membered groups such as pyrrolidine, thiazolidine, oxazolidine, imidazolidine, thiazoline, oxazoline, imidazoline, piperidine, piperazine, morpholine, thiomorpholine, oxadiazoline, and dioxane. Among them, a monocyclic heterocyclic group comprising one or two hetero atoms selected from N and S is more preferable, and pyrrole is most preferred.

Preferred examples of polycyclic heterocyclic groups include those wherein benzene ring, pyridine ring, pyrazine ring, pyridazine ring, pyrimidine ring, or the like, is condensed to an above-mentioned monocyclic aromatic heterocyclic group, such as benzothiophene, indole, benzothiazole, benzofuran, and benzimidazole. Those wherein Het is bound to the 4-position of pyridinium ring are preferred.

The term "lower alkyl" in the definition of "$R^1$" refers to a straight or branched $C_{1-6}$alkyl groups, such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, and the like. $C_{1-4}$alkyl group such as methyl, ethyl, propyl, isopropyl, butyl, isobutyl, and the like, are preferred. The lower alkyl group may be substituted by a substituent(s) selected from, for example, lower alkenyl group (e.g., $C_{2-6}$alkenyl group such as vinyl, butenyl, propenyl, etc.); cycloalkyl group (e.g., $C_{3-7}$cycloalkyl group such as cyclopropyl, cyclobutyl, cyclopentyl, cyclohexyl, cycloheptyl, etc.); aryl group (e.g., $C_{6-10}$aryl group such as phenyl, naphthyl, etc., which aryl group may be further substituted by hydroxy, $C_{1-4}$alkyl such as methyl or ethyl, or $C_{1-4}$alkoxy such as methoxy or ethoxy); aromatic heterocyclic group (e.g., 5- or 6-membered aromatic heterocyclic group comprising 1 to 4 hetero atoms selected from N, O, S, and the like, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4- thiadiazolyl, 1,2,3-triazolyl, 1,2,4-triazolyl, tetrazolyl, pyridyl, pyridazinyl, pyrimidinyl, pyrazinyl, triazinyl; bi- or tricyclic aromatic condensed heterocyclic group comprising 1 to 5 hetero atoms selected from N, O, S, and the like, which is formed by condensing one or two 5- or 6-membered aromatic heterocyclic groups comprising 1 to 4 hetero atoms selected from N, O, S, and the like or one or two benzene rings, such as benzofuranyl, isobenzofuranyl, benzo[b]thienyl, indolyl, isoindolyl, 1H-inzdazolyl, bonzimidazolyl, benzoxazolyl, 1,2-benzisoxazolyl, benzothiazolyl, 1 ,2-benzisothiazolyl, 1H-benzotriazolyl, quinolyl, isoquinolyl, cinnolinyl, quinazolinyl, quinoxalinyl, phthaladinyl, naphthylidinyl, purinyl, putelidinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolydinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl); non-aromatic heterocyclic group (e.g., 4- or 6-membered non-aromatic heterocyclic group comprising 1 to 3 hetero atoms selected from N, O, S, and the like, such as oxiranyl, azetidinyl, oxetanyl, thiethanyl, pyrrolidinyl, tetrahydrofuryl, thiolanyl, piperidyl, tetrahydropyranyl, morpholinyl, thiomorpholinyl, piperadinyl, and the like); amino group; mono- or di-lower alkyl amino group (e.g., mono- or di$C_{1-6}$alkylamino group such as methylamino, ethylamino, dimethylamino, and the like); tri-lower alkylammonium group (e.g., tri$C_{1-6}$alkylammonium group such as trimethylammonium, triethylammonium, tripropylammonium, and the like); amidino group; acyl group (e.g., $C_{1-6}$alkanoyl group such as formyl, acetyl, propionyl, and the like); carbamoyl group; mono- or di-lower alkylcarbamoyl group (e.g., mono- or di$C_{1-6}$alkylcarbamoyl group such as methylcarbamoyl, ethylcarbamoyl, dimethylcarbamoyl, and the like); sulfamoyl group; mono- or di-lower alkyl sulfamoyl group (e.g., mono- or di$C_{1-6}$alkylsulfamoyl group such as methylsulfamoyl, ethylsulfamoyl, dimethylsulfamoyl, and the like); carboxyl group; lower alkoxycarbonyl group (e.g., $C_{1-6}$alkoxycarbonyl group such as methoxycarbonyl, ethoxycarbonyl, and the like); hydroxyl group; lower alkoxy group (e.g., $C_{1-6}$alkoxy group such as methoxy, ethoxy, and the like); lower alkenyloxy group (e.g., $C_{2-6}$alkenyloxy group such as allyloxy, 2-buthenyloxy, and the like); cycloalkyloxy group (e.g., $C_{3-7}$cycloalkyloxy group such as cyclopropyloxy, cyclobutyloxy, cyclopentyloxy, cyclohexyloxy, cycloheptyloxy, and the like); aralkyloxy group (e.g., $C_{7-10}$aralkyloxy group such as benzyloxy, phenethyloxy, and the like); aryloxy group (e.g., $C_{6-10}$aryloxy group such as phenoxy, naphthyloxy, and the like); mercapto group; lower alkylthio group (e.g., $C_{1-6}$alkylthio group such as methylthio, ethylthio, and the like); aralkylthio group (e.g., $C_{7-10}$aralkylthio group such as benzylthio, phenethylthio, and the like); arylthio group (e.g., $C_{6-10}$arylthio group such as phenylthio, naphthylthio, and the like); sulfo group; cyano group; azide group; nitro group; nitroso group; halogen (e.g., fluorine, chlorine, iodine, and the like). The number of substituent is preferably 1 to 3 and when there are more than one substituents, they may be the same or different from each other.

The term "lower alkenyl" refers to a straight or branched $C_{2-6}$alkenyl group such as allyl, propenyl, butenyl, pentenyl, and the like, and allyl is preferred. The lower alkenyl group may be substituted by a substituent(s) similar to those mentioned above for lower alkyl group.

The term "lower-alkylene" in the definition of "A" refers to a group derived from the above-mentioned lower alkyl groups, for example, methylene, ethylene, butylene, propylene, pentylene, and the like, and methylene and ethylene are preferred. The lower alkylene group can be substituted by a substituent(s) similar to those mentioned above for lower alkyl group.

The term "lower alkenylene" refers to a group derived from the above-mentioned lower alkenyl groups, for example, vinylene, butenylene, propenylene, and the like, and vinylene is preferred. The lower alkenylene group can be substituted by a substituent(s) similar to those mentioned above for lower alkyl group.

The "acyl group" represented by Acyl refers to an acyl group known as a substituent for the 6-amino group of penicillin derivatives as well as the 7-amino group of cephem compounds. Examples of such acyl groups include those derived from organic carboxylic acids such as formyl group; alkylcarbonyl group (alkanoyl group), preferably, $(C_1-C_6)$alkyl-carbonyl group (e.g., acetyl, propionyl, butyryl, isobutyryl, valeryl, isovaleryl, pivaloyl, hexanoyl, and the like); $(C_3-C_5)$alkenoyl group (e.g., acryloyl, chrotonoyl, maleoyl, and the like); $(C_3-C_{10})$cycloalkyl-carbonyl group (e.g., cyclopropylcarbonyl, cyclobutylcarbonyl, cyclopentylcarbonyl, cyclohexylcarbonyl, cycloheptylcarbonyl, adamantylcarbonyl, and the like); $(C_5-C_6)$cycloalkenyl-carbonyl group (e.g., cyclopentenylcarbonyl, cyclopentadienylcarbonyl, cyclohexenylcarbonyl, cyclohexadienylcarbonyl, and the like); arylcarbonyl group (aroyl group), preferably, $(C_6-C_{14})$aryl-carbonyl group (e.g., benzoyl, 1- or 2-naphthoyl, and the like); aralkyl carbonyl group, preferably, $(C_7-C_{19})$aralkyl-carbonyl group (e.g., phenylacetyl, phenylpropionyl, α,α,α-triphenylacetyl, 2-phenetylcarbonyl, 1- or 2-naphthylmethylcarbonyl, benzhydrylcarbonyl, and the like); 5- or 6-membered aromatic heterocyclic carbonyl group (e.g., 2- or 3-thenoyl, 2- or 3-furoyl, nicotinoyl, isonicotinoyl, 4- or 5-thiazolylcarbonyl, 1,2,4-thiadiazol-3- or 1,2,4-thiadiazol-5-yl-carbonyl, and the like); 5- or 6-membered aromatic heterocyclic acetyl group (e.g., 2- or 3-thienylacetyl, 2- or 3-furylacetyl, 4-thiazolylacetyl, 1,2,4-thiadiazol-3-yl-acetyl, 1-tetrazolylacetyl, and the like); alkoxycarbonyl group, preferably, $(C_1-C_6)$alkoxy-carbonyl group (e.g., methoxycarbonyl, ethoxycarbonyl, propoxycarbonyl, isopropoxycarbonyl, butoxycarbonyl, isobutoxycarbonyl, tert-butoxycarbonyl, and the like); aryloxycarbonyl group, preferably, $(C_6-C_{14})$aryloxy-carbonyl group (e.g., phenoxycarbonyl, 1- or 2-naphtoxycarbonyl, and the like); aralkyloxycarbonyl group, preferably, $(C_7-C_{19})$ aralkyloxycarbonyl group (e.g;, benzyloxycarborryl, and the like); aminoalkylcarbonyl group (e.g., amino $C_{1-6}$alkyl-carbonyl group such as glycyl, aranyl, valyl, leucyl, isoleucyl, seryl, threonyl, cysteinyl, cystynyl, methionyl, asparaginyl, glutamyl, lysyl, arginyl, phenylglycyl, phenylalanyl, tyrosyl, histidyl, tryptophanyl, prolyl, 2-aminoethylcarbonyl, 3-aminopropylcarbonyl, and the like); monoalkylaminoalkylcarbonyl group (e.g., mono$C_{1-6}$alkylamino-$C_{1-6}$alkyl-carbonyl group such as methylaminomethylcarbonyl, 2-ethylaminoethylcarbonyl, and the like); and dialkylaminoalkylcarbonyl group (e.g., di$C_{1-6}$alkylamino-$C_{1-6}$alkyl-carbonyl group such as dimethylaminomethylcarbonyl, diethylaminomethylcarbonyl, and the like).

These acyl group may be substituted by one to three substituents selected from amino, nitro, halogen (e.g., fluorine, chlorine, bromine, and the like), hydroxy, oxo, carbamoyl group, $(C_1-C_4)$alkyl group (e.g., methyl, ethyl, propyl, isopropyl, butyl, and the like), $(C_1-C_4)$alkoxy group (e.g., methoxy, ethoxy, propoxy, butoxy, and the like), optionally esterified carboxyl group (e.g., $(C_1-C_6)$ alkoxycarbonyl group such as methoxycarbonyl, ethoxycarbonyl, and the like), $(C_1-C_4)$alkoxyimino group which is optionally substituted by carboxyl or halogen (e.g., methoxyimino, ethoxyimino, carboxymethoxyimino, 1-carboxy-1-mehylethoxyimino, fluoromethoxyimino, fluoroethoxyimino, and the like), hydroxyimino group, and 4-ethyl-2,3-dioxopiperadinocarbonylamino group.

The heterocyclic group in the 5- or 6-membered aromatic heterocyclic carbonyl group and 5- or 6-membered aromatic heterocyclic acetyl group as defined above refers to an aromatic heterocyclic group comprising one to four hetero atoms selected from the group consisting of optionally oxidized nitrogen atom, oxygen atom, optionally mono- or dioxidized sulfur atom, and the like, and examples other than those set forth above include pyrrole, imidazole, pyrazole, pyrimidine, pyrazine, pyridazine, indole, isothiazole, oxazole, isoxazole, and triazole.

Preferred examples of Acyl include those shown by the formula (III) wherein X is CH or N; Y is an optionally protected amino; and Z is hydrogen or an optionally substituted hydrocarbon group.

Examples of amino-protecting groups in the definition of Y include an appropriate group used in the field of β-lactam- and peptide chemistry. Preferred amino-protecting group includes formyl, chloroacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, and trityl.

Examples of a hydrocarbon group in the definition of "Z" include lower alkyl, lower alkenyl, lower alkynyl, cycloalkyl, aralkyl, di- or triaryl-methyl and aryl. The lower alkyl group is a straight or branched alkyl group of, preferably, 1 to 6 carbon atoms, such as methyl, ethyl, n-propyl, isopropyl, n-butyl, isobutyl, sec-butyl, tert-butyl, n-pentyl, n-hexyl, and the like. The lower alkenyl group is a straight or branched alkenyl group of, preferably, 2 to 6 carbon atoms, such as allyl, propenyl, butenyl, pentenyl, and the like. The lower alkynyl group is a straight or branched alkynyl group of, preferably, 2 to 6 carbon atoms, such as propynyl, butynyl, pentynyl, and the like. The cycloalkyl group is preferably a cycloalkyl group of 3 to 6 carbon atoms, such as cyclopropyl, cyclobutyl, cyclopentyl, cyclohexyl, and the like. The aralkyl group is preferably a group of 7 to 10 carbon atoms, such as benzyl, and the like. The di- or triaryl-methyl group is preferably a di- or tri($C_{6-10}$aryl)-methyl group, such as benzhydryl, di(p-tolyl)methyl, trityl, tri(p-tolyl)methyl, and the like. The aryl group is a group of 6 to 10 carbon atoms, such as phenyl, and the like.

The hydrocarbon group shown by "Z" may be substituted by one to three substituents selected from, for example, carboxyl group; $C_{1-6}$alkoxy-carbonyl group such as methoxycarbonyl, ethoxycarbonyl, and the like; carbamoyl group; $C_{1-6}$alkylthio group such as methylthio, ethylthio, and the like; sulfamoyl group; amino group; hydroxy group; cyano group; carbamoyloxy group; and halogen such as fluorine, chlorine, and the like. Examples of preferred Z include hydrogen, ($C_1$–$C_3$)lower alkyl group and a lower alkyl group substituted by one or 2 substituents selected from halogen and carboxyl group (e.g., fluoromethyl, fluoroethyl, carboxypropyl, etc.)

Ester derivatives of a compound or an intermediate of the present invention are those formed through the esterification of a carboxyl group(s) in the molecule, and are usable as a synthetic intermediate or a non-toxic metabolic ester which is apt to undergo hydrolysis in vivo.

Examples of ester derivatives usable as a synthetic intermediate include optionally substituted $C_{1-6}$alkyl ester, $C_{2-6}$alkenyl ester, $C_{3-10}$cycloalkyl ester, $C_{3-10}$cycloalkyl-$C_{1-6}$alkyl ester, optionally substituted $C_{6-10}$aryl ester, optionally substituted $C_{7-12}$aralkyl ester, $diC_{6-10}$aryl-methyl ester, $triC_{6-10}$aryl-methyl ester, substituted silyl ester, and the like.

Examples of metabolic ester residues include acetoxymethyl group, 1-acetoxyethyl group, 1-acetoxypropyl group; pivaloyloxymethyl group, 1-isopropyloxycarbonyloxyethyl group, 1-cyclohexyloxycarbonyloxyethyl group, phthalidyl group, (2-oxo-5-methyl-1,3-dioxol-4-yl)methyl, and the like.

When the —COO⁻ group at the 4-position of Compound I is esterified, the ester residue can be, for example, a group of the formula VIII:

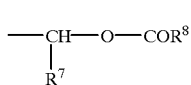

VIII wherein $R^7$ is hydrogen, an alkyl group, a cycloalkyl group or a cycloalkylalkyl group; $R^8$ is hydrogen, an alkyl group, a cycloalkyl group, an alkoxy group, a cycloalkyloxy group, a cycloalkylalkyl group, an alkenyloxy group, or a phenyl group; a phthalidyl group; (2-oxo-5-methyl-1,3-dioxol-4-yl) methyl group; an alkoxyalkyl group; an alkylthioalkyl group; a tert-butyl group; a 2,2,2-trichloroethyl group; a benzyl group; a p-methoxybenzyl group; a p-nitrobenzyl group; a benzhydryl group; a trityl group; a trimethylsilyl group; or an allyl group.

In the above definition, the alkyl group or the alkyl moiety in cycloalkylalkyl group, alkoxyalkyl group and alkylthioalkyl group can be, for example, a straight or branched group of 1 to 6 carbon atoms (e.g., methyl, ethyl, propyl, isopropyl, butyl, 2,2-dimethylpropyl, etc.), and the cycloalkyl group or the cycloalkyl moiety in cycloalkyloxy group or cycloalkylalkyl group can be, for example, a cycloalkyl group of 3 to 7 carbon atoms (e.g., cyclopropyl, cyclobutyl, cyclopentyl, cyclohexyl, cycloheptyl, etc). Examples of alkoxy group or alkoxy moiety in alkoxyalkyl group include a straight or a branched chain alkoxy group of 1 to 10 carbon atoms (e.g., methoxy, ethoxy, propoxy, isopropoxy, butoxy, hexyloxy, decyloxy, etc.) Examples of alkenyloxy group include a straight or a branched chain alkenyloxy group of 2 to 7 carbon atoms (e.g., allyloxy, etc.)

As a salt of the compound of the present invention, pharmaceutically acceptable salts are preferred, such as those formed with an inorganic base, an organic base, an inorganic acid, an organic acid, a basic or acidic amino acid, and intra-molecular salts. Examples of preferred salts formed with an inorganic base include alkali metal salts such as sodium or potassium salts; alkaline-earth metal salts such as calcium or magnesium salts; alminium salts; and ammonium salts. Examples of preferred salts formed with an organic base include those formed with trimethylamine, triethylamine, pyridine, picoline, ethanolamine, diethanolamine, triethanolamine, dicyclohexylamine, N,N'-dibenzylethylenediamine, procaine, 2-phenylethylbenzylamine, trishydroxymethylaminomethane, polyhydroxyalkylamine, N-methylglucosamine, and the like. Examples of preferred salts formed with an inorganic acid include those formed with hydrochloric acid, hydrobromic acid, nitric acid, sulfuric acid, phosphoric acid, and the like. Examples of preferred salts formed with an organic acid include those formed with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Examples of preferred salts formed with basic amino acid include those formed with arginine, lysine, ornithine, histidine, and the like. Examples of preferred salts formed with an acidic amino acid include those formed with aspartic acid, glutamic acid, and the like.

Among the salts, the base-addition salts (i.e., salts with inorganic or organic base, or basic amino acid) are those which can be formed at the 4-carboxyl group of the cephem ring or an acidic group such as carboxyl group, sulfo group, hydroxyl group, or the like, on the side chain, if any. The acid-addition salts (i.e., salts with inorganic or organic acid, or acidic amino acid) means those which can be formed at a basic group such as amino group, monoalkylamino group, dialkylamino group, cycloalkylamino group, arylamino group, aralkylamino group, N-containing heterocyclic group, or the like, of a compound of the present invention, if any. Acid addition salts also include those having a counter ion such as chloride ion, bromide ion, sulfate ion, p-toluenesulfonate ion, methanesulfonate ion, trifluoroacetate ion, or the like, which are formed when an organic or inorganic acid (1 mole) is attached to the site of a compound of the present invention where an intramolecular salt is formed between the 4-carboxylate moiety (COO⁻) and the pyridinium cation on the 3-side chain.

The hydrate of the present invention refers to a mono- or dihydrate. They are obtainable by selecting an appropriate drying method.

The compound of the present invention can be prepared according to a known method in the field of β-lactam. The typical processes are provided below.

[Production Method 1]

A compound of the formula I, or an ester or a salt thereof can be prepared by reacting a cephem compound of the formula V:

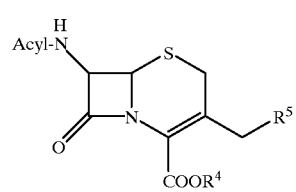

V wherein $R^4$ is a carboxy-protecting group, $R^5$ is a hydroxy group, an acyloxy group, a carbamoyloxy group, a substituted carbamoyloxy group, or a halogen atom, or a salt thereof with a pyridine derivative of the formula VI:

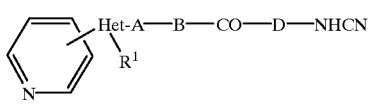

VI wherein $R^1$, A, B, D and Het are as defined above, or a salt thereof, and optionally deprotecting the reaction product.

In the reaction, Compound V or its salt (hereinafter, they may be referred to as Compound V) and a pyridine derivative VI or its salt (hereinafter, they may be referred to as Compound VI) are reacted to give Compound I through the nucleophilic substitution reaction. Compound V can be easily obtained in accordance with a known method such as those described in Japanese Patent Publication (KOKAI) 231684/1985 or Japanese Patent Publication (KOKAI) 149682/1987, or a method equivalent thereto. Compound VI can be prepared in a manner shown in the working examples below.

The nucleophilic substitution of Compound V by Compound VI is normally carried out in a solvent. Solvents useable in the reaction are ethers (dioxane, tetrahydrofuran, diethylether, etc.), esters (ethyl formate, ethyl acetate, n-butyl acetate, etc.), halogenated hydrocarbons (dichloromethane, chloroform, carbon tetrachloride, 1,2-dichloroethane, etc.), hydrocarbons (n-hexane, benzene, toluene, etc.), amides (formamide, N,N-dimethylformamide, etc.), ketones (acetone, methyl ethyl ketone, etc.), nitrites (acetonitrile, propionitrile, etc.), and also dimethyl sulfoxide, sulfolane, hexamethylphosphoramide, and water, which are used alone or in combination as a mixed solvent. Further, alcohols such as methanol, ethanol, n-propanol, isopropanol, ethylene glycol, 2-methoxyethanol, can be used.

When Compound VI is liquid, it can be used in a large excess (e.g., 10 to 200-fold moles) to Compound V so that it can serve as a solvent. In such a case, Compound VI can be used in combination with any one or more solvents above to give a mixed solvent.

When $R^5$ in Compound V is an acyloxy group, a carbamoyloxy group or a substituted carbamoyloxy group, more preferred solvent is water, or a mixed solvent of water and a water-miscible organic solvent. Preferred examples of the organic solvent include acetone, methyl ethyl ketone, acetonitrile, and the like. The amount of Compound VI is normally between about 1 to 5 moles, preferably about 1 to 3 moles, based on 1 mole of Compound V. The reaction is conducted at temperature range of about 10 to 100° C., preferably about 30 to 80° C. The reaction time depends on the kinds of Compound V, compound VI, or the solvent, reaction temperature, or the like, but is normally from about tens minutes to several hours, preferably from about 1 to 5 hours. The reaction is advantageously conducted at the pH range of 2 to 8, preferably about neutral, i.e. pH 5 to 8. This reaction easily proceeds in the presence of 2 to 30 equivalents of iodides or thiocyanates. Examples of such salts include sodium iodide, potassium iodide, sodium thiocyanate, potassium thiocyanate, and the like. The reaction can be allowed to proceed smoothly by adding quaternary ammonium salts having a surface activity action such as trimethylbenzylammonium bromide, triethylbenzylammonium bromide, triethylbenzylammonium hydroxide, and the like, in addition to the above salts.

When $R^5$ in Compound V is a hydroxyl group, the reaction can be effected in the presence of an organophosphorous compound according to the method described, for example, in Japanese Patent Publication (KOKAI) 58-43979 (corresponding to U.S. Pat. Nos. 4,642,365 and 4,801,703).

Preferred solvents usable in the reaction include, for example, the above-mentioned ethers, esters, halogenated hydrocarbons, hydrocarbons, amides, ketones, nitriles and sulfoxides, which are used alone or in combination. Particularly, dichloromethane, acetonitrile, dimethylformamide, dimethyl sulfoxide, a mixed solvent of dimethylformamide and acetonitrile, and a mixed solvent of dichloromethane and acetonitrile would lead to good results. The amount of Compound VI or a salt thereof, and that of the organophosphorous compound is preferably from about 1 to 5 moles and about 1 to 10 moles, more preferably from about 1 to 3 moles and about 1 to 6 moles, respectively, based on 1 mole of Compound V. The reaction is conducted at temperature range of about –80 to 50° C., preferably about –40 to 40° C. The reaction time is normally from about 30 minutes to 48 hours, preferably from about 1 to 24 hours. An organic base can be added in the reaction system. Examples of the organic base include amines such as triethylamine, tri(n-butyl)amine, di(n-butyl)amine, diisobutylamine, dicyclohexylamine, and the like. The amount of the base is preferably about 1 to 5 moles based on 1 mole of Compound V.

When $R^5$ in compound V is a halogen atom (preferably iodine), preferable solvents are the above ethers, esters, halogenated hydrocarbons, hydrocarbons, amides, ketones, nitrites, alcohols, water, sulfoxides, and the like. The amount of Compound VI is normally from about 1 to 5 moles, preferably from about 1 to 3 moles, based on 1 mole of Compound V. The reaction is conducted at temperature range of about 0 to 80° C., preferably about 20 to 60° C. The reaction time is normally from about 30 minutes to 15 hours, preferably from about 1 to 5 hours. The reaction can be facilitated in the presence of a dehydrohalogenating agent. Examples of dehydrohalogenating agent usable in the reaction include deacidifying agents such as inorganic bases (e.g. sodium carbonate, potassium carbonate, calcium carbonate, sodium hydrogencarbonate, etc.), tertiary-amines (e.g. triethylamine, tri(n-propyl)amine, tri(n-butyl)amine, diisopropylethylamine, cyclohexyldimethylamine, pyridine, lutidine, etc.) and alkylene oxides (e.g. propylene oxide, epichlorohydrin, etc.), but Compound VI itself can be used as the dehydrohalogenating agent. In this case, Compound VI is used in the amount of 2 moles or more based on 1 mole of Compound V.

[Production Method 2]

A compound wherein Acyl in the formula I is shown by the formula III can also be produced through the etherification by reacting a hydroxyimino derivative of the formula VII:

VII

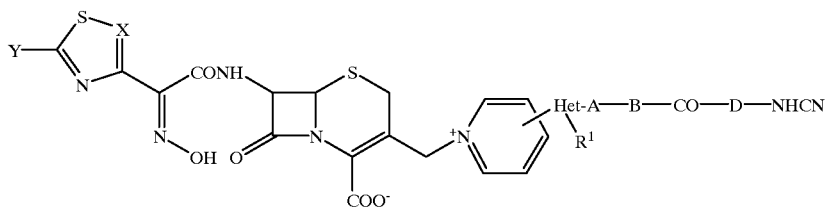

wherein the respective symbols are as defined above, an ester, or a salt thereof with a compound of the formula ZOH (wherein Z is as defined above) or a reactive derivative thereof. The reactive derivatives of ZOH are those capable of replacing a hydrogen atom of the hydroxyimino compound VII with Z and include, for example, a compound of the formula $ZR^6$ (wherein $R^6$ is a leaving group such as a halogen atom, a mono-substituted sulfonyloxy group, etc.). Examples of the mono-substituted sulfonyloxy group include $C_{1-6}$alkylsulfonyloxy group and $C_{6-10}$arylsulfonyloxy group, such as methanesulfonyloxy, ethanesulfonyloxy, benzenesulfonyloxy, p-toluenesulfonyloxy, and the like.

The hydroxyimino compound VII can be synthesized by the method described herein or those known in the art.

The compound ZOH and reactive derivatives thereof can be easily synthesized by a known method, for example, those described in Japanese Patent Publication (KOKAI) Nos. 60-231684 and 62-149682) or analogues thereof.

When using ZOH, the hydroxyimino compound VII is reacted with a compound ZOH by using an appropriate dehydrating agent to synthesize Compound I. Examples of the dehydrating agent used for this purpose include phoshorous oxychloride, thionyl chloride, dialkyl azodicarboxylate (normally used in combination with phosphine), N,N'-dicyclohexylcarbodiimide, and the like. Preferred dehydrating agent is diethyl azocarboxylate in combination with triphenylphosphine. The reaction using diethyl azocarboxylate in combination with triphenylphosphine is normally conducted in an anhydrous solvent. For example, the above-mentioned ethers and hydrocarbons are used. The compound ZOH, ethyl azodicarboxylate and triphenylphosphine are used in the amount of about 1 to 1.5 moles based on 1 mole of the hydroxyimino compound VII. The reaction takes about several tens minutes to a few hours at temperature range of about 0 to 50° C.

When using $ZR^6$, the reaction between $ZR^6$ and the hydroxyimino compound VII is a normal etherification reaction which is conducted in a solvent. As the solvent, there can be used the above-mentioned solvents such as ethers, esters, halogenated hydrocarbons, hydrocarbons, amides, ketones, nitrites, alcohols, water, or the like, or a mixed solvent. The solvent is preferably a mixed solvent of water and a water-miscible solvent, for example, water-containing methanol, water-containing ethanol, water-containing acetone, water-containing dimethyl sulfoxide, or the like. The reaction is also allowed to proceed smoothly in the presence of an appropriate base. Examples of the base include inorganic base such as alkaline metal salts including sodium carbonate, sodium bicarbonate, potassium carbonate, etc., and alkaline metal hydroxides including sodium hydroxide, potassium hydroxide, etc. This reaction can also be conducted in a buffer (e.g. phosphate buffer) at pH 7.5 to 8.5. The compound $ZR^6$ and the base are used at about 1 to 5 moles and about 1 to 10 moles, preferably about 1 to 3 moles and about 1 to 5 moles, respectively, on the basis of 1 mole of compound VII. The reaction temperature can be in the range of about −30 to 100° C., preferably about 0 to 80° C. The reaction time is about 10 minutes to 15 hours, preferably about 30 minutes to 5 hours.

A function group(s) such as amino, hydroxy, carboxy, or the like, can be protected with an appropriate protecting group when effecting the aforementioned respective reaction.

The method of deprotection and purification for producing the compound of the present invention will be hereinafter explained.

Deprotection Method:

For example, a monohalogenoacetyl group (e.g. chloroacetyl, bromoacetyl) can be removed by using thiourea; an alkoxycarbonyl group (e.g. methoxycarbonyl, ethoxycarbonyl, tert-butoxycarbonyl) can be removed by using an acid (e.g. hydrochloric acid); an aralkyloxycarbonyl group (e.g. benzyloxycarbonyl, p-methylbenzyloxycarbonyl, p-nitrobenzyloxycarbonyl) can be removed by catalytic reduction; 2,2,2-trichloroethoxycarbonyl can be removed by using zinc and an acid (e.g. acetic acid); 2-methylsulfonylethyl ester can be removed by using an alkali; an aralkyl ester (e.g. benzyl ester, p-methoxybenzyl ester, p-nitrobenzyl ester) can be removed by using an acid (e.g. formic acid, trifluoroacetic acid, $AlCl_3$, $TiCl_4$) or by catalytic reduction; a 2,2,2-trichloroethyl ester can be removed by using zinc and an acid (e.g. acetic acid); and a silyl ester (e.g. trimethylsilyl ester, tert-butyldimethylsilyl ester) can be removed by using water alone.

Purification Method:

The compound of the present invention or a synthetic intermediate thereof obtained by the above-mentioned or other production methods can be isolated and purified according to known methods including extraction, column chromatography, precipitation, recrystallization, and the like. Further, the isolated compound can then be converted into desired physiologically acceptable salts by a known method.

The compound of the present invention is useful as a drug, especially, a valuable antibiotic because it shows an antibacterial activity of broad spectrum, a long blood half-life, and an excellent in vivo dynamics. Therefore, the compound can be used directly or indirectly for the purpose of preventing or treating various diseases caused by pathogenic microorganisms in human and mammals (e.g. mouse, rat, rabbit, canine, cat, bovine, swine), for example, sinopulmonary infection and urinary infection. The antibacterial spectra are characteristic in the following points.

(1) It is highly active on various Gram-negative bacteria.
(2) It is highly active on Gram-positive bacteria.
(3) It is highly active on methicillia resistant *Staphylococcus aurous* (MRSA).

(4) It is highly active on Pseudomonas which is insensitive to the treatment with a normal cephalosporin antibiotic.

(5) It is also highly active on various Gram-negative bacteria capable of producing β-lactamase (e.g. genus Escherichia, genus Enterobacter, genus Serratia, genus Proteus, etc.).

Microorganisms of the genus Pseudomonas have so far been treated with aminoglycoside antibiotics such as amikacin, gentamicin, and the like. The compound of the present invention has a great advantage over the aminoglycosides because the former exerts antibacterial activities equivalent to the latter with by far the less toxicity to human and animals.

The compound of the present invention can be orally or parenterally administered in the form of solid preparations (e.g. tablets, capsules, granules, powders, etc.) or liquid preparations (e.g. syrups, injections, etc.) in association with pharmaceutically acceptable carriers.

As the pharmaceutically acceptable carriers, there can be used various organic or inorganic carriers which have been commonly used as materials for pharmaceutical preparations. In case of the solid preparation, excipients, lubricants, binders and disintegrators, and in case of the liquid preparation, solvents, solubilizers, suspending agents, isotonicities, buffering agents and soothing agents, can be appropriately combined. If necessary, preparation additives such as antiseptics, antioxidants, colorants and sweetening agents can also be used according to conventional methods. Preferred examples of the excipient include lactose, sucrose, D-mannitol, starch, crystalline cellulose, light anhydrous silicic acid, and the like. Preferred examples of the lubricant include magnesium stearate, calcium stearate, talc, colloidal silica, and the like. Preferred examples of the binder include crystalline cellulose, sucrose, D-mannitol, dextrin, hydroxypropyl cellulose, hydroxypropylmethyl cellulose, polyvinylpyrrolidone, and the like. Preferred examples of the disintegrator include starch, carboxymethyl cellulose, calcium carboxymethyl cellulose, sodium cross carboxymethyl cellulose, sodium carboxymethyl starch, and the like. Preferred examples of the solvent include distilled water for injection, alcohol, propylene glycol, macrogol, sesame oil, corn oil, and the like. Preferred examples of the solubilizer include polyethylene glycol, propylene glycol, D-mannitol, benzyl benzoate, ethanol, tris-aminomethane, cholesterol, triethanolamine, sodium carbonate, sodium citrate, and the like. Preferred examples of the suspending agent include surfactants such as stearyltriethanolamine, sodium lauryl sulfate, laurylaminopropionic acid, lecithin, benzalkonium chloride, benzetonium chloride, glycerin monostearate, and the like; and hydrophilic polymer such as polyvinyl alcohol, polyvinylpyrrolidone, sodium carboxymethyl cellulose, methyl cellulose, hydroxymethyl cellulose, hydroxyethyl cellulose, hydroxypropyl cellulose, and the like. Preferred examples of the isotonicity include sodium chloride, glycerin, D-mannitol, and the like. Preferred examples of the buffering agent include buffer solutions of phosphate, acetate, carbonate and citrate. Preferred examples of the soothing agent include benzyl alcohol, and the like. Preferred examples of the antiseptic include paraoxybenzoates, chlorobutanol, benzyl alcohol, phenethyl alcohol, dehydroacetic acid, sorbic acid, and the like. Preferred examples of the antioxidant include sulfite, ascorbate, and the like. It is also possible to obtain a preparation having an antibacterial activity of broader spectrum by mixing other active ingredient(s) (e.g. β-lactam antibiotic).

The compound of the present invention can be used for preventing and treating bacterial infections such as respiratory infection, urinary infection, pyogenic disease, biliary infection, intestinal infection, obstetric infection, otolaryngologic infection and surgical infection of human and other mammals. Although the dosage varies depending on the conditions and weight of patients and administration method, the daily dose of an active ingredient for adult for parenteral administration can generally be about 0.5–80 mg/kg, preferably about 2–40 mg/kg, which is administered in one to three divisions, by intravenous or intramuscular injection. For oral administration, the daily dose of an active ingredient can be 1–100 mg/kg, preferably about 2.5–50 mg/kg, which is administered in one to three divisions.

BEST MODE FOR CARRYING OUT THE INVENTION

The abbreviations used in the following Preparations and Examples are as follows:

THF: tetrahydrofuran, DBU: 1,8-diazabicyclo[5,4,0]undecene, DMF: dimethylformamide, DMSO: dimethyl sulfoxide, DIBAH: diisobutylaluminum hydride, TMS: trimethylsilyl, Me: methyl, Et: ethyl, iPr: isopropyl, 'Bu: tert-butyl, Ph: phenyl, MsCl: methanesulfonyl chloride.

(Protecting Group)

Boc: tert-butyloxycarbonyl

Im: imidazolyl

BH: diphenylmethyl

PMB: p-methoxybenzyl

POM: tert-butylcarbonyloxymethyl

With respect to the expression of the compounds, the figure underlined ordinarily corresponds to a compound of the same number in the chemical formula, wherein the figure is underlined by "~".

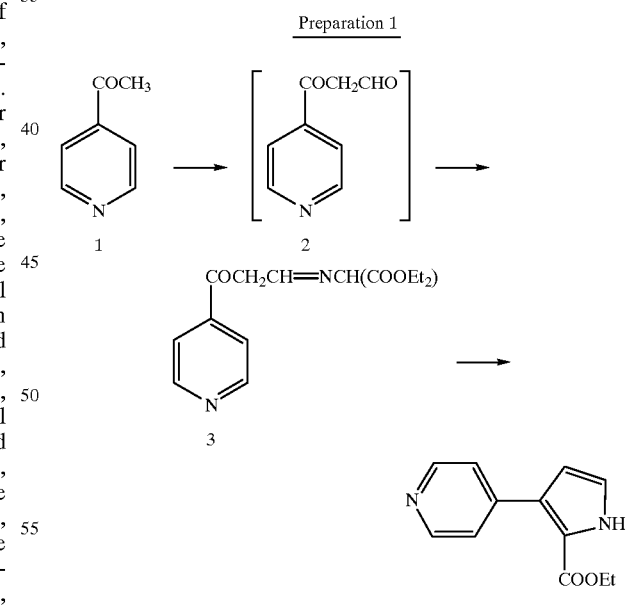

Preparation 1

(1) To a solution of 1 (7.74 ml, 70 mmol) and ethyl formate (11.3 ml, 0.14 moles) in 150 ml of benzene was added MeONa (powder) (7.6 g, 0.14 moles), and the mixture was stirred at room temperature for 1.5 hours. The mixture was refluxed for additional 30 minutes and benzene was distilled away under reduced pressure. The resulting residue was dissolved in 150 ml of THF. To the solution were added acetic acid (8.6 ml, 0.15 moles) and diethyl aminomalonate (14.8 g, 70 mmol) in series, and the mixture was stirred at room temperature for 2 hours. The reaction solution was poured into $NaHCO_3$-ice-cold water and extracted with ethyl acetate. The extract was washed with water, dried and concentrated under reduced pressure to obtain crude 3 as residue. The residue was purified by silica gel chromatography ($CH_2Cl_2$/ethyl acetate=3/1) to obtain 14.0 g of 3 (yield 65.3%).

Compound 3:
NMR(CDCl$_3$) δ: 1.33(6H,t,J=7.0 Hz), 4.32(4H,q,J=7.0 Hz), 4.65(1H,d,J=8.4 Hz), 5.86(1H,d,J=7.8 Hz), 6.99~7.10 (1H,m), 7.10(2H,d,J=5.6 Hz), 8.73(2H,d,J=5.6 Hz)

(2) To 3 (21.56 g, 70.4 mmol) was added 80 g of polyphosphoric acid, and the mixture was heated on an oil bath at 90° C. for 1 hour. The reaction solution was cooled, added to ice-cold water and neutralized with $Na_2CO_3$. The insoluble materials were collected by filtration, dissolved in ethyl acetate, dried over anhydrous magnesium sulfate and concentrated under reduced pressure. The resulting crystalline residue was washed with ethyl acetate to obtain 6.02 g of 4 (yield 39.5%) as a crystalline powder.

Compound 4:
NMR(CDCl$_3$) δ: 1.29(3H,t,J=7.0 Hz), 4.230(2H,q,J=7.0 Hz), 6.44(1H,bs), 7.01(1H,bs), 7.59(2H,d,J=5.6 Hz), 8.60 (2H,d,J=5.6 Hz) IR(Nujol) ν cm-1 :1702, 1599

(3) To a solution of sodium metal (2.58 g, 0.11 moles) in 250 ml of anhydrous ethanol was added a solution prepared by suspending 3 (15.58 g, 51 mmol) in 70 ml of ethanol under ice cooling. The reaction was heated to reflux for 9 hours. The reaction solution was concentrated under reduced pressure and the resulting residue was neutralized with 1N hydrogen chloride. The precipitated insoluble materials were collected by filtration, washed with water and then recrystallized from isopropanol to obtain 3.0 g of 4 (yield 27.3%).

Preparation 2

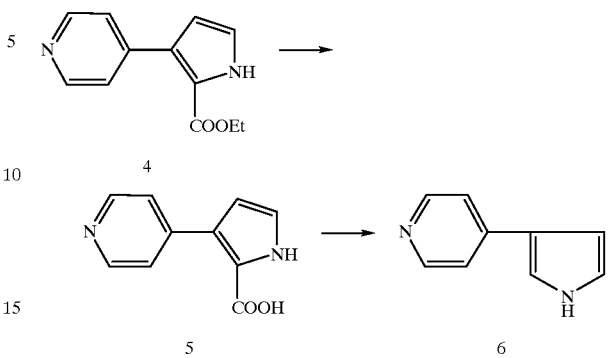

(1) To 4 (6.02 g, 27.8 mmol) were added 60 ml of ethanol and 60 ml of an aqueous solution containing NaOH (6.8 g, 0.17 moles), and the mixture was heated to reflux for 1 hour. After ethanol in the reaction solution was distilled away under reduced pressure, the solution was neutralized by adding acetic acid. The insoluble materials were collected by filtration, washed with water and then dried to obtain 4.53 g of 5 (yield 86.6%).

Compound 5: NMR(d$_6$-DMSO) δ: 6.42(1H,bs), 7.04(1H, bs), 7.56(2H,d,J=5.6 Hz), 8.52(2H,d,J=5.6 Hz)

(2) To a solution of 5 (3.28 g, 17.4 mmol) in 30 ml of DMF was added $H_2O$ (0.6 ml), and the mixture was heated to reflux overnight. The reaction was concentrated under reduced pressure. The residue was recrystallized from methanol to obtain 1.28 g of 6 (yield 51.0%).

Compound 6: NMR(d$_6$-DMSO) δ: 6.58(1H,bs), 6.86(1H, bs), 7.49(1H,bs), 7.00(2H,d,J=6.2 Hz), 8.41(2H,d,J=6.2 Hz) IR(Nujol) ν cm-1:3144, 3104, 3024, 1704, 1605

Preparation 3

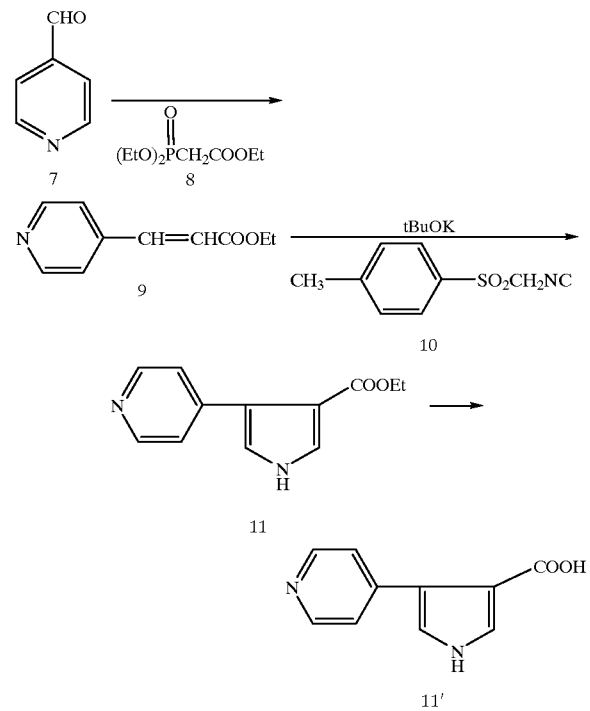

(1) To a solution of 7 (10.7 g, 0.1 moles) and 8 (22.4 g, 0.1 moles) in 220 ml of THF were added H₂O (30 ml) and K₂CO₃ (16.6 g, 0.12 moles) successively, and the mixture was stirred at room temperature overnight. The reaction was concentrated under reduced pressure and the resulting residue was dissolved in ethyl acetate. The solution was washed with water, dried and then concentrated under reduced pressure. The residue was recrystallized from ethyl ether-n-hexane to obtain 15.61 g of 9 (yield 88.1%).

Compound 9: NMR(CDCl₃) δ : 1.35(3H,t,J=7 Hz), 4.28 (2H,q,J=7 Hz), 6.60(1H,d,J=16 Hz), 7.38(2H,d,J=6 Hz), 7.60(1H,d,J=16 Hz), 8.65(2H,d,J=6 Hz) IR(CHCl₃) ν cm⁻¹:1711, 1645, 1597, 1551

(2) To a suspension of t-BuOK (12.5 g, 0.106 moles) in 150 ml of THF was added dropwise a solution of 9 (15.61 g, 88 moles) and 10 (18.92 g, 97 mmol) in THF (150 ml) over 40 minutes so as to keep the reaction temperature below 30° C. The reaction solution was stirred at room temperature for 1 hour and neutralized with 10% HCl. The reaction solution was distilled to remove THF and dissolved in ethyl acetate. The solution was washed with water, dried over anhydrous magnesium sulfate and concentrated under reduced pressure. The residue was purified by silica gel column chromatography (ethyl acetate). The residue of the eluent was washed with ethyl acetate to obtain 13.9 g of 11 (yield 73.0%). The corresponding carboxylic acid 11' can be obtained by treating the product according to the same manner as that described in Preparation 2.

Preparation 4

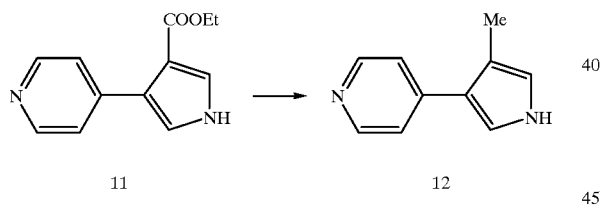

11    12

To a suspension of LiAlH₄ (12.14 g, 0.32 moles) in 500 ml of THF was added slowly a solution of a compound 11 (34.55 g, 0.16 moles) in THF (500 ml), and the mixture was refluxed for 1 hour and 30 minutes and ice-cooled. When a saturated Na₂SO₄ solution and 4N NaOH were added to the mixture, oily insoluble materials were precipitated. The mother liquor was decanted and the insoluble materials were washed with THF. The mother liquors were combined and concentrated under reduced pressure and treated by silica gel column chromatography (methanol/ethyl acetate=1/9). The eluent was concentrated under reduced pressure and the residue was washed in turn with ethyl ether and hexane to obtain 21.01 g of 12 (yield 83%) as a pale yellow crystal. mp.152–155° C.

Compound 12: NMR(d₆-DMSO) δ: 2.22(3H,s), 6.66(1H, bs), 7.25(1H,bs), 7.43(2H,d,J=6.0 Hz), 8.43(2H,d,J=6.0 Hz) IR(KBr) ν cm⁻¹: 3468, 1600

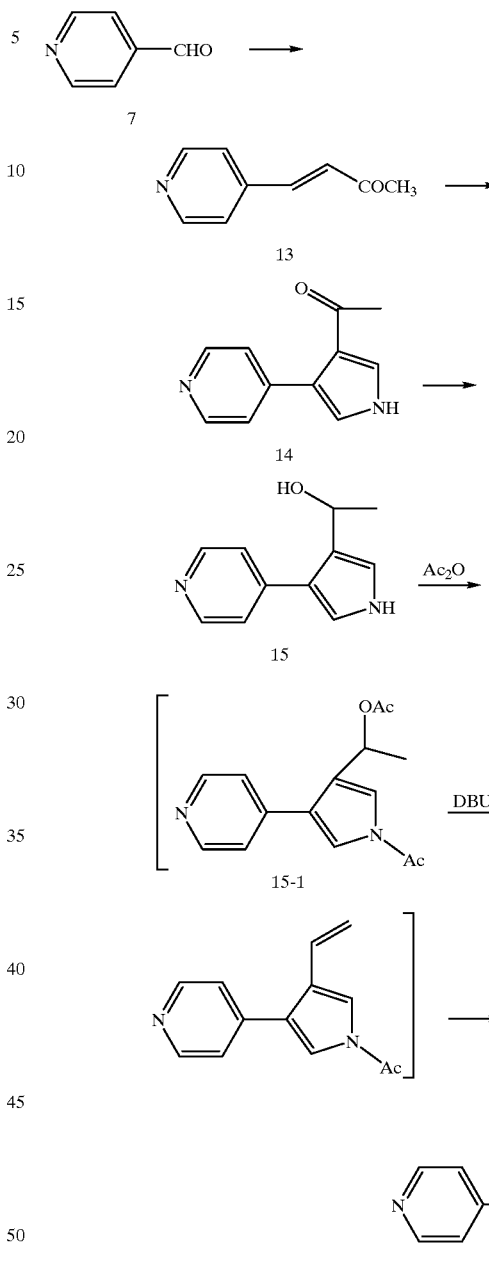

(1) To a solution of 7 (18.53 g, 173 mmol) in THF (250 ml) was added Ph₃P=COCH₃ (55 g, 173 mmol) at room temperature, and the mixture was stirred for 1 hour and concentrated under reduced pressure. To the residue were added toluene (50 ml) and hexane (20 ml). The precipitated Ph₃P=O was removed by filtration and the filtrate was concentrated to obtain 34.2 g of oily crude 13 (containing Ph₃P=O).

Compound 13: NMR(CDCl₃) δ: 2.44(3H,s), 6.86(1H,d, J=16.4 Hz), 7.45(1H,d,J=16.4 Hz), 7.35(2H,dd,J=1.4,4 Hz), 8.69(2H,dd,J=1.4,4 Hz)

(2) To 90% t-BuOK (21.59 g, 173.17 mmol)/THF was added a mixture of the crude 13 prepared in the above at 20° C. and tosylmethyl isocyanide (33.81 g, 173.17 mmol)/THF (300 ml) under ice cooling at 20 to 25° C. After stirring at 25° C. for 1 hour, acetic acid (0.5 ml) was added, and then H$_2$O (300 ml) and ethyl acetate (700 ml) were added to separate the organic layer. The organic layer was washed with water and concentrated under reduced pressure. The residue was crystallized from toluene to obtain 21.38 g of a crude product 14. The yield from 7 was 66.4%. m.p. 177–194° C.

Compound 14: NMR(d$_6$-DMSO) δ: 2.39(3H,s), 7.19(1H, bs), 7.45(2H,dd,J=1.6,4.6 Hz), 7.80(1H,bs), 8.43(2H,dd,J= 1.6,4.6 Hz)

(3) To an ethanol solution (200 ml) of 14 (20.9 g, 112.3 mmol) was added NaBH$_4$ (4.25 g)/H$_2$O (15 ml), and the mixture was stirred at room temperature overnight. Excess NaBH$_4$ was decomposed with acetic acid. The solution was concentrated under reduced pressure. To the residue was added H$_2$O/ethyl acetate. The aqueous layer was made basic with K$_2$CO$_3$. The organic layer was separated, washed with a saturated saline solution and concentrated. The residue was crystallized from toluene/ethyl acetate (1/1) to obtain 15 (14.76 g). m.p. 153–156° C.

Compound 15: NMR(d$_6$-DMSO) δ: 1.38(3H,d,J=6.2 Hz), 4.78–4.95(1H,m), 6.84(1H,bs), 7.20(1H,bs), 7.60(2H,dd,J= 1.6,4.6 Hz), 8.43(2H,dd,J=1.6,4.6 Hz) IR(Nujol) ν cm$^{-1}$: 3308, 1596, 1530, 1418, 1213, 1058, 979

(4) To 15 (9.03 g, 48.03 mmol) was added acetic anhydride (40 ml), and the mixture was stirred at 90° C. for 1 hour. Excess acetic anhydride was distilled away under reduced pressure. To the oily residue was added H$_2$O (30 ml)/ethyl acetate (150 ml). K$_2$CO$_3$ was added until the solution became basic. The organic layer was separated, washed with water and concentrated under reduced pressure to obtain 15-1 (oily) (9.14 g). After dissolving 15-1 in THF (50 ml) and adding DBU (12 ml), the reaction was conducted at 70° C. for 8 hours. The reaction solution was concentrated under reduced pressure. The residue was dissolved in ethyl acetate, washed with water and concentrated. To a solution of the residue in methanol (30 ml) was added 2N NaOH (20 ml), and the mixture was stirred at room temperature for 1 hour. After the completion of the reaction, the reaction solution was concentrated under reduced pressure until the volume becomes about 25 ml, and extracted with ethyl acetate. The residue was crystallized from toluene to obtain 16 (3.73 g, yield: 45.7% from 15). m.p. 159–160° C.

Compound 16: NMR(d$_6$-DMSO) δ: 5.00(1H,dd,J=4.0, 10.8 Hz), 5.42(1H,dd,J=4,17.4 Hz), 6.70(1H,dd,J=10.8,17.4 Hz), 7.09(1H,bs), 7.17(1H,bs), 7.36(1H,d,J=5.8 Hz), 8.47 (1H,d,J=5.8) IR(Nujol)ν cm$^{-1}$:2716, 1932, 1599, 1520, 1412, 1211, 1076, 986

Preparation 6

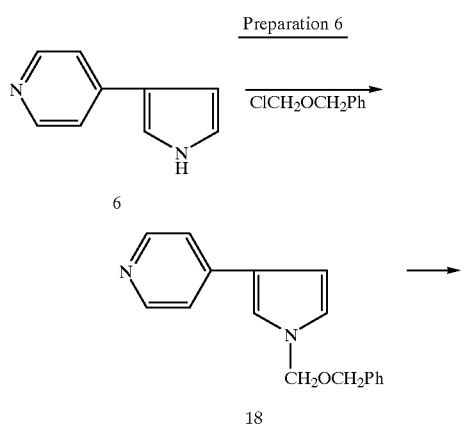

(1) To a solution of 6 (1.44 g, 10 mmol) in 20 ml of DMF was added NaH (0.42 g, 10.5 mmol) under ice cooling, and the mixture was stirred at room temperature for 30 minutes and cooled to −30° C. After adding chloromethyl benzyl ether (ClCH$_2$OCH$_2$Ph) (1.46 ml, 10.5 mmol) to the solution, the mixture was stirred at the same temperature for 30 minutes. The reaction solution was poured into ice-cold water, and extracted with ethyl acetate. The extract was washed with water, dried and concentrated under reduced pressure. The residue was purified by silica gel chromatography (CH$_2$Cl$_2$/ethyl acetate=9/1-1/1) to obtain 2.31 g of 18 (yield 87.4%).

Compound 18: NMR(CDCl$_3$) δ: 4.46(2H,s), 5.29(2H,s), 6.59(1H,bs), 6.67(1H,bs), 7.26(1H,bs), 7.3~7.4(5H,m), 7.41 (2H,d,J=6 Hz), 8.51(2H,d,J=6 Hz)

(2) To a solution of 18 (26.9 g, 0.1 moles) in 150 ml of DMF was added dropwise phosphorous oxychloride (27.7 ml, 0.3 moles) while maintaining the reaction temperature below 25° C., and the mixture was stirred with heating at 40 to 45° C. for 3 hours. The reaction solution was poured into 500 ml of water containing 127 g of K$_2$CO$_3$ under ice cooling. The solution was then extracted with ethyl acetate, washed with water, and concentrated under reduced pressure. The resulting residue was crystallized from ether to obtain 17.15 g of 19 (yield 60.0%).

Compound 19: NMR(CDCl$_3$) δ: 4.60(2H,s), 5.85(2H,s), 7.33(6H,m), 41(2H,d,J=5.6 Hz), 7.54(1H,bs), 8.60(2H,d,J= 5.6 Hz)

(3) To a solution of 19 (7.8 g, 27.7 mmol) in 150 ml of dichloromethane was added 15 ml of anisole and aluminum chloride (11 g, 83.1 mmol) in series at room temperature, and the mixture was stirred for 4 hours. After adding aluminum chloride (7.4 g, 55.4 mmol), the mixture was stirred for 1 hour. The reaction solution was poured into ice-cold water and diluted hydrochloric acid was added thereto to give a clear solution. The aqueous solution was washed with ethyl ether, adjusted to pH 8 with 4N NaOH and extracted with methyl ethyl ketone. The organic layer was dried and concentrated under reduced pressure. The crystalline residue was washed with ethyl ether-n-hexane to obtain 3.56 g of 20 (yield 74.3%).

Compound 20: NMR(CD$_3$OD) δ: 7.51(1H,bs), 7.65(2H, d,J=6.0 Hz), 7.79(1H,bs), 8.44(2H,d,J=6.0 Hz), 9.55(1H, bs)

Compound 20: NMR(DMSO) δ: 7.57(1H,bs), 7.64(2H,d,J= 6.2 Hz), 7.97(1H,bs), 8.49(2H,d,J=6.2 Hz), 9.55(1H, bs) IR(Nujol) ν cm$^{-1}$:1671, 1655, 1603

Preparation 7

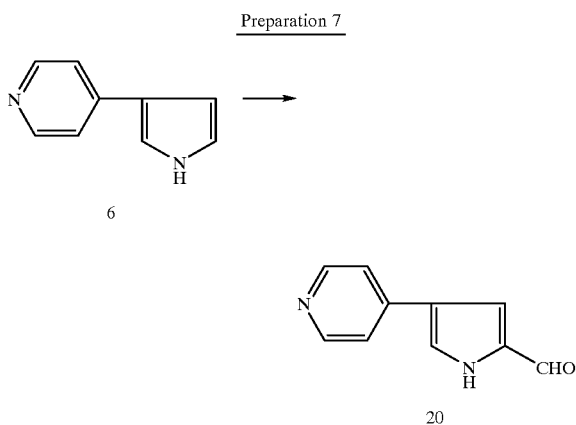

To a solution of 6 (5.77 g, 40 mmol) in 70 ml of DMF was added dropwise phosphorous oxychloride (14.5 ml, 0.116 moles) under ice cooling. After stirring at 130° C. for 5 hours, the solution was poured into ice-cold water and neutralized with sodium hydrogencarbonate. To the solution was added ethyl acetate and the insoluble materials were removed by filtration. The organic layer was washed with a saturated saline solution, dried, and concentrated under reduced pressure. The residue was recrystallized from methanol to obtain 0.97 g of 21 (yield 14.0%).

Preparation 8

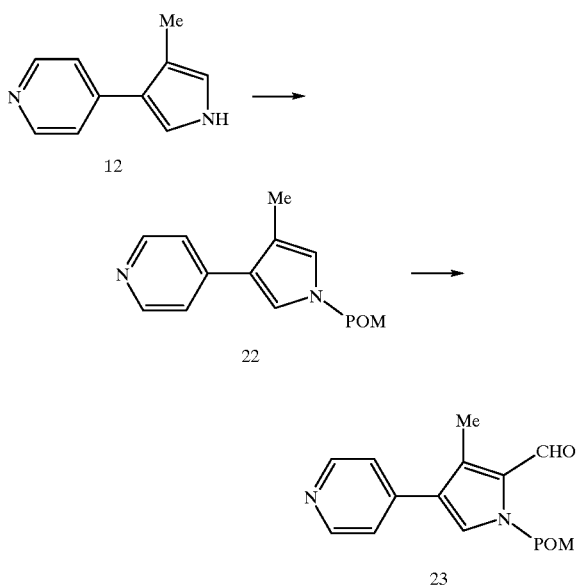

(1) To a solution of 12 (21.0 g, 0.13 moles) in 250 ml of DMF was added 60% NaH (5.72 g, 0.143 moles) under ice cooling, and the mixture was stirred at the same temperature for 20 minutes. To the reaction was added 100 ml of DMF, and the mixture was cooled to −45° C. After adding POM-Cl (ClCH$_2$OCOBu$^t$) (20.6 ml, 0.143 moles) to the reaction solution, the mixture was stirred at the same temperature for 30 minutes, poured into H$_2$O (700 ml) and extracted twice with ethyl acetate. The ethyl acetate layer was washed with water, a saturated saline solution, dried over MgSO$_4$, and distilled away under reduced pressure. The residue was treated by silica gel chromatography (toluene/ethyl acetate= 1/2) to obtain 33.73 g of a white crystal 22 (yield 95%). m.p. 42–44° C.

Compound 22: NMR(CDCl$_3$) δ: 1.19(9H,s), 2.24(3H,s), 5.75(2H,s), 6.68(1H,d,J=2.4 Hz), 7.07(1H,d,J=2.4 Hz), 7.34 (2H,d,J=6.2 Hz), 8.53(2H,d,J=6.2 Hz) IR(CHCl$_3$) ν cm$^{-1}$:1732, 1602

(2) To 150 ml of DMF cooled at −20° C. was added POCl$_3$ (45.9 ml, 0.49 moles). A solution of 22 (33.4 g, 0.12 moles) in DMF (40 ml) was then added dropwise. The solution was stirred at room temperature for 15 minutes, and then at 60° C. for 80 minutes. The resulting reaction solution was poured into 1000 ml of water, and K$_2$CO$_3$ (102 g, 0.74 moles) was added thereto. After adding 700 ml of ethyl acetate, the solution was neutralized with NaHCO$_3$. The ethyl acetate layer was washed with water and a saturated saline solution, dried over MgSO$_4$, and distilled away under reduced pressure. To the residue were added ethyl ether and hexane, and the precipitated crystals were filtered to obtain 27.6 g of a pale yellow crystal 23 (yield 75%). m.p. 76–78° C.

Compound 23: NMR(CDCl$_3$):1.18(9H,s), 2.51(3H,s), 6.24 (2H,s), 7.29(2H,d,J=6.4 Hz), 7.33(1H,s), 8.62(2H,d,J=6.4 Hz), 9.90(1H,s) IR(CHCl$_3$) ν cm$^{-1}$:1731, 1657, 1603

Preparation 9

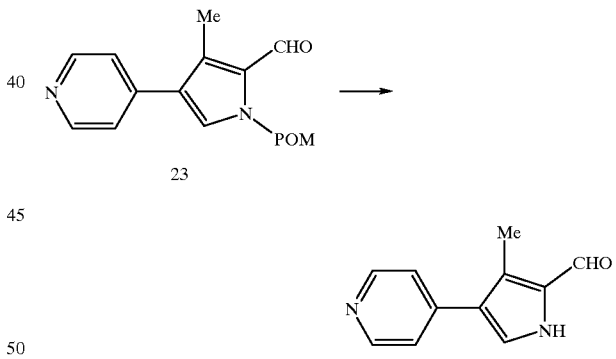

To a solution of 23 (20.0 g, 66.6 mmol) in 500 ml of methanol was added a solution of NaOH (13.3 g, 0.33 moles) in H$_2$O (200 ml), and the mixture was stirred at room temperature for 1 hour. The reaction solution was concentrated under reduced pressure, and the precipitated insoluble materials were filtered to obtain 11.0 g of a white crystal 24 (yield 89%). m.p. 214–216° C.

Compound 24: NMR(d$_6$-DMSO) δ: 2.50(3H,s), 7.50(2H, d,J=6.0 Hz), 7.65(1H,bs), 8.53(2H,d,J=6.0 Hz), 9.73(1H,s), 12.24(H,bs) IR(KBr) ν cm$^{-1}$: 1655, 1604

Preparation 10

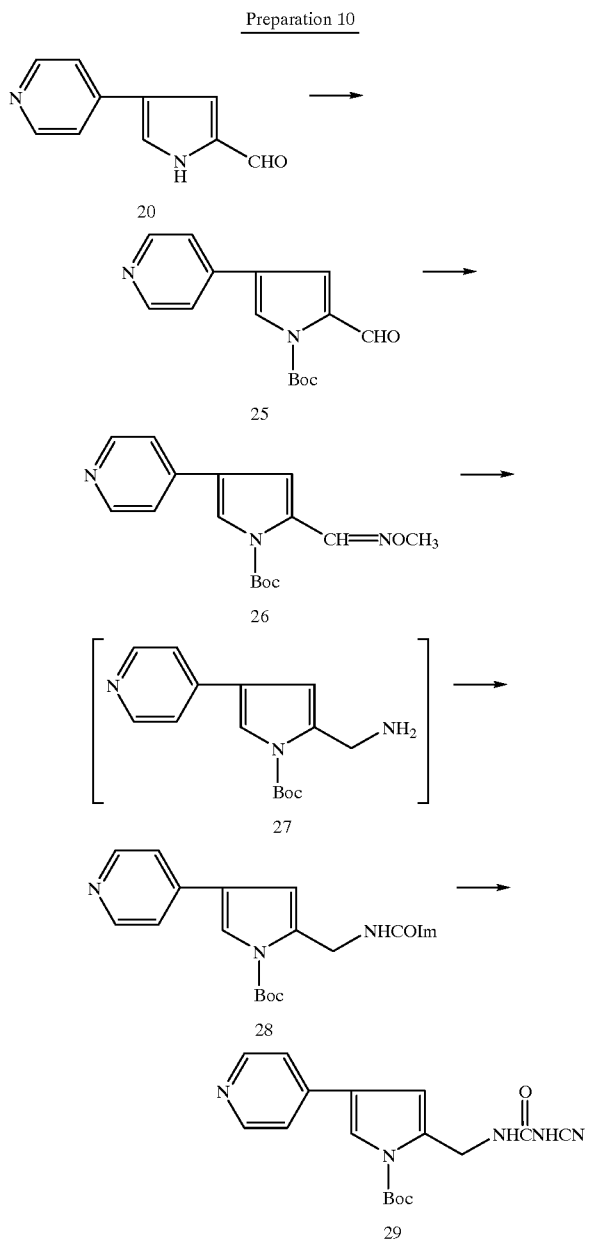

(1) To a solution of 20 (3.46 g, 20 mmol) in 20 ml of DMF was added (Boc)$_2$O (5.1 ml, 22 mmol), and the mixture was stirred at room temperature for 1 hour. The reaction solution was poured into ice-cold water and extracted with ethyl acetate. The organic layer was washed with water, dried and concentrated under reduced pressure. The resulting residue was recrystallized from toluene to obtain 5.24 g of 25 (yield 96.2%).

Compound 25: NMR(CDCl$_3$) δ: 1.68(9H,s), 7.43(2H,d, J=6.0 Hz), 7.51(1H,d,J=2.0 Hz), 7.82(1H,d,J=2.0 Hz), 8.62 (2H,d,J=6.0 Hz) IR(CHCl$_3$) ν cm$^{-1}$: 1755, 1666, 1604

(2) To a solution of 25 (2.72 g, 10 mmol) in 50 ml of methanol was added O-methylhydroxylamine hydrochloride (0.92 g, 11 mmol), and the mixture was stirred at room temperature for 1 hour. The reaction solution was concentrated under reduced pressure, and the resulting residue was dissolved in water. The solution was neutralized with NaHCO$_3$, extracted with ethyl acetate, washed with water, dried, and concentrated under reduced pressure to obtain 2.99 g of 26 (yield 92.2%) as a crystalline residue.

Compound 26: NMR (CDCl$_3$ (mixture of syn/anti)) δ: 1.64, 1.65(9H,s+s), 3.96/4.08=5/1(3H,s+s), 7.09/7.45=5/1 (1H,bs+bs), 7.43(2H,d,J=6.2 Hz), 7.68/7.72=1/5(1H,bs+bs), 8.58(2H,d,J=6.2 Hz), 8.28/8.64=1/5(1H,s) IR(CHCl$_3$) ν cm$^{-1}$: 11747, 1605

(3) To a suspension of 6.0 g of zinc powder in 20 ml of acetic acid was added dropwise a solution obtained by dissolving 26 (3.01 g, 10 mmol) in 20 ml of acetic acid with vigorously stirring under ice cooling, while maintaining the reaction temperature below 30° C. After stirring for 30 minutes, the zinc powder was removed by filtration and the mother liquor was concentrated under reduced pressure. The residue was dissolved in water and the solution was neutralized with NaHCO$_3$. To the solution was added aqueous ammonia, and the solution was extracted with ethyl acetate. The organic layer was washed with water, dried, and concentrated under reduced pressure to obtain 2.63 g of a crude product 27. The crude product 27 was dissolved in 50 ml of THF, and carbonyldiimidazole (2.43 g, 15 mmol) was added thereto. The mixture was stirred at room temperature for 1 hour and concentrated under reduced pressure. The crystalline residue was washed with water and ethyl ether, and dried to obtain 3.02 g of 28 (yield 82.2%).

Compound 28: NMR($d_6$-DMSO) δ: 1.58(9H,s), 4.66(2H, d,J=5 Hz), 6.85(1H,s), 7.05(1H,s), 7.68(2H,d,J=6 Hz), 7.75 (1H,s), 8.01(1H,s), 8.33(1H,s), 8.50(2H,d,J=6 Hz), 9.93(1H, t,J=5 Hz) IR(Nujol) ν $cm^{-1}$:3183, 1746, 1704, 1601

(4) To a solution of 28 (3.02 g, 8.22 mmol) and cyanamide (0.69 g, 16.4 mmol) in 50 ml of DMF was added sodium hydride (0.33 g, 8.22 mmol), and the reaction solution was stirred for 30 minutes with heating at 60° C. After adding 0.5 ml of acetic acid, the solution was concentrated under reduced pressure. To the residue were added ice-cold water and ethyl ether, and the mixture was adjusted to pH 6 by adding diluted hydrochloric acid with stirring. The precipitated insoluble materials were collected by filtration, washed with ethyl ether and water, and dried to obtain 1.37 g of 29 (yield 48.8%).

Compound 29: NMR($CDCl_3$+$CD_3OD$) δ: 1.65(9H,s), 4.57(2H,s), 6.62(1H,d,J=2 Hz), 7.43(2H,d,J=6 Hz), 7.60 (1H,d,J=2 Hz), 8.50(2H,d,J=6 Hz) IR($CHCl_3$) ν $cm^{-1}$:2260, 2155, 1740, 1610 Elemental analysis for $C_{17}H_{19}N_5O_3$·1.5$H_2O$: Calcd: C,55.43; H,6.02; N,19.01 Found: C,55.35; H,5.73; N,18.63

Preparation 11

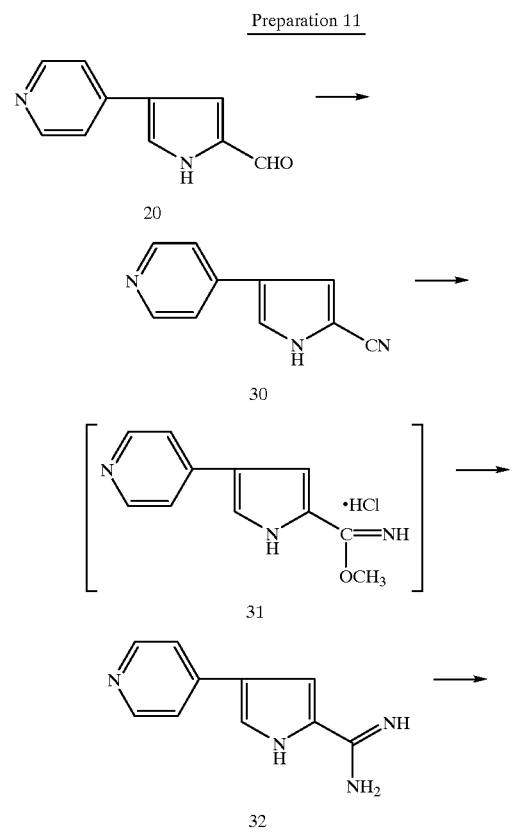

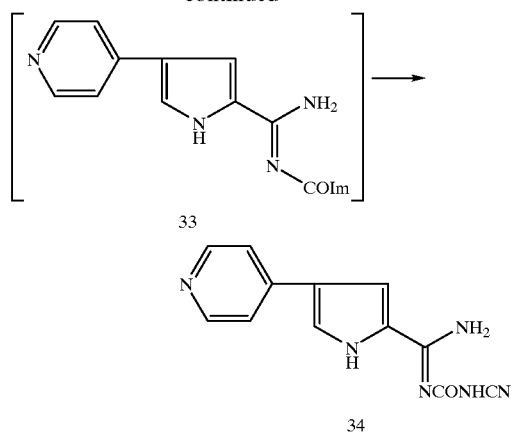

(1) To a solution of 20 (864 mg, 5 mmol) in 10 ml of formic acid was added hydroxylamine hydrochloride (417 mg, 6 mmol), and the mixture was stirred at 110° C. for 6 hours. The reaction solution was concentrated under reduced pressure. The residue was dissolved in water, and the solution was neutralized with $NaHCO_3$. The precipitated crystals were collected by filtration and recrystallized from methanol to obtain 394 mg of 30 (yield 46.6%).

Compound 30: NMR($d_6$-DMSO) δ: 7.56(1H,bs), 7.61 (2H,d,J=6.2 Hz), 7.91(1H,bs), 8.49(2H,d,J=6.2 Hz) IR(Nujol) ν $cm^{-1}$:3112, 2210, 1602, 1535

(2) To a solution of 30 (6.85 g, 40.5 mmol) in 500 ml of methanol was introduced hydrochloric acid gas under ice cooling until saturation is accomplished. The solution was stirred at the same temperature for 1 hour and then at room temperature for 1 hour. The reaction solution was concentrated under reduced pressure to obtain a crude product 31 as a crystalline residue. To the residue were added 100 ml of methanol and 160 ml of a solution of ammonia (5.3 moles) in methanol, and the mixture was stirred at room temperature for 24 hours. The reaction solution was concentrated under reduced pressure and the residue was dissolved in 150 ml of water. The solution was neutralized with 2N NaOH. The precipitated insoluble crystals were collected by filtration, washed with water and dried to obtain 6.78 g of 32 (yield 89.9%).

Compound 32: NMR($d_6$-DMSO) δ:7.34(1H,s), 7.34(2H, d,J=6 Hz), 7.49(1H,s), 8.32(2H,d,J=6 Hz) IR(Nujol) ν $cm^{-1}$:1667, 1602, 1550

(3) To a suspension of 32 (931 mg, 5 mmol) in 10 ml of DMF was added carbonyldiimidazole (891 mg, 5.5 mmol) with stirring, and the mixture was stirred at room temperature for 2 hours. Cyanamide monosodium salt was prepared by dissolving cyanamide (0.42 g, 10 mmol) in 6 ml of DMF, adding NaH (0.4 g, 10 mmol) to the solution, and stirring the mixture at room temperature for 30 minutes. The so obtained cyanamide monosodium salt was added to the above reaction mixture. The solution was stirred at room temperature for 3 hours, and at 50° C. for 1 hour. The reaction solution was concentrated under reduced pressure. The resulting residue was dissolved in water, neutralized by adding 10 ml of 1N hydrochloric acid, and the precipitated crystals were collected by filtration. The crystals were dissolved in 1N NaOH. A portion of insoluble materials was removed by filtration. The mother liquor was neutralized again with diluted hydrochloric acid. The precipitated crystals were collected by filtration, and dried to obtain 518 mg of 34 (yield 40.8%).

Compound 34: NMR(d$_6$-DMSO) δ: 7.58(2H,d,J=6 Hz), 8.06(1H,s), 8.11(1H,s), 8.56(2H,bs) IR(Nujol) ν cm$^{-1}$:2180, 1626, 1597

Preparation 12

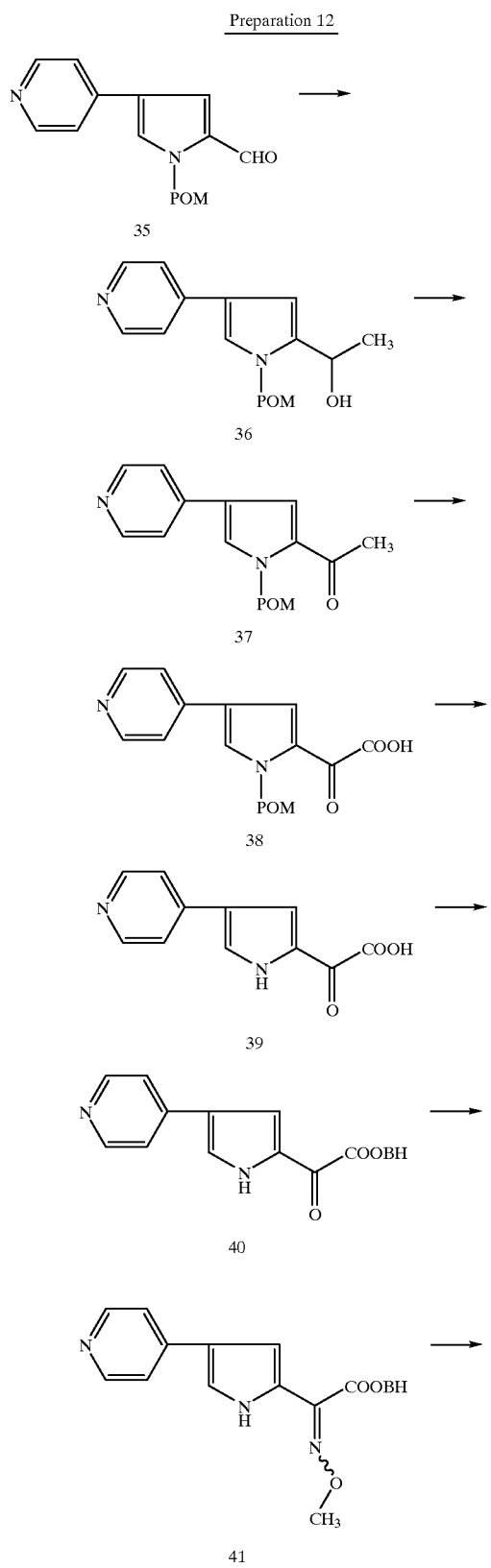

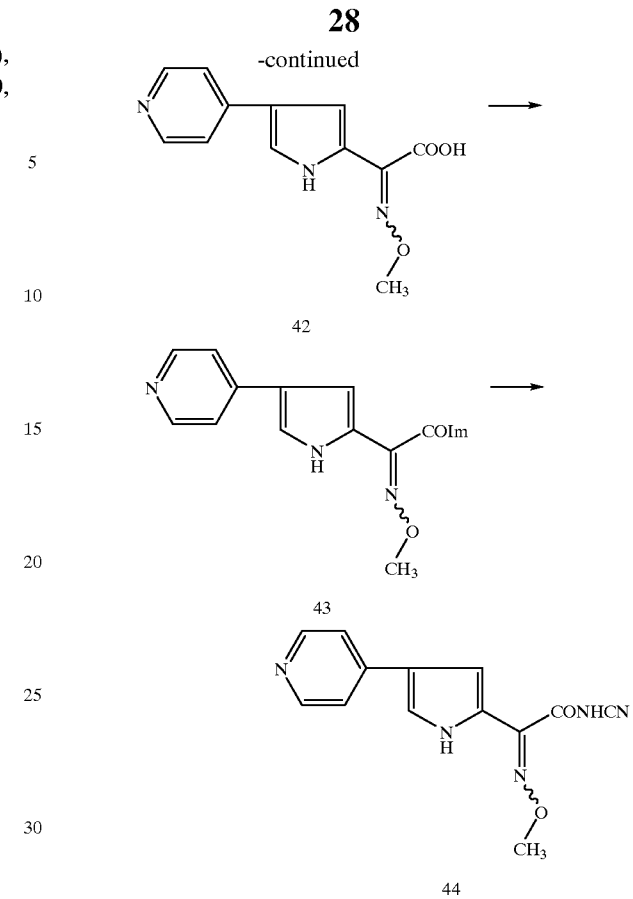

(1) Compound 35 (14.32 g, 50 mmol) was dissolved in 240 ml of THF with heating. The solution was cooled to −70° C. and 100 ml of a solution of MeMgBr (0.91 moles) in THF was added dropwise thereto at below −60° C. The solution was allowed to stand for 1 hour at the same temperature, and 20 ml of the same solution was added. After 1 hour, 100 ml of an aqueous solution containing 18 g of ammonium chloride was added to the reaction solution, followed by concentration under reduced pressure. The residue was extracted with ethyl acetate, washed with water and concentrated under reduced pressure. The resulting residue was crystallized from ethyl ether-n-hexane to obtain 14.0 g of 36 (yield 86.5%).

Compound 36: NMR(CDCl$_3$) δ: 1.49(9H,s), 1.68(3H,d, J=7 Hz), 5.02(1H,q,J=7 Hz), 5.97, 6.03(2H,ABq,J=8.0 Hz), 6.51(1H,d,J=2 Hz), 7.28(1H,d,J=2 Hz), 7.35(2H,d,J=6 Hz), 8.48(2H,d,J=6 Hz (2) To a solution of 36 (14.0 g, 46.3 mmol) in 250 ml of dichloromethane was added 14 g of manganese dioxide, and the solution was heated to reflux with stirring for 1.5 hours. To the reaction was further added 7 g of manganese dioxide five times every 1 hour. After adding 14 g of manganese dioxide, the solution was heated to reflux with stirring overnight. Further, 14 g of manganese dioxide was added and the solution was heated to reflux with stirring for 7 hours. Manganese dioxide was removed by filtration from the reaction solution. The solution was washed with dichloromethane and methanol, and the mother liquor was concentrated under reduced pressure. The residue was recrystallized from isopropanol to obtain 11.6 g of 37 (yield 83.4%).

Compound 37: NMR(CDCl$_3$) δ: 1.18(9H,s), 2.53(3H,s), 6.29(2H,s), 7.30(1H,d,J=2 Hz), 7.40(2H,d,J=6.0 Hz), 7.51 (1H,d,J=2 Hz), 8.58(2H,d,J=6.0 Hz) IR(Nujol) ν cm$^{-1}$:1718, 1646, 1602

(3) To a solution of 37 (11.6 g, 39 mmol) in 120 ml of pyridine was added selenium dioxide (9.6 g, 86 mmol), and the solution was heated to reflux for 7 hours. The reaction solution was concentrated under reduced pressure and the residue was added to aqueous sodium hydrogencarbonate, and the mixture was stirred. The insoluble materials were removed by filtration and treated with active carbon. The mother liquor was adjusted to pH 5 with diluted hydrochloric acid. The precipitated crystals were collected by filtration, washed with water, and dried to obtain 8.05 g of 38 (yield 62.5%).

Compound 38: NMR(d$_6$-DMSO) δ: 1.11(9H,s), 6.21(2H, s), 7.71(2H,d,J=6.0 Hz), 7.78(1H,d,J=1.6 Hz), 8.29(1H,d,J= 1.6 Hz), 8.56(2H,d,J=6.0 Hz)

(4) To a solution of 38 (5.98 g, 18.1 mmol) in 100 ml of methanol was added 45 ml of 2N NaOH, and the mixture was stirred at room temperature for 2 hours. Methanol in the reaction solution was distilled away under reduced pressure, and the aqueous solution was neutralized by adding 18 ml of 5N HCl. The precipitated crystals were collected by filtration and dried to obtain 4.8 g of 39.

Compound 2: NMR(d$_6$-DMSO) δ: 7.71(1H,bs), 7.79(2H, d,J=6.0 Hz), 8.11(1H,bs), 8.55(2H,d,J=6.0 Hz)

(5) To a suspension of 39 (4.8 g, 22.2 mmol) in 150 ml of methanol and 150 ml of dichloromethane was added diphenyldiazomethane (5.5 g, 28.3 mmol), and the mixture was stirred at room temperature overnight. The reaction solution was concentrated under reduced pressure, and the resulting residue was purified by silica gel column chromatography (dichloromethane/ethyl acetate=2/1) to obtain 3.92 g of 40 (yield 56.6%). Compound 40: NMR(CDCl$_3$) δ: 7.12(1H,bs), 7.3~7.5(12H,m), 7.56(1H,bs), 7.63(1H,bs), 8.58(2H,d,J=6.0 Hz) IR(Nujol) ν cm$^{-1}$:3386, 1725, 1645, 1603

(6) To a solution of 40 (2.72 g, 7.1 mmol) in 50 ml of dichloromethane was added a solution of O-methylhydroxylamine hydrochloride (1.78 g, 21.3 mmol) in methanol (15 ml), and the mixture was stirred at room temperature for 3 days. The reaction solution was concentrated under reduced pressure and the residue was neutralized with an aqueous sodium hydrogencarbonate solution. Then, the insoluble crystal was collected by filtration, washed with water and dried to obtain 2.93 g of 41.

Compound 41: NMR (d$_6$-DMSO(mixture of syn/anti) δ: 3.95/4.13:6.4/1 (3H,2×s) 6.81(1H,bs), 7.12(1H,s), 7.3~7.5 (10H,m), 8.06(2H,d J=6 Hz), 8.19(1H,bs), 8.71 (2H,d,J=6 Hz) IR(Nujol) ν cm$^{-1}$:3104, 2606, 1742, 1630, 1600

(7) To a solution of 41 (0.82 g, 2 mmol) in 5 ml of dichloromethane was added 1 ml of anisole. After adding 6 ml of trifluoroacetic acid under ice cooling, the mixture was stirred for 1 hour. The reaction solution was concentrated under reduced pressure and the residue was purified by column chromatography (water-methanol) to obtain 0.65 g of 42.

Compound 42: NMR(d$_6$-DMSO) δ: 3.91(3H,s), 6.94(1H, bs), 7.42(1H,bs), 7.9(3H,m), 8.55(2H,bs)

(8) To a solution of 42 (0.65 g, 2.65 mmol) in 10 ml of DMF was added carbonyldiimidazole (0.65 g, 4 mmol) under ice cooling, and the mixture was stirred at room temperature for 2 hours. The reaction solution was concentrated under reduced pressure and the residue was dissolved in ethyl acetate. The solution was washed with water, dried, and concentrated under reduced pressure to obtain 586 mg of a crude product 43 (yield 78.1%).

Compound 43: NMR (d$_6$-DMSO(mixture of syn/anti)) δ:3.94/4.25=2.5/1(3H,s×2), IsomerA,3.94(3H,s), 6.65(1H, bs), 7.13(1H s), 7.17(1H,bs), 7.35(2H,d,J=6 Mz), 7.53(1H, s), 8.02(1H,s), 8.52(2H d J=6 Hz), IsomerB, 4.25(3H,s), 7.30(1H,bs), 7.41(1H,s), 7.42(2H,d,J=6 Hz), 7.71(1H,bs), 7.73(1H s) 8.35(1H s) 8.57(2H d J=6 Hz)

(9) To a solution of 43 (586 mg, 2.1 mmol) in 4 ml of DMF was added a solution prepared by dissolving cyanamide (174 mg, 4.1 mmol) in DMF (2 ml), adding sodium hydride (60%) (164 mg, 4.1 mmol) and stirring for 30 minutes, and the mixture was stirred at room temperature for 1 hour. To the reaction solution was added 0.5 ml of acetic acid and the solution was concentrated under reduced pressure. The residue was eluted by column chromatography (20% methanol-H$_2$O). The residue of the eluent was washed with isopropanol to obtain 275 mg of a crystalline powder 44 (yield 48.6%).

Compound 44: NMR(d$_6$-DMSO(single isomer)) δ: 3.82 (3H,s), 6.88(1H,bs), 7.98(1H,bs), 8.12(2H,d,J=6 Hz), 8.60 (2H,d,J=6 Hz) IR(Nujol) ν cm$^{-1}$:3400, 2180, 1675, 1640, 1620

Preparation 13

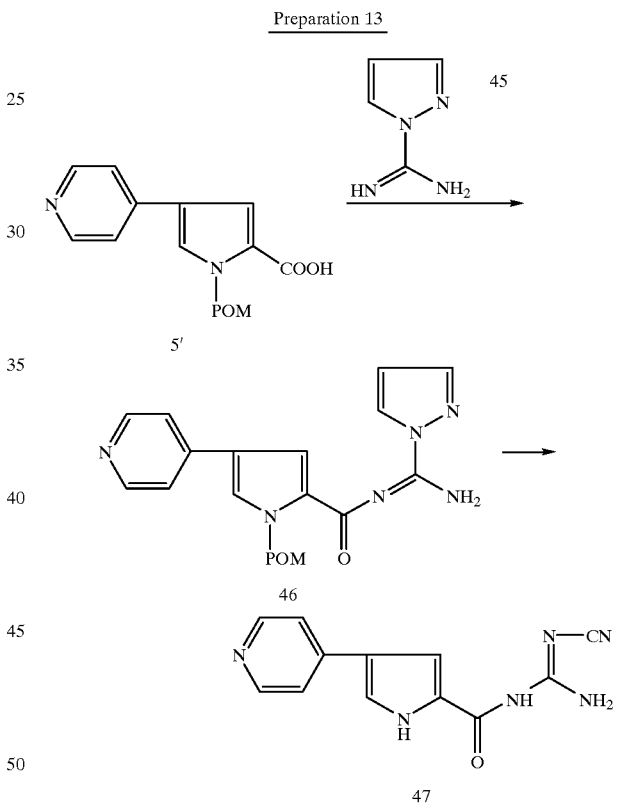

(1) To a suspension of 5' (3.07 g, 10 mmol) in 30 ml of DMF was added 1-hydroxybenzotriazole (2.03 g, 15 mmol) and water-soluble carbodiimide (2.88 g, 15 mmol) in series, and the mixture was stirred at room temperature for 1 hour. To the reaction solution were added 45 (2.2 g, 15 mmol) and a solution of diisopropylethylamine (2.6 ml, 15 mmol) in DMF (10 ml), and the mixture was stirred at room temperature for 1 hour. The reaction solution was poured into ice-cold water, and the solution was extracted with ethyl acetate, washed with water, dried and then concentrated under reduced pressure. The residue was crystallized from ethyl ether, and collected by filtration to obtain 3.23 g of 46 (yield 81.9%).

Compound 46: NMR(CDCl$_3$) δ: 1.48(9H,s), 6.44(2H,s), 6.51(1H,bs), 7.43(2H,d,J=6.2 Hz), 7.50(1H,d,J=2 Hz), 7.58

(1H,d,J=2 Hz), 7.76 (1H,bs), 8.56(2H,d,J=6.2H), 8.60(1H, bs) IR(Nujol) v cm$^{-1}$:3574, 3398, 1735, 1631, 1595

(2) To a solution of cyanamide (210 mg, 5 mmol) in 5 ml of DMF was added sodium hydride (60%) (120 mg, 3 mmol), and the mixture was stirred at room temperature for 30 minutes. After adding 46 (394 mg, 1 mmol), the mixture was stirred at room temperature for 7 hours. To the reaction solution was added 0.5 ml of acetic acid, and the solution was concentrated under reduced pressure. To the residue was added ice-cold water. The insoluble materials were collected by filtration, washed with water and ethanol, and dried to obtain 218 mg of 47 (yield 85.7%).

Compound 47: NMR(d$_6$-DMSO) δ: 7.55(2H,d,J=6 Hz), 7.81(1H,s), 7.93(1H,s), 8.50(2H,d,J=6 Hz), 8.64(1H,bs), 9.12(1H,bs) IR(Nujol) v cm$^{-1}$:3420, 3360, 2240, 1690, 1650, 1610 Elemental analysis for $C_{12}H_{10}N_6O \cdot 0.4H_2O$: Calcd: C,55.13; H,4.16; N,32.14 Found: C,55.22; H,4.24; N,31.82

Preparation 14

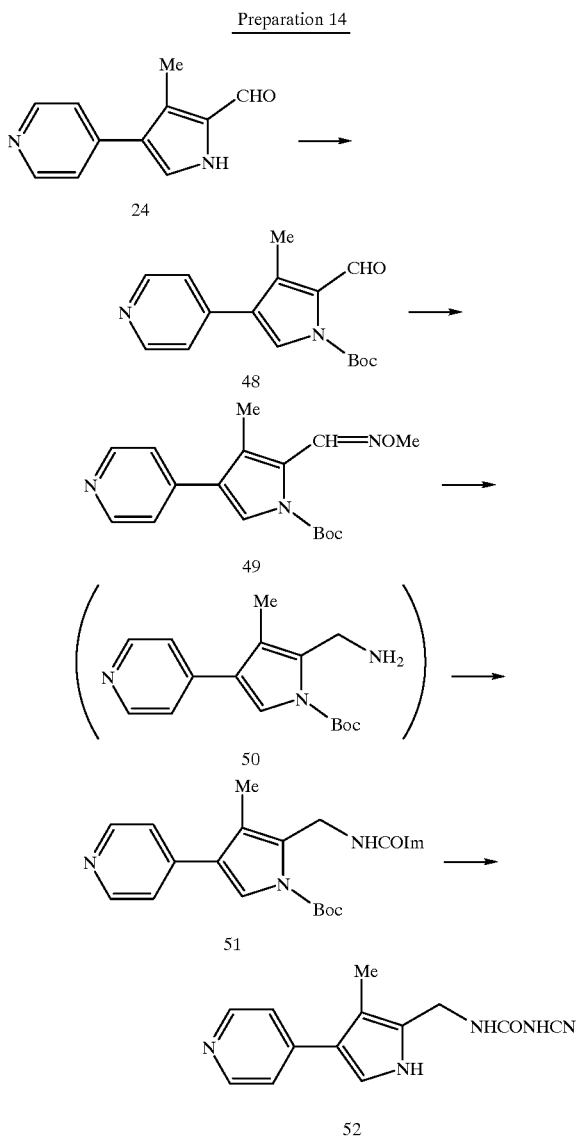

(1) To a solution of 24 (5.61 g, 30.1 mmol) in 140 ml of THF were added (Boc)$_2$O (8.3 ml, 36.1 mmol) and 500 mg of DMA, and the mixture was stirred at room temperature for 30 minutes. The reaction solution was distilled away under reduced pressure. To the residue were added ethyl ether and hexane, and the precipitated crystals were filtered to obtain 8.07 g of a white crystal 48 (yield 95%). m.p. 105–107° C.

Compound 48: NMR(CDCl$_3$) δ: 1.66(9H,s), 2.48(3H,s), 7.30 (2H,d,J=6.2 Hz), 7.52(1H,s), 8.65(2H,d,J=6.2 Hz), 10.47(1H,s) IR(CHCl$_3$) v cm$^{-1}$:1745, 1660, 1604

(2) To a solution of 48 (8.06 g, 28.2 mmol) in 120 ml of methanol were added pyridine (2.73 ml, 33.8 mmol) and MeONH$_2$·HCl (2.47 g, 29.6 mmol) in series, and the mixture was stirred at room temperature for 80 minutes. The reaction solution was distilled away under reduced pressure, and 100 ml of ethyl acetate and 100 ml of H$_2$O were added to separate the ethyl acetate layer. The ethyl acetate layer was washed with water and a saturated saline solution, dried over MgSO$_4$, and then distilled away under reduced pressure to obtain 8.08 g of a white crystal 4(yield 91%). m.p. 104–106° C.

Compound 49: NMR(CDCl$_3$) δ: 1.61(9H,s), 2.34(3H,s), 3.97(3H,s), 7.32(2H,d,J=6.2 Hz), 7.44(1H,s), 8.61(1H,s), 8.61(2H,d,J=6.2 Hz) IR(CHCl$_3$) v cm$^{-1}$:1740, 1604

(3) To a suspension of 6.0 g of zinc powder in 20 ml of acetic acid and 10 ml of ethanol was added a solution of 49 (3.0 g, 9.51 mmol) in acetic acid (15 ml), and the mixture was stirred at room temperature for 30 minutes, and at 35° C. for 30 minutes. The zinc powder was removed by filtration and the mother liquor was concentrated under reduced pressure. Then, CHCl$_3$ and H$_2$O were poured into the residue. The pH of the solution was adjusted to 9 with aqueous ammonia and sodium hydrogencarbonate. The CHCl$_3$ layer was taken, washed with a saturated saline solution, dried over MgSO$_4$ and then distilled away under reduced pressure to obtain a crude product 50. The crude product 50 was dissolved in 90 ml of THF. To the solution was added carbonyldiimidazole (1.54 g, 9.50 mmol), and the mixture was stirred at room temperature for 30 minutes. The resulting reaction solution was poured into water, and extracted twice with ethyl acetate. The ethyl acetate layer was washed with water and a saturated saline solution, dried over MgSO$_4$, and distilled away under reduced pressure. The residue was washed with ethyl ether to obtain 2.65 g of a white powder 51 (yield 73%).

Compound 51: NMR(d$_6$-DMSO) δ: 1.53(9H,s), 2.20(3H, s), 4.65(2H,bs), 7.01(1H,s), 7.49(2H,d,J=6.4 Hz), 7.70(1H, s), 7.73(1H,s), 8.27(1H,s), 8.57(2H,d,J=6.4 Hz)

(4) Compound 51 (2.65 g, 6.95 mmol) was dissolved in 30 ml of DMF. Separately, cyanamide (H$_2$NCN) (321 mg, 7.63 mmol) was dissolved in 20 ml of DMF and NaH (306 g, 7.63 mmol) was added thereto, and the mixture was stirred at room temperature for 10 minutes. The resulting solution was added to the solution of 51 under ice cooling. After stirring at room temperature for 30 minutes, acetic acid (0.88 ml, 15.4 mmol) was added. The solution was distilled away under reduced pressure. To the residue was added H$_2$O. After adding 13.48 ml of 2N HCl, the mixture was stirred under ice cooling. The precipitated insoluble materials were collected by filtration, washed with isopropanol (x2) and ethyl ether (x2) to obtain 965 mg of a yellow powder 52 (yield 54%).

Compound 52: NMR(d$_6$-DMSO) δ: 2.17(3H,s), 4.20(2H, bs), 7.20(1H,bs), 7.37(1H,bs), 7.44(2H,d,J=6.4 Hz), 8.45 (2H,d,J=6.4 Hz), 10.95(1H,bs)

Preparation 15

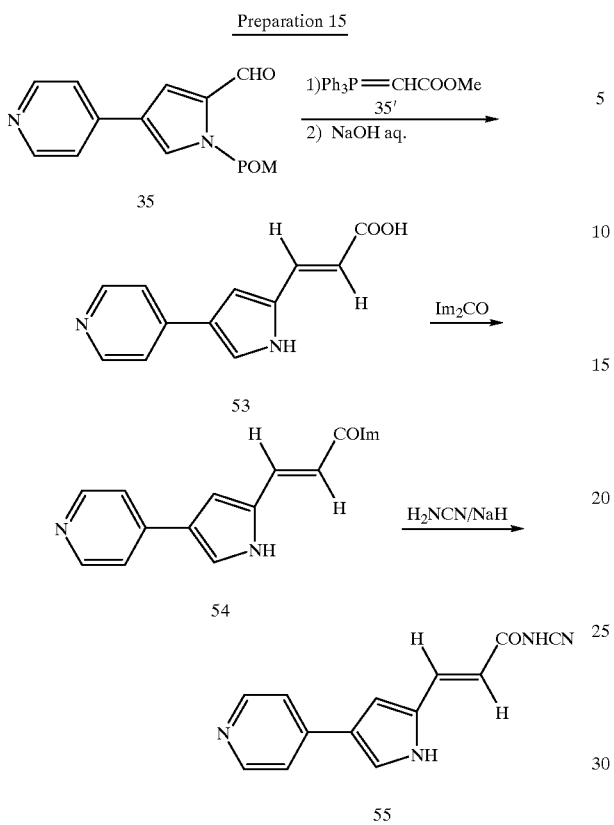

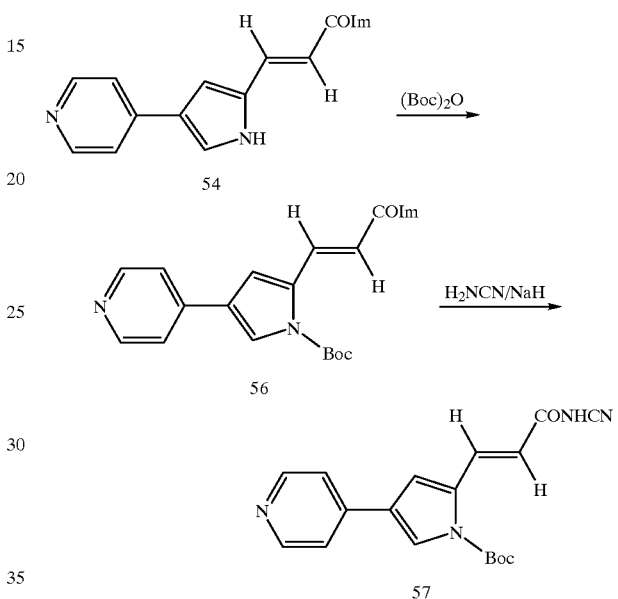

(1) To a solution of 35 (4.30 g, 15.0 mg) in 120 ml of THF was added 35' (6.02 g, 180.0 mg), and then the mixture was refluxed for 2 hours and 20 minutes. The reaction solution was distilled away under reduced pressure, and the residue was dissolved in 80 ml of ethanol. After adding 37.5 ml of 2N NaOH, the mixture was stirred at 50° C. for 1 hour. The resulting solution was adjusted to about pH3 by adding 37.5 ml of 2N HCl, and the solution was concentrated under reduced pressure until methanol was removed. To the concentrated suspension were added 200 ml of ethyl acetate and $H_2O$ (50 ml), and the insoluble materials were filtered off to obtain 2.82 g of a pale yellow crystal 53 (yield 88%). m.p. 272–274° C.

Compound 53: NMR($d_6$-DMSO) δ: 6.22(1H,d,J=16.0 Hz), 7.11(1H,bs), 7.41(1H,d,J=16.0 Hz), 7.58(2H,d,J=5.6 Hz), 7.79(1H,bs), 8.47(2H,bs), 11.91(1H,bs), 12.11(1H,bs) IR(KBr) ν $cm^{-1}$:3431, 1670, 1609

(2) To a suspension of 53 (2.82 g, 13.2 mmol) in 50 ml of DMF was added carbonyldiimidazole (3.03 g, 15.8 mmol), and the mixture was stirred at room temperature for 45 minutes.

The reaction solution was distilled away under reduced pressure and the residue was washed with $H_2O$ to obtain 3.19 g of a yellow crystal 54 (yield 92%). m.p. 213–215° C.

Compound 54: NMR($d_6$-DMSO) δ: 7.17(1H,bs), 7.33 (1H,d,J=15.6 Hz), 7.43(1H,bs), 7.59(2H,d,J=4.8 Hz), 7.81 (1H,bs), 7.84(1H,d,J=15.6 Hz), 8.00(1H,bs), 8.51(1H,bs), 8.52(2H,d,J=4.8 Hz), 12.13(1H,bs) IR(KBr) ν $cm^{-1}$:1708, 1692, 1618, 1602

(3) Compound 54 (1.90 g, 7.19 mmol) was dissolved in 50 ml of DMF. Separately, $H_2NCN$ (332 mg, 7.90 mmol) was dissolved in 30 ml of DMF, and NaH (316 mg, 7.90 mmol) was added thereto, and the mixture was stirred at room temperature for 10 minutes. To the resulting solution was added the solution of 54 under ice cooling, and the mixture was stirred at room temperature for 20 minutes. To the resulting reaction solution was added acetic acid (0.91 ml, 15.8 mmol), and the mixture was distilled away under reduced pressure. To the residue was added $H_2O$ and 3.60 ml of 2N HCl in series. The precipitated insoluble materials were filtered off to obtain 1.74 g of a yellow crystal 55 (yield 100%). m.p. ≧300° C.

Compound 55: NMR($d_6$-DMSO) δ: 6.30(1H,d,J=15.6 Hz), 7.18(1H,bs), 7.46(1H,d,J=15.6 Hz), 7.69(2H,d,J=6.4 Hz), 7.89(1H,bs), 8.51(2H,d,J=6.4 Hz) IR(Nujol) ν $cm^{-1}$:2164, 1626

(4) To a suspension of 54 (3.19 g, 12.1 mmol) in 50 ml of DMF were added $Boc_2O$ (3.33 ml, 14.5 mmol) and 4-dimethylaminopyridine (147 mg, 1.20 mmol), and the mixture was stirred at room temperature for 30 minutes. The resulting solution was distilled away under reduced pressure and the residue was washed with ethyl ether to obtain 3.98 g of a pale yellow crystal 56 (yield 90%). m.p. 172–175° C.

Compound 56: NMR($d_6$-DMSO) δ: 1.65(9H,s), 7.17(1H, bs), 7.54(1H,d,J=15.2 Hz), 7.72(2H,d,J=6.2 Hz), 7.91(1H, bs), 7.97(1H,bs), 8.28(1H,bs), 8.57(1H,d,J=15.2 Hz), 8.61 (2H,d,J=6.2 Hz), 8.68(1H,bs) IR(KBr) ν $cm^{-1}$:1748, 1696, 1602

(5) Compound 56 (3.98 g, 10.9 mmol) was dissolved in 80 ml of DMF and the solution was cooled to −20° C.

Separately, $H_2NCN$ (551 mg, 13.1 mmol) was dissolved in 30 ml of DMF, and NaH (439 mg, 10.9 mmol) was added thereto, and the mixture was stirred at room temperature for 10 minutes. The resultant solution was ice-cooled and added to the solution of 56, and the mixture was stirred at −20° C. for 1 hour and 30 minutes. To the resulting solution was added 10.9 ml of 2N HCl and the mixture was distilled away under reduced pressure. To the residue was added $H_2O$, and $NaHCO_3$ (917 mg, 10.9 mmol) was added to the mixture. The insoluble materials were collected by filtration, and washed with ethyl ether to obtain 3.31 g of a yellow crystal 57 (yield 93%). m.p. 230–235° C.

Compound 57: NMR($d_6$-DMSO) δ: 1.62(9H,s), 6.46(1H, d,J=16.2 Hz), 7.59(1H,bs), 7.85(2H,bs), 8.21(1H,d,J=16.2 Hz), 8.24(1H,bs), 8.60(2H,bs) IR(Nujol) ν $cm^{-1}$:2148, 1746, 1631

Preparation 16

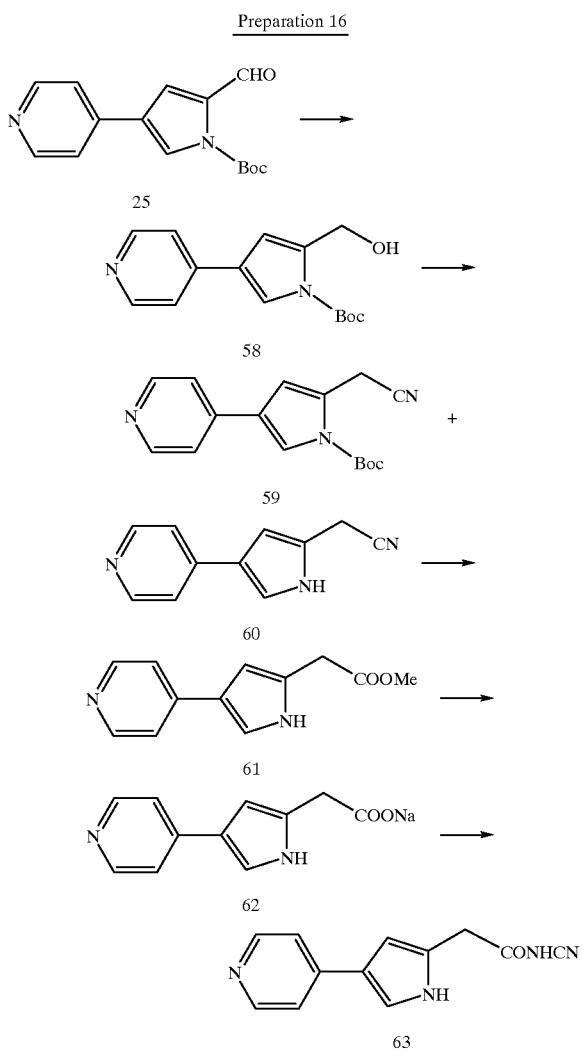

(1) To a solution of 25 (20.90 g, 76.8 mmol) in 360 ml of ethanol was added NaBH4 (2.91 g, 76.8 mmol) at −25° C. After stirring at the same temperature for 1 hour, the pH was adjusted to about 7 by adding 1N HCl. The reaction solution was poured into 500 ml of H$_2$O and the solution was extracted twice with ethyl acetate. Then, the ethyl acetate layer was washed with water and a saturated saline solution, dried over MgSO$_4$, and distilled away under reduced pressure. The resulting reside was washed with ethyl ether to obtain 18.3 g of 58 as a white crystal (yield 87%). m.p. 125–128° C.

Compound 58: NMR(d$_6$-DMSO) δ: 1.59(9H,s), 4.65(2H, d,J=5.6 Hz), 5.15(1H,t,J=5.6 Hz), 6.75(1H,d,J=2.0 Hz), 7.63 (2H,d,J=6.0 Hz), 7.91(1H,d,J=2.0 Hz), 8.50(2H,d,J=6.0 Hz) IR(CHCl$_3$) ν cm$^{-1}$:3532, 1731, 1605

(2) To a suspension of 58 (18.30 g, 66.7 mmol) in 90 ml of DMF was added SOCl$_2$ (7.26 ml, 100 mmol) under ice cooling, and the mixture was stirred at room temperature for 1 hour and 30 minutes. The resulting suspension was diluted with ethyl ether. The insoluble materials were collected by filtration and dissolved in 180 ml of DMF. To the solution were added K$_2$CO$_3$ (36.9 g, 267 mmol), H$_2$O (30 ml), a solution of KCN (8.7 g, 133 moles) in H$_2$O (15 ml) and tetrabutylammonium bromide (2.15 g, 6.7 mmol) under ice cooling, and the mixture was stirred at the same temperature for 24 hours. The reaction solution was poured into H$_2$O (600 ml) and extracted twice with ethyl acetate. The ethyl acetate layer was washed with water and a saturated saline solution, dried over MgSO$_4$ and distilled away under reduced pressure. The resulting residue was treated by silica gel chromatography (toluene/ethyl acetate (2/1 to 1/3)) to obtain 6.83 g of a white crystal 59 (yield 36%) and 3.36 g of a white crystal 60 (yield 27%). The above product 59 (6.82 g, 24.07 mmol) and 60 (2.59 g, 14.13 mmol) were combined, and dissolved in 170 ml of 2.96N HCl/methanol. The solution was refluxed for 24 hours. The resulting solution was distilled away under reduced pressure and the pH was adjusted to about 8 by adding H$_2$O (200 ml) and NaHCO$_3$. The solution was extracted twice with ethyl acetate. The EtOAc layer was washed with water and a saturated saline solution, dried over MgSO$_4$ and distilled away under reduced pressure. The resulting residue was washed with ethyl ether to obtain 6.33 g of a white powder 61 (yield 77%).

Compound 59 m.p.126–129° C. NMR(d$_6$-DMSO) δ: 1.62 (9H,s), 4.21 (2H,s), 6.87(1H,d,J=2.0 Hz), 7.65(2H,d,J=6.2 Hz), 8.03(1H,d,J=2.0 Hz), 8.52(2H,d,J=6.2 Hz) IR(KBr) ν cm$^{-1}$:2255, 2203, 1739, 1603

Compound 60 m.p.168–172° C. NMR(d$_6$-DMSO) δ: 3.98 (2H,s), 6.52(1H,bs), 7.47(1H,s), 7.48(2H,d,J=6.2 Hz), 8.41 (2H,d,J=6.2 Hz) IR(KBr) ν cm$^{-1}$:2258, 1604

Compound 61 m.p.147–150° C. NMR(d$_6$-DMSO) δ: 3.64 (3H,s), 3.66(2H,s), 6.41 (1H,bs), 7.40(1H,bs), 7.46(2H,d,J= 6.0 Hz), 8.39(2H,d,J=6.0 Hz), 11.13(1H,bs) IR(KBr) ν cm$^{-1}$:3446, 1731, 1602

(3) To a suspension of 61 (6.33 g, 29.27 mmol) in 60 ml of methanol was added 17.6 ml of 2N NaOH. After stirring at room temperature for 30 minutes, the precipitated insoluble materials were filtered off to obtain 5.59 g of a white powder 62 (yield 85%). m.p. ≧300° C.

Compound 62 NMR(D$_2$O) δ: 3.54 (2H,s), 6.46(1H,bs), 7.38(1H,bs), 7.55(2H,d,J=4.6 Hz), 8.36(2H,d,J=4.6 Hz) IR(KBr) ν cm$^{-1}$:1638, 1609, 1571

(4) Compound 62 (1.0 g, 4.46 mmol) was suspended in H$_2$O (20 ml). The suspension was neutralized with 1N HCl (4.46 ml) and distilled away under reduced pressure. The resulting residue was suspended in 20 ml of DMF, and carbonyldiimidazole (868 mg, 5.35 mmol) was added thereto under ice cooling, and the mixture was stirred at room temperature for 1 hour. Separately, H$_2$NCN (20 6 mg, 4.91 mmol) was dissolved in 15 ml of DMF, and NaH (196 mg, 4.91 mmol) was added thereto, and the mixture was stirred at room temperature for 10 minutes. The resulting solution was added to the above solution under ice cooling, and the mixture was stirred at room temperature for 1 hour. To the resulting solution was added 4.91 ml of 1N HCl was added. Then, the solution was adjusted to about pH 7 with acetic acid and distilled away under reduced pressure. To the residue was added H$_2$O, and the precipitated insoluble materials were filtered to obtain 663 mg of 63 as a deep green crystal (yield 66%). m.p. 228–230° C.

Compound 63: NMR(d$_6$-DMSO) δ: 3.49(2H,s), 7.46(1H, bs), 7.60(1H,bs), 7.71(2H,d,J=6.0 Hz), 8.47(2H,d,J=6.0 Hz) IR(Nujol) ν cm$^{-1}$:2138, 1631

Preparation 17

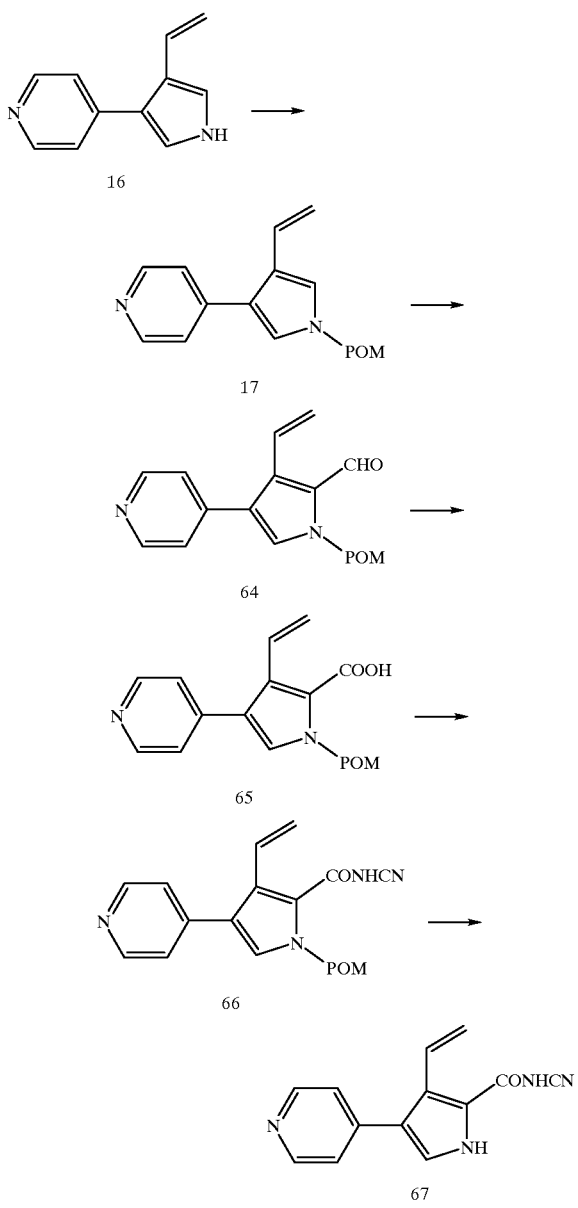

(1) To 16 (3.32 g, 19.5 mmol)/DMF (33 ml) was added 60% NaH (0.86 g, 1.1 eq.), and the mixture was stirred at room temperature for 20 minutes. After cooling the mixture to −30° C., Cl—CH$_2$OCOBu$^t$ (3.0 ml, 1.06 eq.) was added. The mixture was stirred at −10 to 0° C. for 1 hour, poured into ice-cold water, extracted with ethyl acetate, and washed with H$_2$O and a saturated saline solution. The residue was purified by silica gel chromatography to obtain 17 (oily, 5.96 g, 21.9 mmol, yield: 112%).

Compound 17: NMR(CDCl$_3$) δ: 1.196(9H,s), 5.10(1H, dd,J=1.8,10.8 Hz), 5.45(1H,dd,J=1.8,17.6 Hz), 5.78(2H,s), 6.64(1H,dd,J=10.8,17.6 Hz), 5.78(2H,s), 6.64(1H,dd,J=10.8,17.6 Hz), 7.00(2H,bs), 7.31(2H,dd,J=1.6,4.6 Hz), 8.55 (2H,dd,J=1.6,4.6 Hz) IR(CHCl$_3$) ν cm$^{-1}$:1733, 1602

(2) POCl$_3$ (7.5 ml) was added to DMF (20 ml) at −20° C., and the mixture was stirred at 0° C. for 20 minutes. To the solution was added 17 (5.90 g)/DMF (30 ml), and the mixture was heated at 55° C. for 1.5 hours. The mixture was poured into ice-cold water. The solution was neutralized with K$_2$CO$_3$ and extracted with ethyl acetate. The residue was crystallized from toluene to obtain 4.57 g of 64 (yield 78% from 16). m.p. 148–152° C.

Compound 64: NMR(d$_6$-DMSO) δ: 1.15(9H,s), 5.94(2H, s), 6.45(1H,dd,J=7.8,15.6 Hz), 7.40(2H,dd,J=1.6,4.6 Hz), 7.43(1H,d,J=2.2 Hz), 7.65(1H,d,J=15.6), 7.81(1H,d,J=2.2 Hz), 8.58(2H,dd,J=1.6,4.6 Hz), 9.54(1H,d,J=7.8 Hz) IR(Nujol) ν cm$^{-1}$; 3020, 1717, 1649, 1598, 1519, 1413, 1283, 1208, 1131, 960

(3) To a solution of NaClO$_2$ (1.49 g)/NH$_2$SO$_3$H (1.60 g)/H$_2$O (35 ml) was added 64 (2.24 g)/methanol (22 ml) at 5° C. The mixture was stirred at 5 to 10° C. for 40 minutes. After adding Na$_2$SO$_4$ (4.14 g)/H$_2$O (25 ml), the mixture was stirred at 10° C. for 20 minutes, and distilled away under reduced pressure to remove methanol. The solution was extracted with ethyl acetate, washed with water and concentrated. The residue was crystallized from CH$_2$Cl$_2$/toluene to obtain 65 (1.17 g, yield: 49.6%). m.p. 205–207° C.

Compound 65: NMR(d$_6$-DMSO) δ: 1.15(9H,s), 5.91(2H, s), 6.14(1H,d,J=15.6 Hz), 7.27–7.40(3H,m), 7.51(1H,d,J= 15.6 Hz), 7.67(1H,d,J=2 Hz), 8.57(2H,s,J=5.8 Hz) IR(Nujol) ν cm$^{-1}$;3100, 2446, 1746, 1686, 1604, 1399, 1279, 1267, 1109, 972

(4) Carbonyldiimidazole (0.67 g) was added to 65 (1.00 g)/DMF at room temperature, and the mixture was stirred at room temperature for 1 hour. After adding a solution of H$_2$NCN (212 mg)/60% NaH 8177 mg)/DMF (15 ml), the mixture was stirred at room temperature for 2 hours, and at 40° C. for 1 hour. After adding acetic acid (0.29 ml), the mixture was concentrated under reduced pressure until the volume becomes about 5 ml and dissolved in H$_2$O (50 ml). To the mixture were added ethyl acetate (10 ml) and hexane (10 ml). When acetic acid was added to neutralize the aqueous layer, crystals were precipitated. The crystals were collected by filtration, washed with H$_2$O, and ethyl acetate to obtain 0.91 g of 66 as a crude crystal (yield 84.7%). m.p. 192–193° C.

Compound 66: NMR(d$_6$-DMSO) δ: 1.14(9H,s), 5.94(2H, s), 6.23(1H,d,J=15.6 Hz), 7.32–7.45(3H,m), 7.61(1H,d,J= 15.6 Hz), 7.68(1H,d,J=1.8 Hz), 8.61(1H,bs) IR(Nujol) ν cm$^{-1}$;3108, 2224, 1742, 1687, 1373, 1174, 1120, 978

(5) To a suspension of 66 (830 mg, 2.35 mmol) in 20 ml of methanol was added aqueous 2N NaOH (6 ml, 12 mmol) at room temperature, and the mixture was stirred at room temperature for 3 hour. After adding 16 ml of 2N HCl under ice cooling, methanol was distilled away under reduced pressure. The precipitated solids were then collected by filtration and washed in turn with H$_2$O and ethyl ether. The solid materials were filtered, and dried to obtain 530 mg of a yellow powder 67 (yield 95%).

Compound 67: NMR(d$_6$-DMSO) δ: 11.79(1H, m), 8.58 (2H, m), 7.69(1H,d,J=15.6 Hz), 7.54(1H,s), 7.40(2H,d,J=5.7 Hz), 7.27(1H,s), 6.21(2H,d,J=15.6 Hz) IR(Nujol) ν cm$^{-1}$:3350, 3192, 2170, 1626, 1528, 1349, 1066

Preparation 18

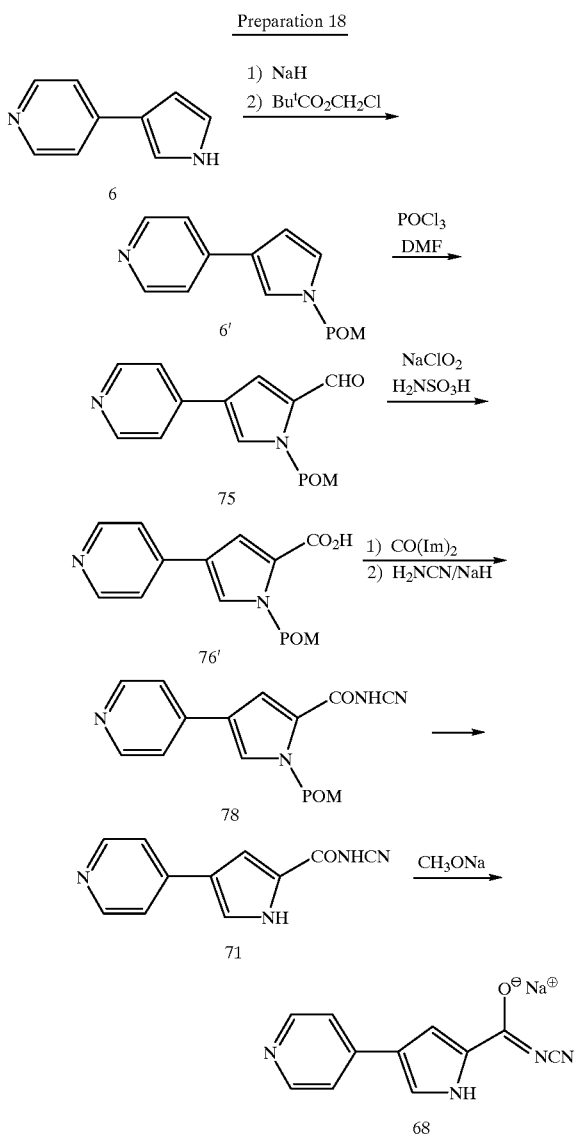

(1) To a suspension of 6 (50 g, 346.8 mmol) in 500 ml of anhydrous DMF was added 60% NaH (15.2 g, 381.5 mmol) under ice cooling and under $N_2$ gas flow, and the mixture was stirred at room temperature for 20 minutes. After cooling to −30° C., $Bu^tCO_2CH_2Cl$ (53 ml, 367.6 mmol) was slowly added dropwise over 35 minutes, and the mixture was stirred at −10° C. for 2 hours. The reaction solution was poured into 2.4 L of ice-cold water, and extracted with 2L of ethyl acetate. The organic layer was washed in turn with water and a saturated saline solution, dried over $MgSO_4$ and concentrated under reduced pressure. Then, the precipitated crystals were collected by filtration, washed with cyclohexane, and dried to obtain 83.24 g of a white crystal 6' (yield 93%). m.p. 96–99° C.

Compound 6': NMR(CDCl$_3$) δ: 8.51(2H,dd,J=4.6,1.6 Hz), 7.37(2H,dd,J=4.6,1.6 Hz), 7.28(1H,m), 6.89(1H,dd,J=2.8,2.2 Hz), 6.55(1H,dd,J=2.8,1.8 Hz), 5.82(2H,s), 1.18(9H,s) IR(Nujol) ν cm$^{-1}$:1723, 1597, 1132

(2) Anhydrous DMF (372 ml, 4.8 moles) was cooled to −20° C. under $N_2$ gas flow, and $POCl_3$ (120 ml, 1.282 moles) was added dropwise over 40 minutes. To the mixture was added a raw material 6' (82.8 g, 320.5 moles), and the mixture was heated to 60° C., and stirred for 3 hours. After cooling to room temperature, the reaction solution was poured into ice-cold water (2L). The solution was adjusted to pH 8 by adding $K_2CO_3$ (266 g, 1.923 moles) with stirring. The precipitated solid materials were collected by filtration and dissolved in 2.2 L of methyl ethyl ketone. The solution was dried over $MgSO_4$ and concentrated under reduced pressure. The residue was recrystallized from toluene to obtain 65.69 g of a flesh crystal 75 (yield 72%). m.p. 183–186° C.

Compound 75: NMR(CDCl$_3$) δ: 9.69(1H,d,J=1.0 Hz), 8.59(2H,dd,J=4.5,1.7 Hz), 7.60(1H,m), 7.40(2H,dd,J=4.6 Hz,1.6 Hz), 7.32(1H,d,J=2.0 Hz), 6.28(2H,s), 1.17(9H,s) IR(Nujol) ν cm$^{-1}$:1718, 1655, 1600, 1426, 1141

(3) To a solution of $NaClO_2$ (18.16 g, 200.8 mmol) and $H_2NSO_3H$ (19.50 g, 200.8 mmol) in 1636 ml of $H_2O$ was added dropwise a solution of 75 (23 g, 80.334 moles) in methanol (400 ml), and the mixture was stirred under ice cooling for 3 hours. After adding dropwise 250 ml of an aqueous $Na_2SO_3$ (50.62 g, 401.6 mmol) under ice cooling, the mixture was stirred for additional 30 minutes and distilled under reduced pressure to remove methanol. The precipitated solids were collected by filtration and dried to obtain 21.14 g of a green powder 76' (yield 21.14%). m.p. 241.5–243° C.

Compound 76': NMR(d$_6$-DMSO) δ: 12.79(1H,bs), 8.50 (2H,dd, J=4.6,1.5 Hz), 7.99(1H,d,J=2 Hz), 7.61(2H,dd,J= 4.6,1.6 Hz), 7.47(1H,d,J=2.0 Hz), 6.21(2H,s), 1.11(9H,s) IR(Nujol) ν cm$^{-1}$:1734, 1686, 1610, 1195, 1129

(4) To a solution of $NH_2CN$ (12.965 g, 308 mmol) in 130 ml of DMF was added NaH (11.719 g, 292.98 mmol) under ice cooling and under nitrogen gas flow. After the completion of the addition, the reaction solution was cooled to room temperature and stirred until the evolution of a hydrogen gas is nearly terminated.

To a solution of 76' (46.62 g, 154.2 mmol) in 470 ml of DMF was added carbonyldiimidazole (32.51 g, 200 mmol) at room temperature, and the mixture was stirred for 1 hour. After ice cooling, the previously prepared Na$^+$[NH-CN]$^-$/ DMF solution was added dropwise. The solution was cooled to room temperature and stirred for 1 hour. After adjusting the pH of the solution to about 7 by adding 5N HCl under ice cooling, DMF was concentrated under reduced pressure. To the resultant residue was added 900 ml of ice-cold water. The precipitated solids were collected by filtration, washed in turn with $H_2O$ and ethyl ether, and dried to obtain 50 g of a yellowish green powder 78 (yield 99%). m.p. 253–256° C.

Compound 78: NMR(d$_6$-DMSO) δ: 8.64(2H,d,J=6.6 Hz), 8.09(1H,d,J=1.8 Hz), 7.96(2H,d,J=6.6 Hz), 7.43(1H,d,J=1.8 Hz), 6.32(2H,s), 1.11(9H,s) IR(Nujol) ν cm$^{-1}$:2184, 2142, 1711, 1634, 1565, 1226, 1155

(5) To a mixture of 78 (50.2 g, 154 mmol) in 1 L of methanol was added dropwise 2N NaOH (385 ml, 770 ml) at room temperature. After stirring at room temperature for 1 hour, the solution was adjusted to pH 7 by adding 385 ml of 2N HCl under ice cooling, and methanol was distilled away under reduced pressure. The precipitated solids were collected by filtration, washed in turn with $H_2O$, isopropanol and ethyl ether, and dried to obtain 32 g of a white powder 71 (yield 100%). m.p. 268–270° C. (decomposition).

Compound 71: NMR(d$_6$-DMSO) δ: 12.2(1H,m), 8.58 (2H,d,J=6.2 Hz), 7.96(2H,d,J=6.8 Hz), 7.88(1H,m), 7.29 (1H,s) IR(Nujol) ν cm$^{-1}$: 3320, 3186, 3066, 2624, 2144, 1633, 1570, 1527, 1407, 1336, 1215, 1200

(6) To a suspension of 71 (32 g, 150 mmol) in 60 ml of anhydrous methanol was added dropwise a solution of 1.14M CH$_3$ONa/methanol (135 ml, 150 mmol) under ice cooling and under a nitrogen gas flow, and the mixture was stirred under ice cooling for 10 minutes. After adding 350 ml of isopropanol, methanol was distilled away under reduced pressure. The precipitated solids were collected by filtration, washed in turn with isopropanol and ethyl ether, and dried to obtain 35.6 g of a pale yellow powder 68 (yield 99%).

Compound 68: NMR($d_6$-DMSO) δ: 11.44(1H,m), 8.39 (2H,d,J=5.8 Hz), 7.53(2H,d,J=6.0 Hz), 7.39(1H,m), 6.91 (1H,m) IR(Nujol) ν $cm^{-1}$:3324, 2714, 2154, 1609, 1576, 1507, 1219, 1146, 1131

Preparation 19

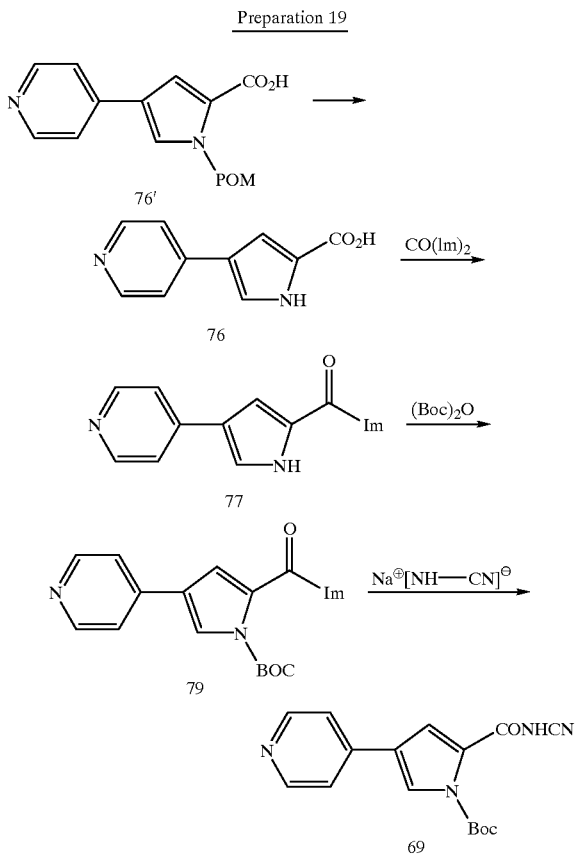

(1) To a suspension of 76' (5.5 g, 18.19 mmol) in 110 ml of methanol was added dropwise aqueous 2N NaOH (45 ml, 90 mmol) at room temperature, and the mixture was stirred at room temperature for 90 minutes. After adding 2N HCl (45 ml, 90 mmol) under ice cooling, methanol was distilled away under reduced pressure. The precipitated solids were collected by filtration, washed in turn with $H_2O$ and ethyl ether, and dried to obtain 3.26 g of a pale green crystal 76 (yield 95%). m.p. ≧300° C.

Compound 76: NMR($d_6$-DMSO) δ: 12.15(1H,bs), 8.45 (2H,m), 7.72(1H,m), 7.62(2H,d,J=5.70 Hz), 7.29(1H,m), IR(Nujol) ν $cm^{-1}$:1629, 1561, 1529, 1210

(2) To a solution of 76 (3.25 g, 17.28 mmol) in 40 ml of anhydrous DMF was added carbonyldiimidazole (5.60 g, 34.56 mmol) at room temperature under $N_2$ gas flow, and the mixture was stirred for 2.5 hours. DMF was distilled away under reduced pressure. To the residue was added 100 ml of ice-cold water to precipitate solid materials. The solids were collected by filtration, washed in turn with $H_2O$, isopropanol and ethyl ether, and dried to obtain 3.7 g of a pale yellow powder 77 (yield 90%). m.p. ≧300° C.

Compound 77: NMR($d_6$-DMSO) δ: 12.81 Hz(1H,bs), 8.49~8.54(3H,m), 8.08(1H,s), 7.89(1H,s), 7.75~7.78(3H, m), 7.18(1H,s) IR(Nujol) ν $cm^{-1}$:1662, 1599, 1219

(3) Compound 77 (3.65 g, 15.32 mmol) was added to 70 ml of anhydrous DMF. To the mixture was added dropwise $(Boc)_2O$ (7 ml, 30.64 mmol) at room temperature under $N_2$ gas flow. After adding a very small amount of 4-dimethylaminopyridine, the mixture was stirred at room temperature for 70 minutes. The reaction solution was concentrated under reduced pressure and 200 ml of ethyl ether was added to the resulting residue. The resultant precipitates were collected by filtration, washed with ether and dried to obtain 4.48 g of a pale yellow powder 79 (yield 86%). m.p. ≧300° C.

Compound 79: NMR($d_6$-DMSO) δ: 8.57(2H,d,J=5.8 Hz), 8.37(2H,m), 7.78(3H,m), 7.67(1H,s), 7.19(1H,s), 1.43(9H,s) IR(Nujol) ν $cm^{-1}$:1749, 1726, 1603, 1239

(4) $NH_2CN$ (1.557 g, 37.04 mmol) was added to 30 ml of DMF, and 60% NaH (1.235 g, 30.87 mmol) was added thereto under ice cooling and under nitrogen gas flow. The mixture was stirred at room temperature for 15 minutes.

Compound 79 (10.445 g, 30.87 mmol) was added to 140 ml of DMF and cooled to −45° C. To the solution was added dropwise the previously prepared $Na^+[NH\text{-}CN]^-$/DMF solution under $N_2$ gas flow over 15 minutes. After stirring at −30° C. for 90 minutes, 1N HCl (62 ml, 62 mmol) was added under ice cooling and the solution was concentrated under reduced pressure. To the residue was added 400 ml of ice-cold water, and the pH was adjusted to about 7 by adding $NaHCO_3$ (2.59 g, 30.87 mmol). The precipitated solids were collected by filtration, washed in turn with $H_2O$, isopropanol and ethyl ether, and dried to obtain 8.97 g of a pale yellow powder 69 (yield 93%). m.p. 257–260° C. (decomposition).

Compound 69: NMR($d_6$-DMSO) δ: 8.67(2H,d,J=6.0 Hz), 8.28(1H,d,J=1.6 Hz), 8.02(2H,d,J=6.2 Hz), 7.33(1H,d,J=1.6 Hz), 1.56(9H,s) IR(Nujol) ν $cm^{-1}$:2150, 1741, 1675, 1523

Preparation 20

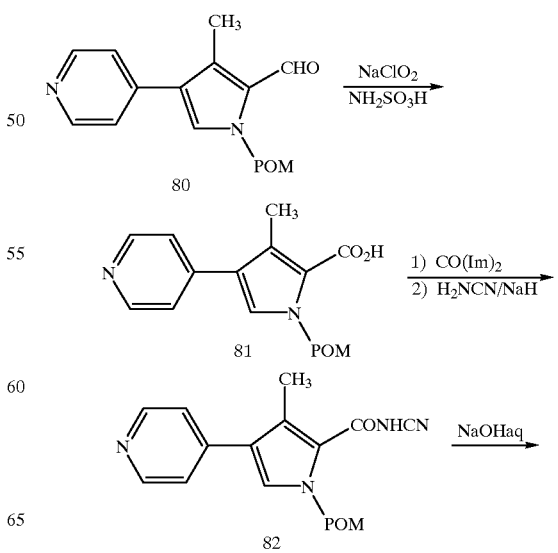

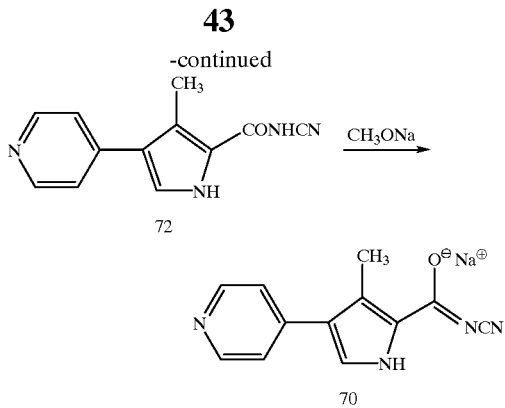

(1) To a solution of NaClO₂ (9.95 g, 110 mmol) and H₂NSO₃H (10.68 g, 110 mmol) in 250 ml of H₂O was added dropwise a solution of 80 (15.0 g, 50 moles) in methanol (150 ml). After stirring under ice cooling for 40 minutes, a solution of Na₂SO₃ (27.7 g, 220 mmol) in H₂O (150 ml) was added dropwise, and the mixture was stirred for additional 20 minutes under ice cooling. The precipitated solids were washed with water and dissolved in methanol (400 ml)/ethyl acetate (300 ml). To the solution was added 200 ml of toluene, and the solution was concentrated under reduced pressure. The precipitated solids were collected by filtration to obtain 10.5 g of a white powder 81 (yield 66.8%). m.p. 211–214° C.

Compound 81: NMR(d₆-DMSO) δ:12.83(1H,bs), 8.56 (2H,dd,J=4.5 Hz,1.5 Hz), 7.62(1H,s), 7.42(2H,m), 6.18(2H, s), 2.42(3H,s), 1.11(9H,s) IR(Nujol) ν cm⁻¹:3136, 2372, 1725, 1677, 1606, 1420, 1260, 1242, 1130, 1112, 1020, 963

(2) To a solution of NH₂CN (723 mg, 17.2 mmol) in 40 ml of anhydrous DMF was added 60% NaH (670 mg, 16.63 mmol), and the solution was stirred for 1 hour at room temperature until evolution of hydrogen gas was terminated.

To a solution of a raw material 81 (3.63 g, 11.47 mmol) in 50 ml of anhydrous DMF was added carbonyldiimidazole (2.23 g, 13.76 mmol) under N₂ gas flow, and the mixture was stirred at room temperature for 1 hour. After ice cooling, the previously prepared Na⁺[NH-CN]⁻/DMF solution was added dropwise, and the mixture was stirred for 5 hours at room temperature. The pH was adjusted to about 7 by adding 2N HCl under ice cooling, and DMF was distilled away under reduced pressure. To the resulting residue was added 300 ml of ice-cold water. The precipitated solids were collected by filtration, washed in turn with H₂O and ethyl ether and dried to obtain 3.9 g of a white powder 82 (yield 99%). m.p. 209–211° C.

Compound 82: NMR(d₆-DMSO) δ: 8.69(2H,d,J=6.2 Hz), 7.88(2H,d,J=6.8 Hz), 7.78(1H,s), 6.26(2H,s), 2.50(3H,s), 1.11 (9H,s)

IR (Nujol) ν cm⁻¹: 2712, 2144, 1710, 1579, 1526, 1459, 1336, 1281, 1255, 1151.

(3) To a suspension of 82 (3.9 g, 11.46 mmol) in 240 ml of methanol was added dropwise aqueous 2N NaOH (30 ml, 15 mmol) at room temperature to completely dissolve the suspension. After stirring at room temperature for 1 hour, the pH of the solution was adjusted to about 7 by adding 130 ml of 2N HCl under ice cooling. Methanol was distilled away under reduced pressure. The precipitated solids were collected by filtration, washed in turn with H₂O, isopropanol and ethyl ether, and dried to obtain 2.19 g of a yellowish white powder 72 (yield 84%). m.p. 226–230° C.

Compound 72: NMR (d₆-DMSO) δ: 11.76 (1H, m), 8.62 (2H, d, J=5.7 Hz), 7.93 (2H, d, J=6.0 Hz), 7.60 (1H, d, J=2.4 Hz), 2.59 (3H, s).

IR (Nujol) ν cm⁻¹: 3162, 2606, 2144, 1631, 1558, 1515, 1454, 1333, 1213, 1153.

(4) To a suspension of 72 (12.63 g, 55.8 mmol) in 335 ml of anhydrous methanol was added dropwise a solution of 1M CH₃ONa/methanol (51.3 ml, 53.0 mmol) under ice cooling and under nitrogen gas flow, and the mixture was stirred at room temperature for 10 minutes. To the mixture was added 335 ml of isopropanol, and then a mixed solution of 100 ml of isopropanol and 100 ml of ethyl ether, and the mixture was stirred at room temperature for a while. The precipitated solids were collected by filtration, washed with ethyl ether, and dried to obtain 13.61 g of a pale yellow powder 70 (yield 99%).

Compound 70: NMR (d₆-DMSO) δ: 11.08 (1H, bs), 8.44 (2H, dd, J=4.5 Hz, 1.5 Hz), 7.39 (2H, dd, J=4.35 Hz, 1.65 Hz), 7.03 (1H, d, J=3.3 Hz), 2.48 (3H, s).

IR (KBr) ν cm⁻¹: 3434, 3375, 2153, 1606, 1563, 1473, 1426, 1413, 1339, 1229, 1145, 835, 811.

Preparation 21

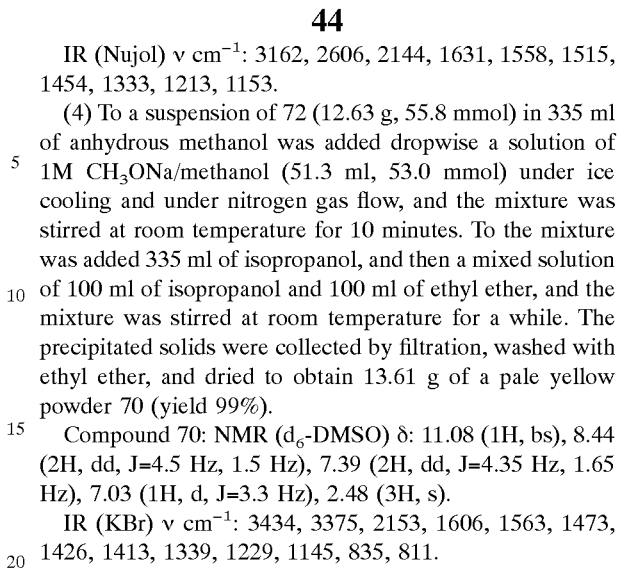

Compound 72 (8.0 g, 35.4 mmol) was added to 190 ml of anhydrous DMF, and (Boc)₂O (34.8 g, 159.3 mmol) was added dropwise thereto at room temperature. After addition of 4-dimethylaminopyridine (0.86 g, 7.08 mmol), the mixture was stirred at room temperature for 45 minutes. The reaction solution was poured into a mixed solution of 400 ml of ethyl acetate and 100 ml of H₂O with stirring under ice cooling. The aqueous layer was taken and concentrated under reduced pressure. The resulting residue was neutralized with diluted hydrochloric acid. The precipitated insoluble materials were filtered off to obtain 4.08 g of 83 (yield 35%).

Compound 83: NMR (d₆-DMSO) δ: 8.65 (2H, m), 7.86 (1H, s), 7.70 (2H, d, J=5.2 Hz), 2.23 (3H, s), 1.54 (9H, s). IR (KBr) ν cm⁻¹: 3104, 2174, 1754, 1639.

Preparation 22

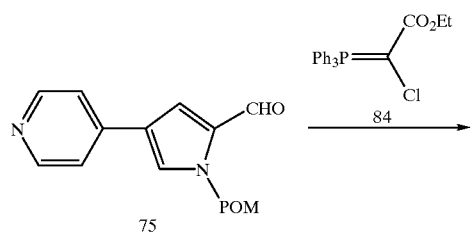

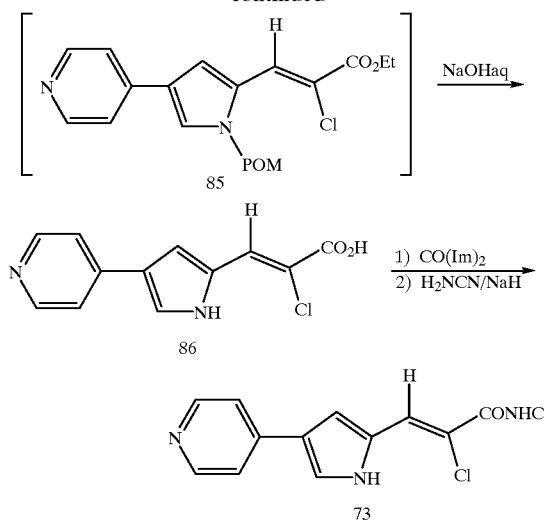

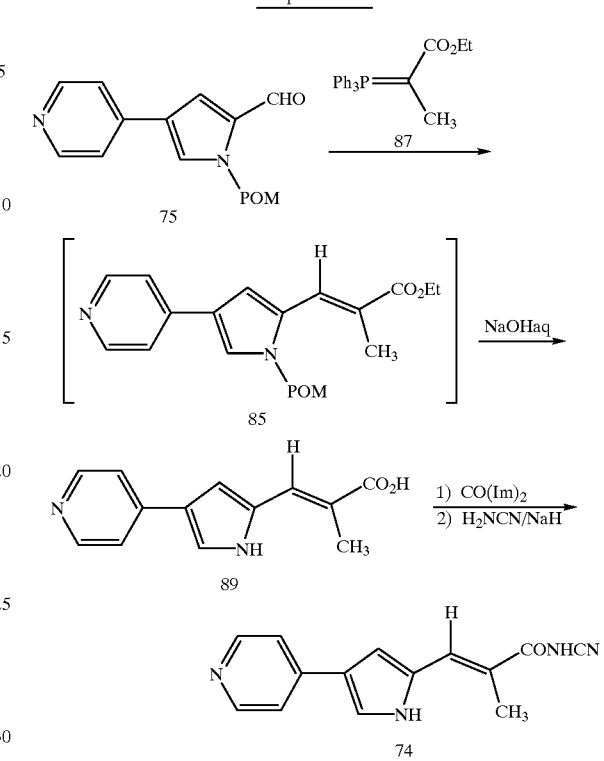

(1) To a solution of 75 (2.86 g, 10 mmol) in 50 ml of anhydrous toluene was added 84 (4.97 g, 13 mmol), and the mixture was heated to reflux in an oil bath at 120° C. for 3.5 hours. Upon cooling to room temperature, crystals were precipitated. The crystals were collected by filtration and washed with hexane to obtain 3.9 g of 85.

To a suspension of 85 in 80 ml of methanol was added 2N NaOH (24 ml, 48 mmol) at room temperature, and the mixture was stirred for 90 minutes. Methanol was distilled away under reduced pressure. The residue was washed twice with 100 ml of toluene. The aqueous layer was taken and adjusted to pH 7 by adding 148 ml of 1N HCl. The precipitated solids were collected by filtration, washed in turn with $H_2O$ and ethyl ether, and dried to obtain 1.20 g of a yellow powder 86 (yield 50%). m.p. ≧300° C.

Compound 86: NMR ($d_6$-DMSO) δ: 11.93 (1H, bs), 8.48 (2H, d, J=5.4 Hz), 7.88 (1H, m), 7.85 (1H, s), 7.63 (2H, d, J=5.8 Hz), 7.53 (1H, s).

IR (Nujol) ν $cm^{-1}$: 2714, 1619, 1530, 1374, 1203, 927.

(2) To a solution of $NH_2CN$ (302 mg, 7.17 mmol) in 6 ml of DMF was added 60% NaH (268 mg, 6.69 mmol) under ice cooling and under nitrogen gas flow, and the mixture was stirred at room temperature for 2.5 hours to obtain a solution of $Na^+[NH—CN]^-$/DMF. To a suspension of 86 (1.19 g, 4.78 mmol) in 15 ml of anhydrous DMF was added carbonyldiimidazole (1.0 g, 6.21 mmol) at room temperature, and the mixture was stirred for 3 hours. To the reaction solution was added dropwise the previously prepared $Na^+[NH—CN]^-$/DMF solution under ice cooling, and the mixture was stirred at room temperature for 90 minutes. The reaction solution was adjusted to about pH 7 by adding acetic acid under ice cooling and concentrated under reduced pressure. To the residue was added 200 ml of ice-cold water. The precipitated solids were collected by filtration, washed in turn with $H_2O$, isopropanol and ethyl ether, and dried to obtain 928 mg of a yellowish green powder 73 (yield 73%). m.p. ≧300° C.

Compound 73: NMR ($d_6$-DMSO) δ: 12.10 (1H, bs), 8.64 (2H, d, J=6.4 Hz), 8.11 (2H, d, J=7 Hz), 8.09 (1H, s), 7.75 (1H, s), 7.52 (1H, s).

IR (Nujol) ν $cm^{-1}$: 2718, 2152, 1627, 1572, 1526, 1374, 1206.

Preparation 23

(1) To a suspension of 75 (2.86 g, 10 mmol) in a mixed solution of 120 ml of toluene and 30 ml of THF was added 25 mmol of 87 at room temperature under nitrogen gas flow, and the mixture was heated to reflux at 100° C. for 8 hours. After cooling to room temperature, the reaction solution was concentrated under reduced pressure to obtain 3.7 g of 88. To a mixture of 88 and 80 ml of methanol was added 2N NaOH (25 ml, 50 mmol) at room temperature, and the mixture was stirred for 3 hours at room temperature. Methanol was distilled away under reduced pressure, and the residue was washed three times with 100 ml of toluene. The aqueous layer was neutralized and adjusted to pH 7 with 2N HCl. The precipitated solids were collected by filtration, washed in turn with $H_2O$ and ethyl ether, and dried to obtain 11.8 g of a yellow powder 89 (yield 52%). m.p. ≧300° C.

Compound 89: NMR ($d_6$-DMSO) δ: 8.68 (2H, d, J=6.4 Hz), 8.26 (2H, d, J=6.8 Hz), 8.17 (1H, s), 7.51 (1H, s), 7.29 (1H, s), 2.13 (3H, s).

IR (Nujol) ν $cm^{-1}$: 1681, 1620, 1571, 1375, 1313, 1198, 1162, 1013.

(2) To a solution of $NH_2CN$ (266 mg, 6.33 mmol) in 10 ml of anhydrous DMF was added 60% NaH (236 mg, 5.91 mmol) under ice cooling, and the mixture was stirred at room temperature for 50 minutes to prepare a solution of $Na^+[NH—CN]^-$/DMF. Compound 89 (963 mg, 4.22 mmol) was added to 15 ml of anhydrous DMF, and carbonyldiimidazole (889 mg, 5.49 mmol) was added thereto under $N_2$ gas flow, and the mixture was stirred at room temperature for 1 hour. To the solution was added dropwise the previously prepared $Na^+[NH—CN]^-$/DMF solution under ice cooling, and the mixture was stirred at room temperature for 2.5 hours. After adding acetic acid (0.72 ml, 12.66 mmol) under ice cooling, the solution was concentrated under reduced pressure. To the residue was added 200 ml of ice-cold water to precipitate. The precipitated solids were then collected by filtration, washed in turn with H₂O, isopropanol and ethyl ether, and dried to obtain 1.05 g of a yellow powder 74 (yield 99%).

Compound 74: NMR (d₆-DMSO) δ: 12.44 (1H, bs), 8.73 (2H, d, J=6.2 Hz), 8.29 (2H, d, J=6.8 Hz), 8.25 (1H, m), 7.40 (2H, s), 2.17 (3H, s).

IR (Nujol) ν cm⁻¹: 3272, 2718, 2240, 2148, 1670, 1596, 1523, 1374, 1323, 1206, 1193, 1015.

Preparation 24

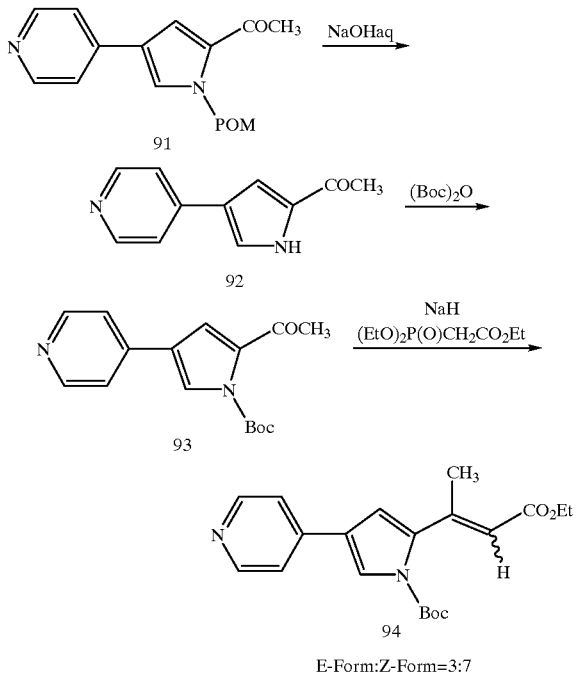

E-Form:Z-Form=3:7

(1) To a suspension of 91 (2.2 g, 7.32 mmol) in 40 ml of methanol was added aqueous 2N NaOH (18 ml, 36 mmol) at room temperature, and the mixture was stirred for 1 hour. After adding dropwise 2N HCl (18 ml, 36 mmol) under ice cooling, methanol was distilled away under reduced pressure. The residue was extracted three times with 50 ml of ethyl acetate. Organic layers were combined and dried over MgSO₄. MgSO₄ was removed by filtration and the filtrate was concentrated under reduced pressure. The precipitated crystals were collected by filtration, washed with ethyl ether, and dried to obtain 1.08 g of a white crystal 92 (yield 79%). m.p. 179–181° C.

Compound 92: NMR (CDCl₃) δ: 9.60 (1H, bs), 8.58 (2H, d, J=5.4 Hz), 7.45 (1H, dd, J=3.15, 1.65 Hz), 7.41 (2H, dd, J=6.3, 3.0 Hz), 7.23 (1H, dd, J=2.55, 1.65 Hz), 2.51 (3H, s).

IR (CHCl₃) ν cm⁻¹: 3438, 3002, 1650, 1602, 1391, 1313, 1273, 943.

(2) Compound 92 (1.08 g, 5.80 mmol) was suspended in 20 ml of anhydrous DMF under nitrogen gas flow. After adding dropwise (Boc)₂O (3.3 ml, 14.5 mmol), 4-dimethylaminopyridine (71 mg, 0.58 mmol) was added to the suspension, and the mixture was stirred at room temperature for 80 minutes. The resulting solution was concentrated under reduced pressure. To the residue was added 60 ml of n-hexane, and the mixture was slowly stirred at room temperature. The precipitated crystals were then collected by filtration, and dried to obtain 1.39 g of a whitish pink crystal 93 (yield 84%). m.p. 113–115° C.

Compound 93: NMR (CDCl₃) δ: 8.60 (2H, d, J=6.0 Hz), 7.71 (1H, d, J=1.8 Hz), 7.39 (2H, dd, J=4.6, 1.6 Hz), 7.15 (1H, d, J=1.8 Hz), 2.52 (3H, s), 1.61 (9H, s).

IR (CHCl₃) ν cm⁻¹: 2982, 1752, 1677, 1604, 1392, 1281, 1237, 1148.

(3) NaH (1.128 g, 28.20 mmol) was added to 30 ml of anhydrous THF. After (EtO)₂P(O)CH₂CO₂Et (5.73 ml, 28.92 mmol) was added dropwise at 25° C., the mixture was stirred at room temperature for 20 minutes. Under ice cooling, a solution of 93 (1.38 g, 4.82 mmol) in anhydrous THF (13 ml) was added dropwise over 10 minutes, and the mixture was stirred at room temperature for 100 minutes. Under ice cooling, 28 ml of 1N HCl was added and the solution was extracted three times with 50 ml of ethyl acetate. The organic layers were combined, washed twice with a saline solution, dried and concentrated. The resulting residue was purified by silica gel column chromatography to obtain 433 mg of a white crystal 94 (E-form) and 1.01 g of an orange oily substance 94 (Z-form), that is, total of 1.444 g (total yield: 84%).

E-form: m.p. 91–93° C.

NMR (CDCl₃) δ: 8.57 (2H, d, J=5.4 Hz), 7.68 (1H, dd, J=1.7, 1.1 Hz), 7.38 (2H, dd, J=4.8 Hz, 1.2 Hz), 6.51 (1H, dd, J=1.9, 0.9 Hz), 5.99 (1H, s), 4.22 (2H, q, J=7.1 Hz), 2.42 (3H, s), 1.60 (9H, s), 1.32 (3H, t, J=7.2 Hz).

IR (CHCl₃) ν cm⁻¹: 2980, 1747, 1705, 1604, 1355, 1287, 1155, 1140.

Z-form:

NMR (CDCl₃) δ: 8.54 (2H, d, J=6.2 Hz), 7.71 (1H, dd, J=2.0, 0.8 Hz), 7.38 (2H, dd, J=4.5, 1.7 Hz), 6.38 (1H, dd, J=1.9, 0.7 Hz), 5.98 (1H, dd, J=1.4, 0.8 Hz), 4.01 (2H, q, J=6.4 Hz), 2.21 (3H, s), 1.57 (9H, s), 1.12 (3H, t, J=7 Hz).

IR (CHCl₃) ν cm⁻¹: 2976, 1743, 1710, 1604, 1370, 1277, 1220.

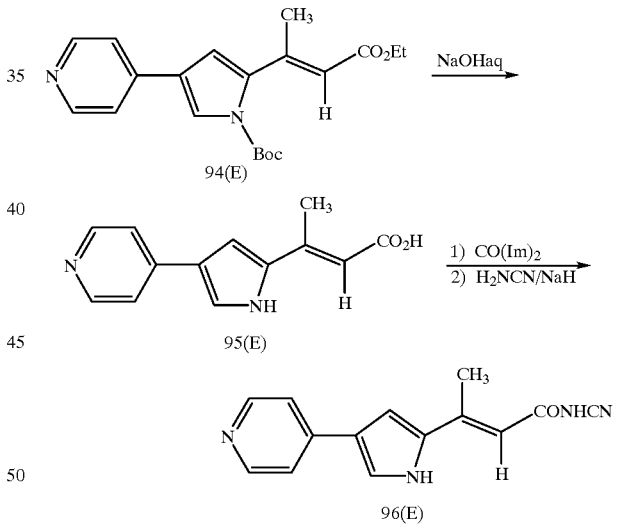

(4) To a solution of 94 (E) (334 mg, 0.94 mmol) in 7 ml of methanol was added dropwise aqueous 1N NaOH (4.7 ml, 4.7 mmol) at room temperature, and the mixture was stirred at 60° C. for 2 hours. Under ice cooling, 14.7 ml of 1N HCl was added and methanol was distilled away under reduced pressure. The precipitated solids were collected by filtration, washed in turn with H₂O and ethyl ether, and dried to obtain 180 mg of a pale yellow powder 95 (E) (yield 94%). m.p. 243–245° C.

Compound 95(E): NMR (d₆-DMSO+D₂O+DCl) δ: 12.35 (1H, bs), 8.66 (2H, d, J=6.9 Hz), 8.20 (2H, d, J=7.2 Hz), 8.12 (1H, d, J=0.9 Hz), 7.40 (1H, s), 6.26 (1H, s), 2.48 (3H, s).

IR (Nujol) ν cm⁻¹: 3242, 1670, 1610, 1570, 1312, 1216, 1160, 1010, 799.

(5) To a solution of NH₂CN (249 mg, 5.92 mmol) in 8 ml of DMF was added 60% NaH (304 mg, 7.6 mmol) under ice cooling, and the mixture was stirred at room temperature for 40 minutes to prepare a solution of Na⁺[NH—CN]⁻/DMF.

To a suspension of 95 (E) (169 mg, 0.74 mmol) in 7 ml of anhydrous DMF was added carbonyldiimidazole (156 mg, 0.96 mmol) at room temperature, and the mixture was stirred at room temperature for 1 hour. To the solution was added dropwise the previously prepared Na⁺[NH—CN]⁻/DMF solution under ice cooling, and the mixture was stirred at room temperature for 6 hours. After adding dropwise acetic acid (0.97 ml, 22.8 mmol) under ice cooling, the solution was concentrated under reduced pressure. To the residue was added 80 ml of ice-cold water, and the mixture was stirred. The precipitated solids were collected by filtration, washed in turn with H₂O, isopropanol and ethyl ether, and dried to obtain 128 mg of a yellow powder 96 (E) (yield 66%). m.p. 217–220° C.

Compound 96(E): NMR (d₆-DMSO+DCl, D₂O) δ: 12.57 (1H, bs), 8.70 (2H, d, J=6.8 Hz), 8.23 (2H, d, J=6.8 Hz), 8.20 (1H, s), 7.49 (1H, d, J=0.4 Hz), 6.28 (1H, s), 2.52 (3H, s).

IR (Nujol) ν cm⁻¹: 2142, 1629, 1537, 1300, 1255, 1202, 930.

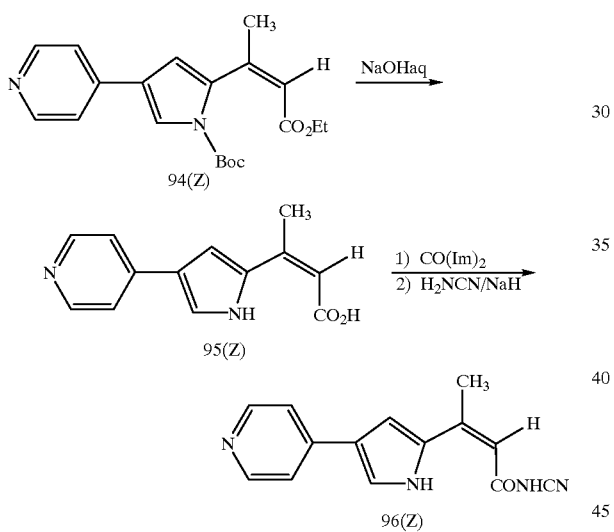

(6) To a solution of 94 (Z) (517 mg, 1.45 mmol) in 11 ml of ethanol was added dropwise aqueous 1N NaOH (7.25 ml, 7.25 mmol) at room temperature, followed by stirring at 60° C. for 45 minutes. Under ice cooling, 17.25 ml of 1N HCl was added, and ethanol was distilled away under reduced pressure. The precipitated solids were collected by filtration, washed in turn with H₂O and ethyl ether, and dried to obtain 250 mg of a pale yellow crystal 9 (Z) (yield 76%). m.p. 153–156° C.

Compound 95(Z): NMR (d₆-DMSO) δ: 13.23 (1H, s), 8.52 (2H, d, J=4.6 Hz), 7.91 (1H, d, J=1.6 Hz), 7.73 (2H, d, J=5.8 Hz), 7.27 (1H, s), 5.69 (1H, d, J=0.8 Hz), 2.29 (3H, s).

IR (Nujol) ν cm⁻¹: 3368, 2156, 1630, 1558, 1507, 1208, 1154, 929.

(7) 60% NaH (76 mg, 1.887 mmol) was added to 2 ml of anhydrous DMF. To the mixture was added NH₂CN (86 mg, 2.04 mmol) under ice cooling and under N₂ gas flow, and the mixture was stirred at room temperature for 90 minutes to prepare a solution of Na⁺[NH—CN]⁻/DMF.

To a suspension of 95 (Z) (233 mg, 1.02 mmol) in 5 ml of anhydrous DMF was added carbonyldiimidazole (255 mg, 1.632 mmol) at room temperature, and the mixture was stirred at room temperature for 105 minutes. To the suspension was added dropwise the previously prepared Na⁺[NH—CN]⁻/DMF solution under ice cooling, and the mixture was stirred at room temperature for 2 hours. After adding dropwise 1N HCl (13.6 ml, 3.6 mmol) under ice cooling, DMF was distilled away under reduced pressure. To the residue was added 100 ml of ice-cold water. The precipitated solids were collected by filtration, washed in turn with H₂O, isopropanol and ethyl ether, and dried to obtain 174 mg of a brown powder 96 (Z) (yield 68%). m.p. 219–221° C.

Compound 96(Z): NMR (d₆-DMSO) δ: 12, 29 (1H, bs), 8.58 (2H, d, J=6.2 Hz), 7.99 (1H, s), 7.96 (2H, d, J=6.2 Hz), 7.19 (1H, s), 5.67 (1H, d, J=0.4 Hz), 2.21 (3H, s).

IR (Nujol) ν cm⁻¹: 2718, 2150, 1607, 1562, 1503, 1283, 1199, 1153.

Preparation 25

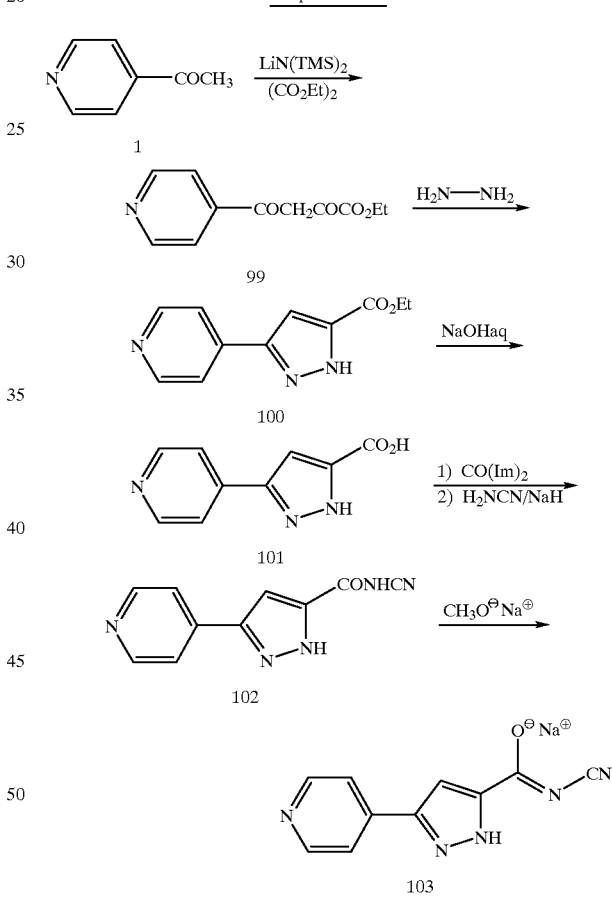

(1) Compound 1 (23.72 ml, 214.4 mmol) was added to 215 ml of THF and the mixture was cooled to −72° C. Under N₂ gas flow, (CO₂Et)₂ (29.12 ml, 214.4 mmol) and a solution of LiN(TMS)₂/THF (1 mole, 214 ml) were added in series, and the mixture was stirred while slowly elevating the temperature up to room temperature. After cooling again to −65° C., 64 ml of 5N HCl was added dropwise, and the mixture was stirred at room temperature for 30 minutes. The reaction solution was concentrated under reduced pressure. To the residue was added 128.7 ml of 1N NaOH. The precipitated crystals were collected by filtration, washed in turn with H₂O and ethyl ether, and dried to obtain 64 g of a yellow crystal 99. After cooling to −30° C., the crystals were dissolved in 126 ml of concentrated HCl and 51.5 ml of H₂O. To the solution was added H₂NNH₂.H₂O (9.0 ml, 185 mmol), and the mixture was stirred at 85° C. for 40 minutes. Then, 130 ml of 1N NaOH was added under ice cooling. The precipitated crystals were collected by filtration, washed in turn with H₂O, isopropanol and ethyl ether, and dried to obtain 27.9 g of a yellow powder 100 (yield 70%). m.p. 215–217° C.

100: NMR (d₆-DMSO) δ: 14.4 (bs, 1H), 8.67 (2H, d, J=6 Hz), 7.95 (2H, d, J=6 Hz), 7.56 (1H, m), 4.35 (2H, q, J=7 Hz), 1.33 (3H, t, J=7.1 Hz).

IR (Nujol) ν cm⁻¹: 1726, 1609, 1572, 1248, 1204.

(2) To a suspension of 100 (2.17 g, 10 mmol) in 40 ml of ethanol was added dropwise 50 ml of 1N NaOH at room temperature, and the mixture was stirred at 60° C. for 2 hours. Under ice cooling, 50 ml of 1N HCl was added. Methanol was distilled away under reduced pressure. The precipitated crystals were collected by filtration, washed in turn with H₂O, THF and ethyl ether, and dried to obtain 1.47 g of a white powder 101 (yield 78%). m.p. ≧300° C.

Compound 101: NMR (d₆-DMSO+DCl) δ: 8.91 (2H, m), 8.50 (2H, d, J=5.8 Hz), 7.80 (1H, s).

IR (Nujol) ν cm⁻¹: 3144, 2454, 2068, 1637, 1598, 1552, 1403, 1375, 1202, 831, 807.

(3) NH₂CN (625 mg, 14.86 mmol) was added to 17 ml of anhydrous DMF. To the mixture was added 60% NaH (565 mg, 14.12 mmol) under ice cooling and under N₂ gas flow, and the mixture was stirred at room temperature for 1 hour to prepare a solution of Na⁺[NH—CN]⁻/DMF. To a suspension of 101 (1.406 g, 7.432 mmol) in 50 ml of anhydrous DMF was added carbonyldiimidazole (2.049 g, 12.63 mmol) at room temperature under N₂ gas flow, and the mixture was stirred for 2 hours. To the suspension was added dropwise the previously prepared Na⁺[NH—CN]⁻/DMF solution under ice cooling, and the mixture was stirred at room temperature for 1 hour. After adding 120 ml of 1N HCl under ice cooling, DMF was distilled away under reduced pressure. To the residue was added 200 ml of ice-cold water. The precipitated solids were collected by filtration, washed in turn with H₂O, isopropanol and ethyl ether, and dried to obtain 1.225 g of a white powder 102 (yield 77%). m.p. ≧300° C.

Compound 102: NMR (d₆-DMSO, DCl) δ: 8.98 (2H, d, J=6 Hz), 8.52 (2H, d, J=6.2 Hz), 7.95 (1H, s).

IR (Nujol) ν cm⁻¹: 2170, 1635, 1573, 1541, 1345, 957.

(4) To a suspension of 102 (479 mg, 2 mmol) in 5 ml of anhydrous methanol was added dropwise a solution of MeONa/methanol (1.1 M, 1.75 ml) under ice cooling and under N₂ gas flow, and the mixture was stirred at 0° C. for 20 minutes. The reaction solution was poured into 50 ml of isopropanol. The solution was concentrated under reduced pressure until methanol was removed. The solids were collected by filtration, washed in turn with isopropanol and ethyl ether, and dried to obtain 420 mg of a white powder 103 (yield 89%).

Compound 103: NMR (D₂O) δ: 8.52 (2H, m), 7.67 (2H, m), 7.06 (1H, s).

IR (Nujol) ν cm⁻¹: 3090, 2150, 1611, 1581, 1562, 1413, 1375, 1340, 988.

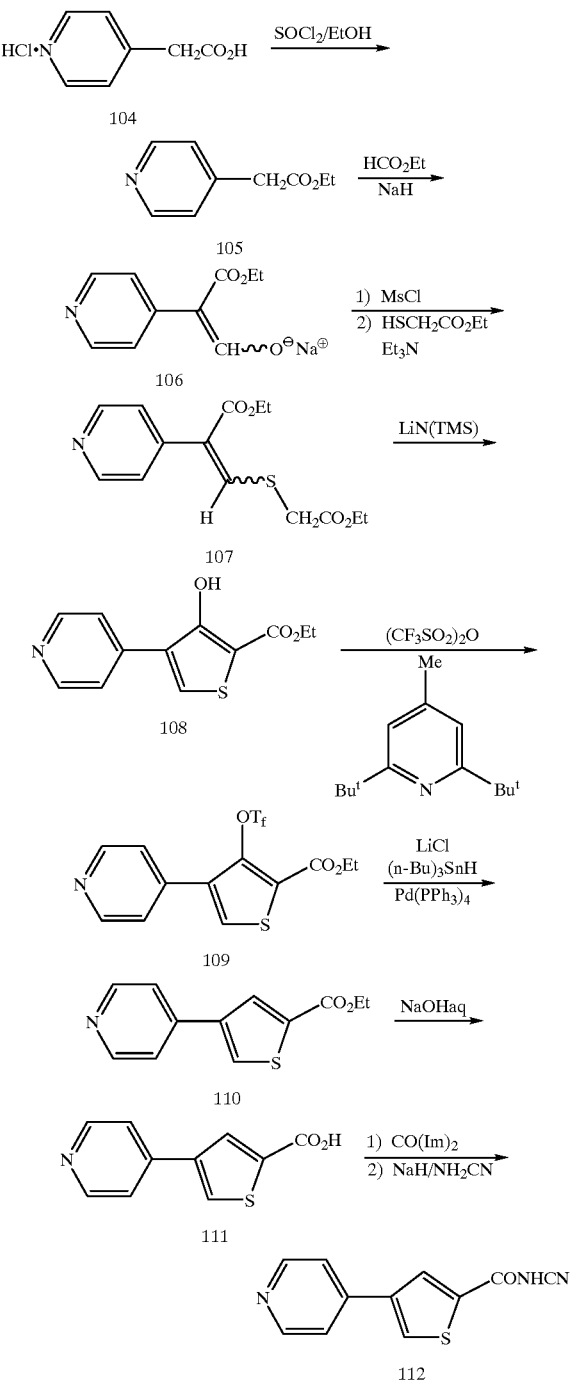

Preparation 26

(1) To a suspension of 104 (48 g, 276.5 mmol) in 500 ml of anhydrous ethanol was added dropwise SOCl₂ (40.34 ml, 553 mmol) over 20 minutes under ice cooling and under N₂ gas flow. After stirring at 50° C. for 70 minutes, the solution was concentrated under reduced pressure. To the residue were added 500 ml of ethyl acetate and 100 ml of H₂O, and the pH of the solution was adjusted to about 7 with Na₂CO₃. The ethyl acetate layer was taken, concentrated under reduced pressure, and purified by distillation under reduced pressure to obtain 44.96 g of 105 (yield 98%).

Compound 105: NMR (CDCl$_3$) δ: 8.57 (2H, dd, J=6.0, 1.5 Hz), 7.25 (2H, d, J=6.0 Hz), 4.18 (2H, q, J=7.2 Hz), 3.62 (2H, s), 1.27 (3H, t, J=7.2 Hz).

(2) Compound 105 (44.83 g, 271.4 mmol) was added to 450 ml of anhydrous THF, and HCO$_2$Et (65.77 ml, 814 mmol) was added to the mixture under N$_2$ gas flow. After adding 60% NaOH (13.03 g, 325.68 mmol), the mixture was stirred at room temperature for 3 hours. To the mixture was added 720 ml of ethyl ether. The resultant precipitates were collected by filtration and dried to obtain 59.39 g of a powder 106.

Compound 106: NMR (D$_2$O) δ: 8.94 (1H, s), 8.36 (2H, d, J=6.2 Hz), 7.43 (2H, d, J=6.2 Hz), 4.16 (2H, q, J=7.0 Hz), 1.25 (3H, t, J=7.3 Hz).

(3) Compound 106 (59.39 g, 276 mmol) was added to 480 ml of anhydrous THF. To the mixture was added dropwise MsCl (21.36 ml, 276 mmol) under ice cooling and under N$_2$ gas flow, and the mixture was stirred for 35 minutes. To the mixture were added dropwise HSCH$_2$CO$_2$ET (30.26 ml, 276 mmol) and Et$_3$N (42.32 ml, 303.6 mmol) in series, and the mixture was stirred under ice cooling for 20 minutes. Then, 600 ml of ethyl acetate and 600 ml of H$_2$O were added. The ethyl acetate layer was taken, washed in turn with H$_2$O and a saturated saline solution, and dried over MgSO$_4$. MgSO$_4$ was removed by filtration, and the filtrate was concentrated under reduced pressure. The resulting residue was subjected to silica gel column chromatography. The fraction eluted with toluene/ethyl acetate (2/1) was concentrated under reduced pressure to obtain 71.11 g of an oily substance 107 (yield 87%).

Compound 107: NMR (CDCl$_3$) δ: 8.64 (2H, dd, J=6.0, 1.6 Hz), 7.98 (1H, s), 7.25 (2H, dd, J=6.0, 1.8 Hz), 4.24 (4H, q, J=7.0 Hz), 3.53 (2H, s), 1.31 (3H, t, J=7.0 Hz), 1.29 (3H, t, J=7.1 Hz).

IR (CHCl$_3$) ν cm$^{-1}$: 2980, 1737, 1700, 1600, 1575, 1365, 1295, 1240, 1180.

(4) Compound 107 (71.11 g, 240.8 mmol) was added to 700 ml of anhydrous THF, and the solution was cooled to −50° C. Under N$_2$ gas flow, a solution (265 ml, 265 mmol) of LiN(TMS)$_2$/THF (1 mole) was added dropwise, and the mixture was stirred at room temperature for 1 hour. Acetic acid (30.33 ml, 529 mmol) was then added, and the solution was concentrated under reduced pressure. To the residue were added 1L of ethyl acetate and 500 ml of H$_2$O. The ethyl acetate layer was taken, washed in turn with H$_2$O and a saturated saline solution, and dried over MgSO$_4$. After removing MgSO$_4$ by filtration, the filtrate was concentrated under reduced pressure. To the residue was added 300 ml of CH$_2$Cl$_2$ and the insoluble materials were removed by filtration. The filtrate was concentrated under reduced pressure to obtain 56.82 g of 108 (yield 95%). m.p. 123–125° C.

Compound 108: NMR (CDCl$_3$) δ: 10.28 (1H, bs), 8.65 (2H, dd, J=6.2, 1.8 Hz), 7.68 (1H, s), 7.67 (2H, dd, J=6.4, 1.6 Hz), 4.42 (2H, q, J=7.0 Hz), 1.41 (3H, t, J=7.2 Hz).

IR (CHCl$_3$) ν cm$^{-1}$: 2980, 1658, 1605, 1570, 1440, 1377, 1328, 1190.

(5) Compound 108 (56.82 g, 228 moles) was dissolved in 1000 ml of anhydrous CH$_2$Cl$_2$ and the solution was cooled to −30° C. Under N$_2$ gas flow, (2,6-di-tert-butyl-4-methylpyridine) (51.50 g, 251 mmol) and (CF$_3$SO$_2$)$_2$O (47.95 ml, 285 mmol) were added dropwise in series, and the mixture was stirred under ice cooling for 50 minutes. The reaction solution was concentrated under reduced pressure. To the residue were added 1000 ml of ethyl acetate and 550 ml of saturated NaHCO$_3$. The ethyl acetate layer was taken, washed in turn with H$_2$O and a saturated saline solution, and dried over MgSO$_4$. MgSO$_4$ was removed by filtration and the filtrate was concentrated under reduced pressure, and subjected to silica gel column chromatography. The fraction eluted with toluene/ethyl acetate (4/1) was concentrated under reduced pressure to obtain 67.32 g of 109 (yield 77%). m.p. 100–101° C.

Compound 109: NMR (CDCl$_3$) δ:8.72 (2H, dd, J=6.0, 1.4 Hz), 7.64 (1H, s), 7.39 (2H, dd, J=6.2, 1.6 Hz), 4.46 (2H, q, J=6.8 Hz), 1.43 (3H, t, J=7.0 Hz).

IR (CHCl$_3$) ν cm$^{-1}$: 2970, 1715, 1600, 1430, 1375, 1290, 1265, 1240, 1220.

(6) Pd(PPh$_3$)$_4$ (4.09 g, 3.54 mmol) and LiCl (22.51 g, 531 mmol) were added to 700 ml of anhydrous THF. To the mixture were added 109 (67.32 g, 177 mmol) and (n-Bu)$_3$SnH (114.3 ml, 425 mmol), and the mixture was heated to reflux at 85° C. for 2 hours. The reaction solution was concentrated under reduced pressure. To the concentrate was added methyl ether. The precipitated insoluble materials were removed by filtration and the pH of the mother liquor was adjusted to 1 by adding 1N HCl. The aqueous layer was taken and the pH was adjusted to about 9 by adding saturated NaHCO$_3$, followed by extraction with ethyl acetate. The ethyl acetate layers were combined, washed with a saturated saline solution, and dried over MgSO$_4$. MgSO$_4$ was removed by filtration and the filtrate was concentrated under reduced pressure. When the resulting residue was purified by silica gel column chromatography, 39.26 g of 110 (yield 95%) was obtained from the fraction eluted with toluene/ethyl acetate (1/1). m.p. 79–80° C.

Compound 110: NMR (CDCl$_3$) δ: 8.66 (2H, d, J=6.2 Hz), 8.12 (1H, s), 7.85 (1H, s), 7.50 (2H, dd, J=6.4, 1.8 Hz), 4.41 (2H, q, J=7.4 Hz), 1.42 (3H, t, J=7.2 Hz).

IR (CHCl$_3$) ν cm$^{-1}$: 2970, 1700, 1600, 1430, 1418, 1280, 1250, 1080.

(7) To a suspension of 110 (2.33 g, 10 mmol) in 50 ml of methanol was added 1N NaOH (20 ml, 20 mmol) at room temperature, and the mixture was stirred at 50° C. for 25 minutes. After adding 20 ml of 1N HCl under ice cooling, methanol was distilled away under reduced pressure. The precipitated solids were collected by filtration, washed in turn with isopropanol and ethyl ether, and dried to obtain 2.02 g of 111 (yield 98%). m.p. ≧300° C.

Compound 111: NMR (d$_6$-DMSO) δ: 8.61 (2H, d, J=6 Hz), 8.51 (1H, s), 8.27 (1H, s), 7.77 (2H, d, J=6 Hz).

IR (Nujol) ν cm$^{-1}$: 3336, 3080, 1699, 1611, 1296, 1211, 1065, 1026.

(8) H$_2$NCN (246 mg, 5.84 mmol) was dissolved in 15 ml of anhydrous DMF. After addition of 60% NaH (214 mg, 5.36 mmol), the mixture was stirred at room temperature for 20 minutes to prepare a solution of Na$^+$[NH—CN]$^-$/DMF. Compound 111 (1.0 g, 4.87 mmol) was added to 20 ml of anhydrous DMF, and carbonyldiimidazole (1.03 g, 5.36 mmol) was added thereto at room temperature, and the mixture was stirred for 95 minutes. To the mixture was added dropwise the previously prepared Na$^+$[NH—CN]$^-$/DMF solution under ice cooling, and the mixture was stirred for 1 hour under ice cooling. Then, 14.6 ml of hydrochloric acid was added and DMF was distilled away under reduced pressure. To the residue was added 30 ml of H$_2$O. The precipitated solids were collected by filtration, washed in turn with isopropanol and ethyl ether, and dried to obtain 921% of a white powder 112 (yield 82 mg). m.p. 249–251° C.

Compound 112: NMR (d$_6$-DMSO) δ: 8.82 (2H, d, J=6.0 Hz), 8.63 (1H, s), 8.28 (2H, d, J=6.0 Hz), 8.21 (1H, s).

IR (KBr) ν cm$^{-1}$: 3044, 2152, 1638, 1594, 1539, 1436, 1332, 1241, 1210, 816.

Preparation 27

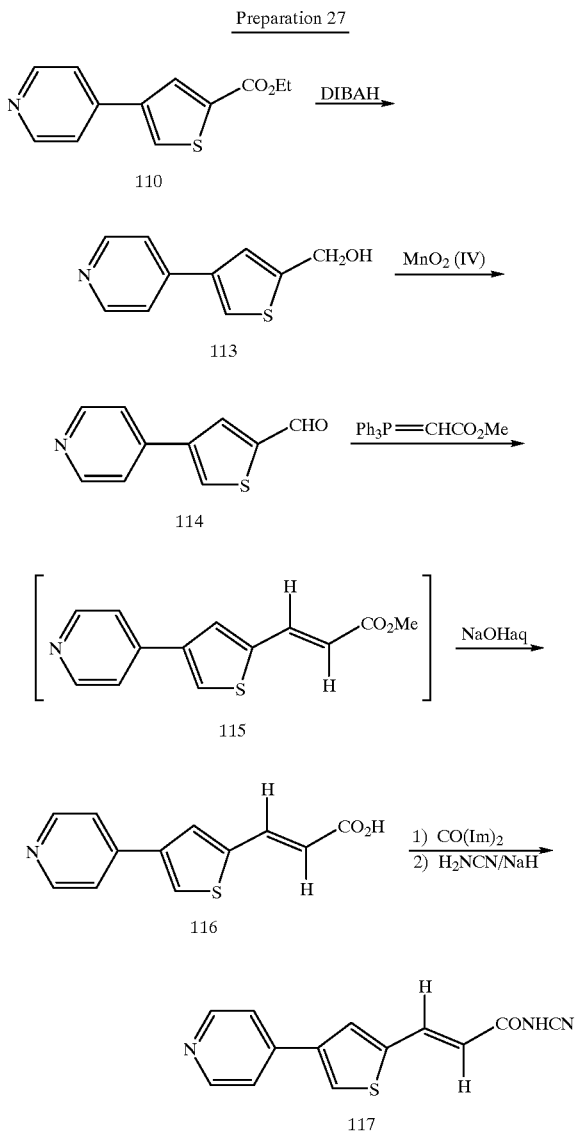

(1) Compound 110 (19.26 g, 82.56 mmol) was added to 500 ml of anhydrous toluene and the solution was cooled to −70° C. Under $N_2$ gas flow, a solution 165.12 ml (248 mmol, 1.5 M) of DIBAH/toluene was added, and the mixture was stirred at −70° C. for 35 minutes. Under ice cooling, methanol (30.1 ml, 744 mmol) and $H_2O$ (13.4 ml, 744 moles) were added. After heating to 50° C., the insoluble materials were removed by filtration. The mother liquor was concentrated under reduced pressure to obtain 14.11 g of the desired 113 (yield 89%). m.p. 138–139° C.

Compound 113: NMR ($d_6$-DMSO) δ: 8.56 (2H, dd, J=6.2, 1.8 Hz), 8.09 (1H, d, J=1.6 Hz), 7.68 (2H, dd, J=6.2, 1.6 Hz), 7.51 (1H, s), 5.59 (1H, t, J=5.7 Hz), 4.67 (2H, d, J=6.0 Hz).

IR (Nujol) ν $cm^{-1}$: 1600, 1415, 1320, 1144, 1020, 1001, 801.

(2) To a solution of 113 (1.913 g, 10 mmol) in 250 ml of anhydrous $CH_2Cl_2$ was added $MnO_2$ (activated) (6.955 g, 80 mmol) at room temperature under $N_2$ gas flow, and the mixture was stirred for 20 hours. $MnO_2$ was removed by filtration and $CH_2Cl_2$ was distilled away under reduced pressure. The resulting residue was recrystallized from $CH_2Cl_2$/n-hexane to obtain 1.42 g of a white powder 114 (yield 75%). m.p. 95–96° C.

Compound 114: NMR ($CDCl_3$) δ: 10.00 (1H, s), 8.69 (2H, d, J=6 Hz), 8.09 (1H, s), 8.05 (1H, s), 7.49 (2H, d, J=6.3 Hz).

IR ($CHCl_3$) ν $cm^{-1}$: 2962, 2820, 1676, 1601, 1418, 1174, 820.

(3) To a solution of 114 (669 mg, 3.535 mmol) in 7 ml of anhydrous THF was added $Ph_3P$=$CHCO_2Me$ (1.30 g, 3.89 mmol) at room temperature under $N_2$ gas flow, and the mixture was heated to reflux at 77° C. for 1 hour. THF was distilled away under reduced pressure to obtain 115.

To a solution of 115 in 18 ml of methanol was added 18 ml of aqueous 1N NaOH, and the mixture was stirred at 60° C. for 1 hour. Methanol was then distilled away under reduced pressure, and the resulting aqueous layer was washed three times with 100 ml of toluene. The aqueous layer was taken and adjusted to about pH 7 by adding 118 ml of 1N HCl under ice cooling. The precipitated solids were collected by filtration, washed in turn with $H_2O$ and ethyl ether, and dried to obtain 517 mg of a white powder 116 (yield 63%). m.p. 297–300° C. (decomposition).

Compound 116: NMR ($d_6$DMSO) δ: 12.51 (1H, bs), 8.62 (2H, d, J=5 Hz), 8.37 (1H, s), 8.12 (1H, s), 7.75 (1H, d, J=15.0 Hz), 7.73 (2H, d, J=6 Hz), 6.31 (1H, d, J=15.8 Hz).

IR (Nujol) ν $cm^{-1}$: 3060, 1698, 1631, 1610, 1316, 1187.

(4) To a solution of $NH_2CN$ (182 mg, 4.32 mmol) in 5 ml of anhydrous DMF was added 60% NaH (156 mg, 3.89 mmol) under ice cooling under nitrogen gas flow, and the mixture was stirred at room temperature for 1 hour to prepare a solution of $Na^+$[NH—CN]$^-$/DMF. Compound 116 (500 mg, 2.16 mmol) was suspended in 15 ml of anhydrous DMF, and carbonyldiimidazole (456 mg, 2.81 mmol) was added thereto at room temperature under $N_2$ gas flow, and the mixture was stirred for 2 hours under ice-cooling. To the suspension was added dropwise the previously prepared $Na^+$[NH—CN]$^-$/DMF solution under ice cooling, and the mixture was stirred at room temperature for 70 minutes. The pH was adjusted to about 7 by adding 1N hydrochloric acid under ice cooling, and DMF was distilled away under reduced pressure. To the resulting residue was added 100 ml of ice-cold water. The precipitated white solids were collected by filtration, washed in turn with $H_2O$, isopropanol and ethyl ether, and dried to obtain 471 mg of a white powder 117 (yield 86%). m.p. 248–250° C.

Compound 117: NMR ($d_6$-DMSO) δ: 8.66 (2H, d, J=6.75 Hz), 8.43 (1H, s), 8.15 (1H, s), 7.87 (2H, d, J=15.3 Hz), 7.78 (2H, d, J=6.0 Hz), 6.39 (1H, d, J=15.6 Hz).

IR (Nujol) ν $cm^{-1}$: 2154, 1612, 1503, 1326, 1183, 959, 820.

Example 1

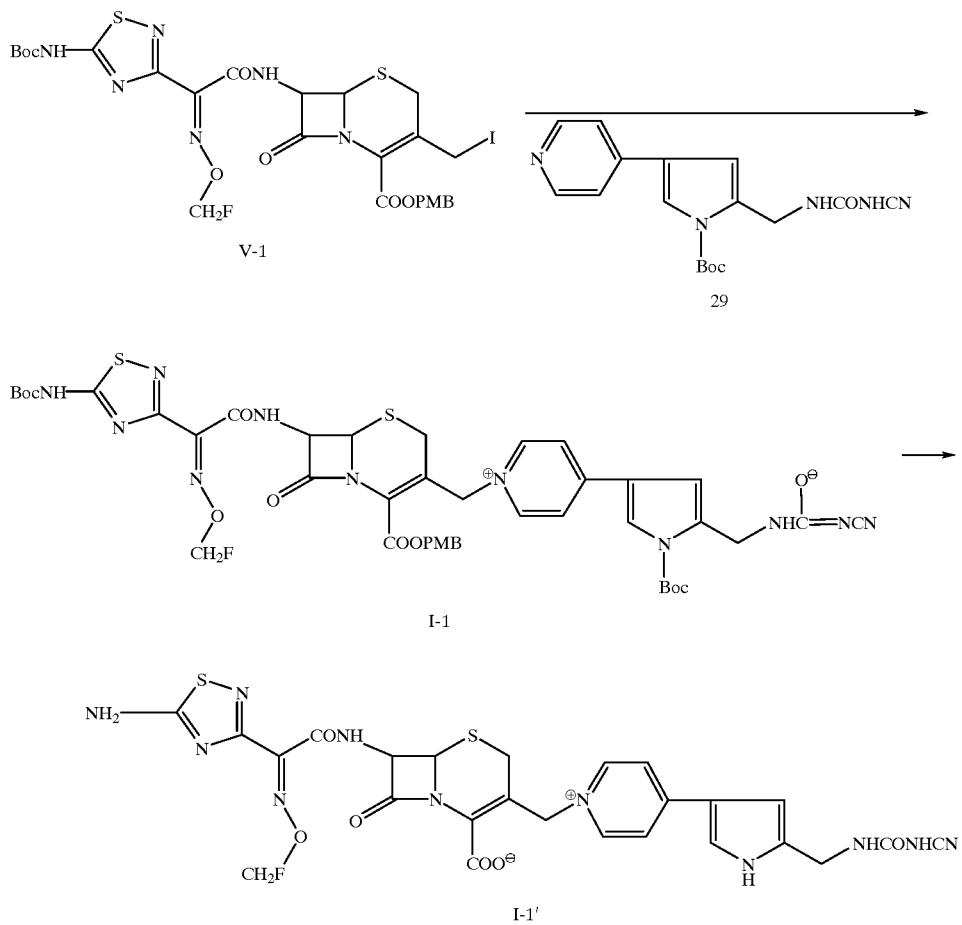

(1) To a solution of 29 (1.37 g, 4 mmol) in DMSO (15 ml) was added a solution of V-1 (3.66 g, 4.8 mmol) in acetonitrile (15 ml), and the mixture was stirred at room temperature for 2 hours. After further adding V-1 (0.92 g, 1.2 mmol), the mixture was stirred for additional 2 hours. The reaction solution was poured into a mixed solution of ethyl ether-water. The insoluble materials were collected by filtration, washed with water, and ethyl ether, and dried to obtain 6.03 g of I-1 (yield quantitative).

Compound I-1: NMR (CDCl$_3$—CD$_3$OD) δ: 1.56 (9H, s), 1.67 (9H, s), 3.81 (3H, s), 4.59 (2H, bs), 5.1~5.6 (5H, m), 5.77 (2H, d, J=55 Hz), 5.98 (1H, d, J=5 Hz), 6.77 (1H, bs), 6.91 (2H, d, J=8 Hz), 7.33 (2H, d, J=8 Hz), 8.03 (2H, d, J=6 Hz), 8.87 (2H, d, J=6 Hz).

(2) Compound I-1 (6.03 g, 5.5 mmol) was dissolved in 40 ml of dichloromethane and the solution was cooled to −30° C. After addition of a solution of aluminum chloride (6.6 g, 49 mmol) in anisole (30 ml), the mixture was stirred at the same temperature for 40 minutes. The reaction solution was poured into a mixed solution of diluted hydrochloric acid-ethanol (1:1). The aqueous solution was washed with ethyl ether and the organic solvent in the aqueous layer was distilled away under reduced pressure. The residue was then subjected to column chromatography and eluted with an aqueous solution of 5% acetonitrile-0.05N sodium hydrogencarbonate. The eluent was concentrated under reduced pressure and neutralized with diluted hydrochloric acid. The insoluble materials were collected by filtration and dried to obtain 0.46 g of I-1' (yield 12.8%).

Compound I-1': NMR (d$_6$-DMSO+D$_2$O) δ: 2.97, 3.54 (2H, ABq, J=21.0 Hz), 4.13, 4.40 (2H, ABq, J=16.5 Hz), 4.67, 5.22 (2H, ABq, J=15.0 Hz), 5.10 (1H, d, J=5 Hz), 5.70 (2H, d, J=56 Hz), 5.74 (1H, d, J=5 Hz), 6.61 (1H, s), 7.74 (2H, d, J=7 Hz), 7.79 (1H, s), 8.67 (2H, d, J=7 Hz).

IR (KBr) ν cm$^{-1}$: 2252, 2151, 1773, 1671, 1636.

The intermediate I-1 is also obtainable as a salt wherein a pyridinium cation is neutralized with an organic anion such as I$^-$, depending on the conditions of isolation and purification. In such a case, it can also be converted into the compound I-1' by subjecting to the deprotection reaction in the same manner.

Example 2

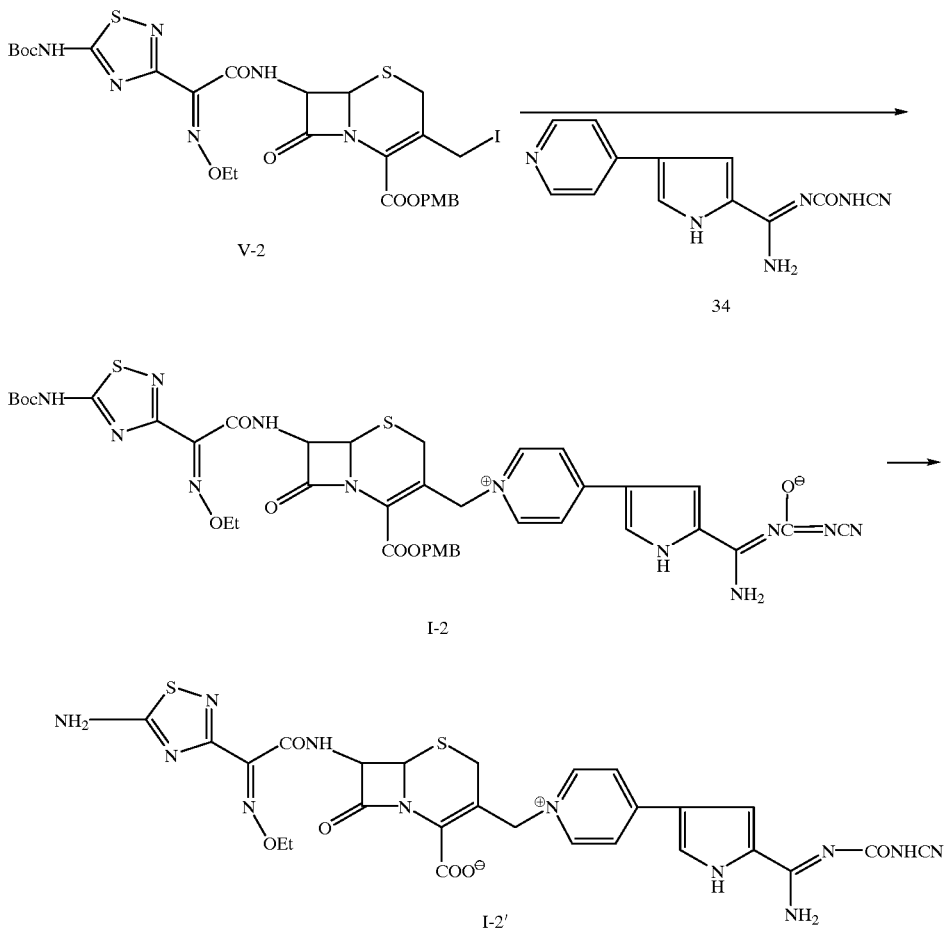

(1) Compound V-2 (0.91 g, 1.2 mmol) and 34 (254 mg, 1 mmol) were dissolved in DMSO (5 ml), and the mixture was stirred at room temperature for 2 hours. The reaction solution was poured into ethyl ether to precipitate the insoluble matter. The ether layer was removed by decantation and the insoluble materials were washed again with water, and ether, and dried to obtain 0.91 g of I-2 (yield 89.8%).

Compound I-2: NMR ($d_6$-DMSO) δ: 1.24 (3H, t, J=7 Hz), 1.51 (9H, s), 3.55, 3.70 (2H, ABq, J=10 Hz), 3.71 (3H, s), 4.17 (2H, q, J=7 Hz), 5.18~5.31 (3H, m), 5.44 (2H, bs), 5.97 (1H, d, J=5 Hz), 6.91 (2H, d, J=8 Hz), 7.36 (2H, d, J=8 Hz), 8.06 (1H, s), 8.15 (2H, d, J=6 Hz), 8.40 (1H, s), 8.76 (2H, d, J=6 Hz).

(2) To a solution of I-2 (0.91 g, 0.90 mmol) in a mixed solution of dichloromethane (10 ml)-nitromethane (6 ml) was added a solution of aluminum chloride (0.72 g, 5.4 mmol) in anisole (6 ml) at −20° C., and the mixture was stirred at the same temperature for 1 hour. The reaction solution was poured into a mixed solution of diluted hydrochloric acid-ethanol and washed with ethyl ether. After distilling away under reduced pressure an organic solvent from the aqueous layer, the aqueous solution was subjected to column chromatography, and eluted with an aqueous solution of 12% acetonitrile-0.05N sodium hydrogencarbonate. The eluent was concentrated under reduced pressure and neutralized with diluted hydrochloric acid to obtain 223 mg of I-2' (yield 38.7%).

Compound I-2': NMR ($d_6$-DMSO-$D_2O$) δ: 1.21 (3H, t, J=7 Hz), 3.17, 3.57 (2H, ABq, J=18.0 Hz), 5.08, 5.52 (2H, ABq, J=18.0 Hz), 5.10 (1H, d, J=5 Hz), 5.74 (1H, d, J=5 Hz), 8.17 (1H, s), 8.21 (2H, d, J=7 Hz), 8.36 (1H, s), 9.13 (2H, d, J=7 Hz).

IR (KBr) ν $cm^{-1}$: 2177, 1772, 1636.

Example 3

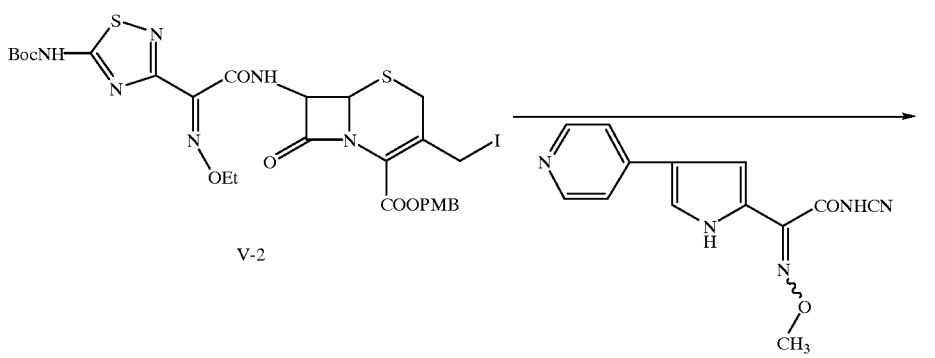

V-2

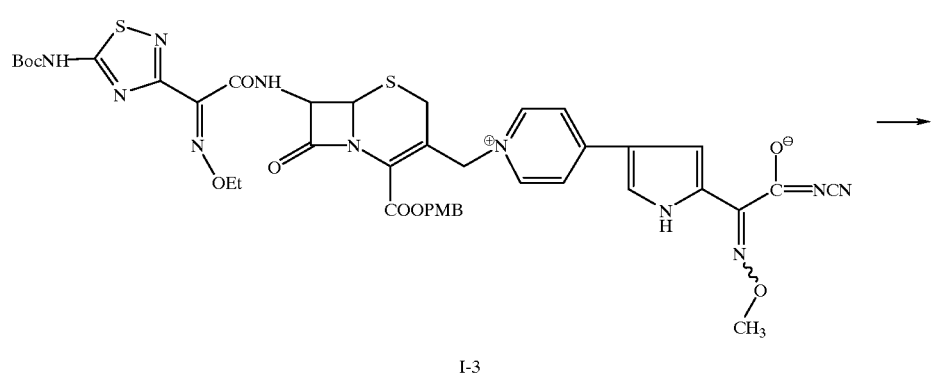

I-3

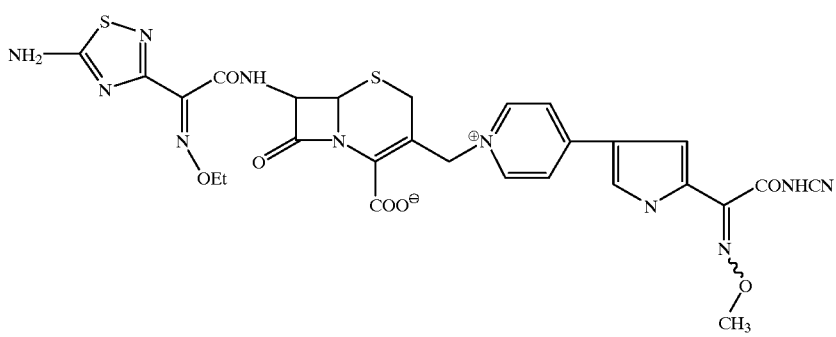

I-3'

(1) The reaction was carried out using V-2 (910 mg, 1.2 moles) and 44 (240 mg, 0.9 mmol) as starting materials in a manner similar to that described in Example 1 to obtain 0.79 of I-3 (yield 85.4%).

(2) Compound I-3 (783 mg, 0.76 mmol) was reacted with $AlCl_3$ in $CH_2Cl_2$—$CH_3NO_2$ to obtain 30 mg of I-3' (yield 5.8%).

Compound I-3': NMR ($d_6$-DMSO) δ: 1.21 (3H, t, J=7 Hz), 3.37, 3.52 (2H, ABq, J=18.0 Hz), 3.82 (3H, s), 4.14 (2H, q, J=7 Hz), 5.19 (1H, d, J=5 Hz), 5.17, 5.38 (2H, ABq, J=15.0 Hz), 5.88 (1H, dd, J=5 Hz, 8 Hz), 6.92 (1H, s), 8.05 (1H, s), 8.15 (2H, bs), 8.28 (2H, d, J=7 Hz), 8.73 (2H, d, J=7 Hz), 9.60 (2H, d, J=8 Hz), 12.12 (1H, bs).

IR (KBr) ν $cm^{-1}$: 2257, 2164, 1780, 1671, 1636.

Example 4

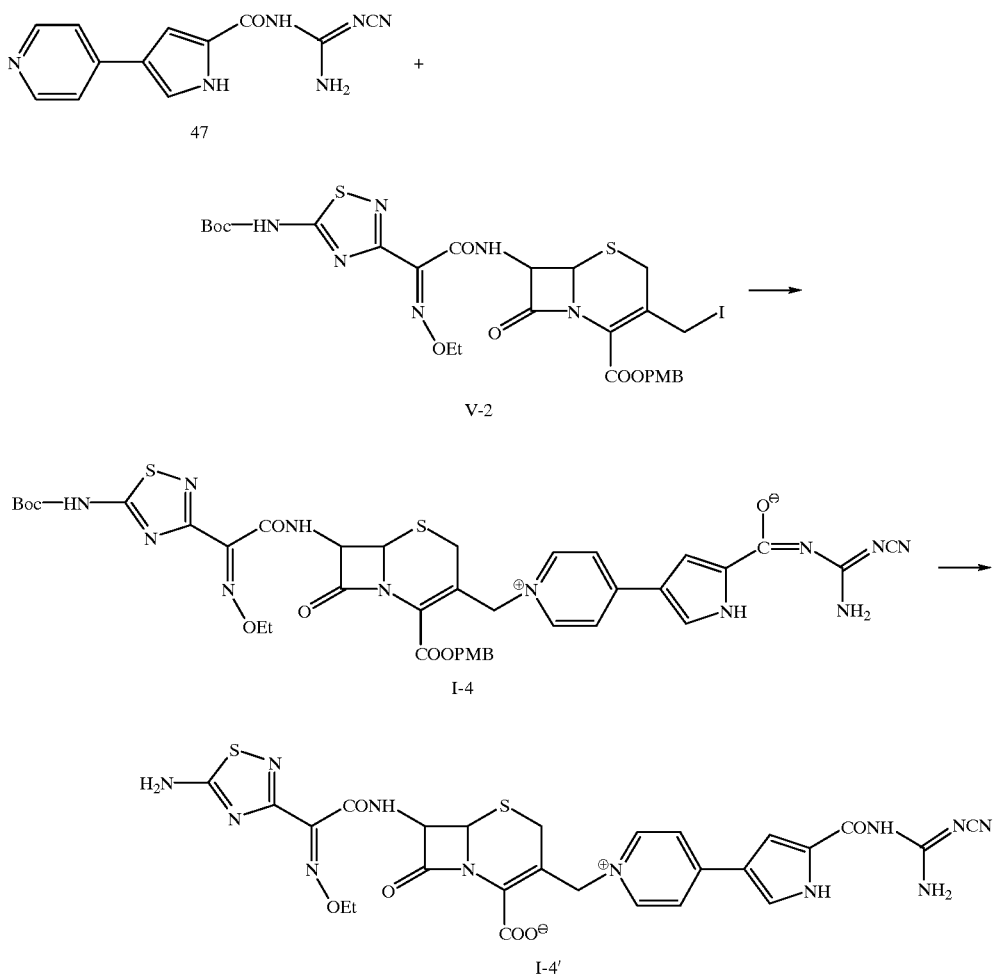

(1) To a solution of 47 (203 mg, 0.8 mmol) in DMSO (10 ml) was added V-2 (789 mg, 1.03 mmol), and the mixture was stirred for 45 minutes. The resulting solution was added dropwise to ethyl ether (500 ml) with stirring and the mother liquor was decanted to obtain an oily insoluble matter. The insoluble materials were washed with $H_2O$, collected by filtration, dissolved in a mixed solution of $CHCl_3$ and acetonitrile, and dried over $MgSO_4$ to obtain 830 mg of I-4.

Compound I-4: NMR ($d_6$-DMSO) δ: 1.24 (3H, t, J=7.0 Hz), 1.51 (9H, s), 3.53 (2H, bs), 3.73 (3H, s), 4.21 (2H, q, J=7.0 Hz), 5.22 (2H, bs), 5.22 (1H, d, J=5.2 Hz), 5.43 (2H, bs), 6.00 (1H, dd, J=5.2, 8.6 Hz), 6.93 (2H, d, J=8.6 Hz), 7.37 (2H, d, J=8.6 Hz), 8.08 (1H, bs), 8.15 (2H, d, J=6.6 Hz), 8.33 (1H, bs), 8.77 (2H, d, J=6.6 Hz), 9.04 (1H, bs), 9.69 (1H, d, J=8.6 Hz), 11.18 (1H, bs), 12.61 (1H, bs), 12.96 (1H, bs).

IR (KBr) ν $cm^{-1}$: 2182, 1784, 1713, 1679, 1634.

(2) To a solution of I-4 (820 mg, 0.81 mmol) in 30 ml of $CH_2Cl_2$ and 30 ml of $CH_3NO_2$ was added anisole (1.06 ml, 9.75 ml). To the solution was added 7.29 ml of a solution of $AlCl_3$ in $CH_3NO_2$ (1M) at −20° C., and the mixture was stirred at the same temperature for 30 minutes. The reaction solution was poured into a mixture of $H_2O$ (100 ml), ethanol (100 ml) and sodium tartrate (3.4 g, 14.8 mmol) previously stirred under ice cooling. The resulting suspension was washed with ethyl ether. The aqueous layer was concentrated under reduced pressure and subjected to column chromatography (40% acetonitrile/$H_2O$). The eluent was concentrated under reduced pressure. The precipitated insoluble materials were filtered to obtain 111 mg of I-4' (yield 21%).

Compound I-4': NMR ($d_6$-DMSO(+$D_2O$)) δ: 1.20 (3H, t, J=7.0 Hz), 3.09, 3.52 (2H, ABq, J=19.0 Hz), 4.12 (2H, q, J=7.0 Hz), 4.96, 5.54 (2H, ABq, J=13.8 Hz), 5.06 (1H, d, J=5.0 Hz), 5.70 (1H, d, J=5.0 Hz), 8.10 (1H, bs), 7.20 (2H, d, J=7.0 Hz), 8.26 (1H, bs), 9.20 (2H, d, J=7.0 Hz).

IR (KBr) ν $cm^{-1}$: 2182, 1768, 1635.

Example 5

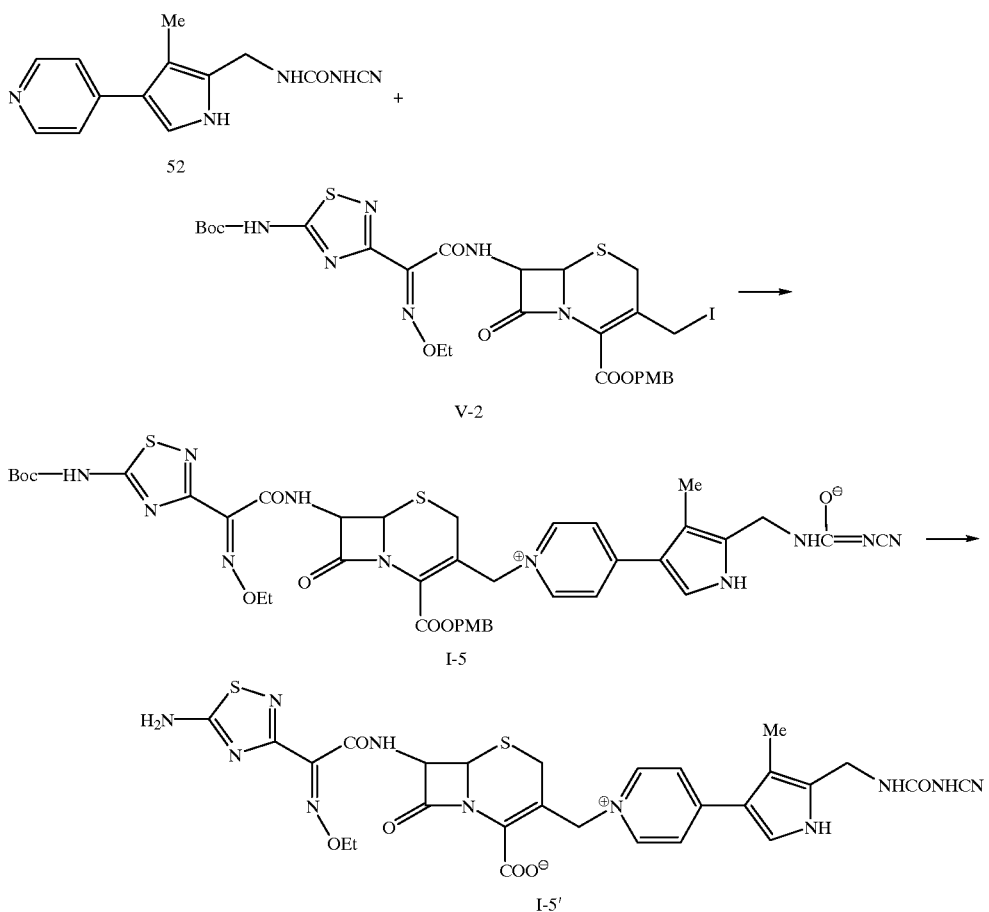

(1) To a solution of 52 (951 mg, 3.73 mmol) in 40 ml of DMSO was added V-2 (4.24 g, 5.59 mmol), and the mixture was stirred for 30 minutes at room temperature. The resulting reaction solution was added dropwise to 200 ml of ethyl ether with stirring. The mother liquor was decanted to obtain an oily insoluble material, which was then washed with 400 ml of $H_2O$. The precipitated insoluble materials were collected by filtration, and dissolved in a mixed solution of a small amount of $CHCl_3$ and acetonitrile. To the solution were added 100 ml of ethyl acetate and 400 ml of ethyl ether, and the precipitated insoluble materials were filtered to obtain 3.14 g of I-5 (yield 83%).

Compound I-5: NMR ($d_6$-DMSO) δ: 1.23 (3H, t, J=7.0 Hz), 1.50 (9H, s), 2.26 (3H, s), 3.44~3.64 (2H, m), 3.72 (3H, s), 4.20 (2H, q, J=7.0 Hz), 4.20 (2H, bs), 5.22 (2H, bs), 5.23 (1H, d, J=5.4 Hz), 5.25~5.43 (2H, m), 5.99 (1H, dd, J=5.4, 8.2 Hz), 6.92 (2H, d, J=8.6 Hz), 7.21 (1H, bs), 7.36 (2H, d, J=8.6 Hz), 7.78 (1H, bs), 8.05 (2H, d, J=7.2 Hz), 8.58 (2H, d, J=7.2 Hz), 9.69 (1H, d, J=8.2 Hz), 11.56 (1H, s), 12.60 (1H, bs).

IR (KBr) ν $cm^{-1}$: 2244, 2146, 1786, 1714, 1634.

(2) To a solution of I-5 (3.13 g, 3.09 mmol) in 30 ml of $CH_2Cl_2$ and 20 ml of $CH_3NO_2$ was added anisole (4.03 ml, 37.08 mmol). After cooling to −20° C., 4.03 ml of a solution of $AlCl_3$ in $CH_3NO_2$ (1M) was added, and the mixture was stirred at the same temperature for 40 minutes. The reaction solution was poured into a mixture of ethanol (100 ml) and 100 ml of 0.1N HCl previously stirred under ice cooling. The resulting suspension was washed with ethyl ether. The aqueous layer was concentrated under reduced pressure and subjected to column chromatography (acetonitrile/0.05N $NaHCO_3$ 10%). The eluent was adjusted to about pH 7 with 1N HCl, and concentrated under reduced pressure. To the concentrate was added 1N HCl and the precipitated insoluble materials were filtered to obtain 515 mg of I-5' (yield 27%).

Compound I-5': NMR ($d_6$-DMSO) δ: 1.16 (3H, t, J=7.2 Hz), 2.21 (3H, s), 3.00, 3.56 (2H, ABq, J=18.6 Hz), 3.09 (2H, q, J=7.2 Hz), 4.09~4.33 (2H, m), 4.70, 5.24 (2H, ABq, J=13.8 Hz), 5.08 (1H, d, J=4.6 Hz), 5.75 (1H, dd, J=4.6, 7.8 Hz), 7.74 (2H, d, J=7.0), 7.75 (1H, bs), 7.66 (2H, d, J=7.0 ), 7.46 (1H, d, J=7.8 Hz), 11.80 (1H, bs).

IR (KBr) ν $cm^{-1}$: 2244, 2160, 1769, 1676, 1633.

Example 6

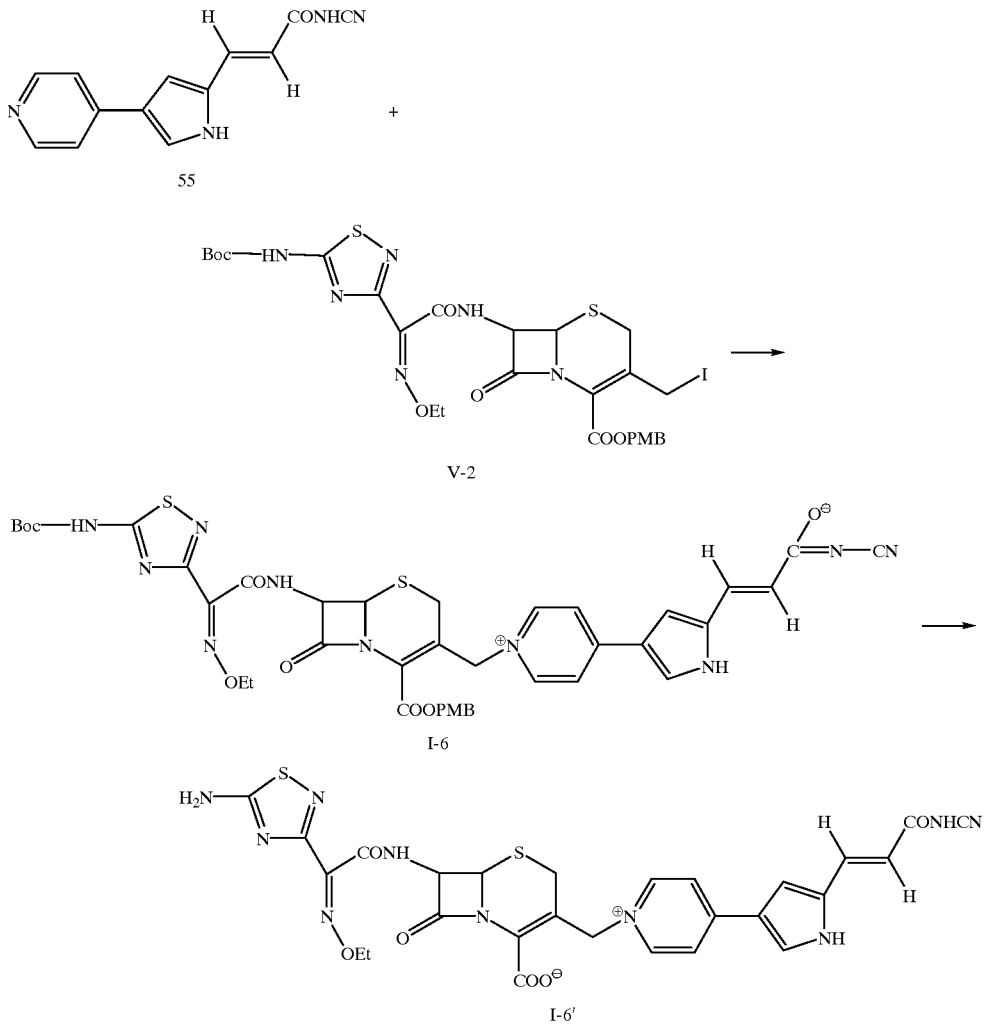

(1) To a suspension of 55 (477 mg, 2 mmol) in 25 ml of DMSO was added V-2 (2.73 g, 3.60 mmol), and the mixture was stirred for 7 hours at room temperature. The resulting reaction solution was added dropwise to 500 ml of ethyl ether with stirring and the mother liquor was decanted to obtain an oily insoluble material, which was then washed with $H_2O$. The precipitated insoluble materials were collected by filtration, and dissolved in a mixed solution of $CHCl_3$ and acetonitrile. The solution was dried over $MgSO_4$, and added dropwise to 100 ml of ethyl acetate with stirring. When 500 ml of ethyl acetate was added, insoluble materials were precipitated, which were filtered off to obtain 1.31 g of I-6 (yield 66%).

Compound I-6: NMR ($d_6$-DMSO) δ: 1.23 (3H, t, J=7.0 Hz), 1.50 (9H, s), 3.52 (2H, bs), 3.73 (3H, s), 4.20 (2H, q, J=7.0 Hz), 5.23 (1H, d, J=5.0 Hz), 5.24 (2H, bs), 5.39 (2H, bs), 5.99 (1H, q, J=5.0, 8.2 Hz), 6.38 (1H, d, J=15.2 Hz), 6.93 (2H, d, J=8.2 Hz), 7.35 (2H, d, J=8.2 Hz), 7.36 (1H, bs), 7.47 (1H, d, J=15.2 Hz), 8.21 (2H, d, J=7.0 Hz), 8.25 (1H, bs), 8.68 (2H, d, J=7.0 Hz), 9.69 (1H, d, J=8.2 Hz), 12.61 (1H, s).

IR (KBr) ν $cm^{-1}$: 2230, 2150, 1785, 1712, 1690, 1616.

(2) To a solution of I-6 (1.30 g, 1.30 mmol) in 20 ml of $CH_2Cl_2$ and 20 ml of $CH_3NO_2$ was added anisole (1.70 ml, 14.9 mmol). After cooling to −20° C., 11.7 ml of a solution of $AlCl_3$ in $CH_3NO_2$ (1M) was added, and the mixture was stirred at the same temperature for 30 minutes. The reaction solution was poured into a mixture of 100 ml of ethanol and 100 ml of 0.1N HCl previously stirred under ice cooling. The resulting suspension was washed with ethyl ether. The aqueous layer was concentrated under reduced pressure and subjected to column chromatography (10% acetonitrile/ 0.05N $NaHCO_3$). The eluent was concentrated under reduced pressure and adjusted to about pH 2 with 1N HCl. The precipitated insoluble materials were filtered, and washed with isopropanol and ethyl ether to obtain 131 mg of I-6' (yield 16%).

Compound I-6': NMR ($d_6$-DMSO) δ: 1.21 (3H, t, J=7.0 Hz), 3.33, 3.54 (2H, ABq, J=18.4 Hz), 4.14 (2H, q, J=7.0 Hz), 5.17 (1H, d, J=5.0 Hz), 5.21, 5.41 (2H, ABq, J=14.6 Hz), 5.86 (1H, dd, J=5.0, 8.2 Hz), 6.33 (1H, d, J=16.0 Hz), 7.18 (1H, bs), 7.24 (1H, d, J=16.0 Hz), 8.14 (2H, bs), 8.16 (1H, bs), 8.19 (2H, d, J=6.2 Hz), 8.81 (2H, d, J=6.2 Hz), 9.57 (1H, d, J=8.2 Hz), 12.33 (1H, bs).

IR (KBr) ν $cm^{-1}$: 2232, 2148, 1772, 1673, 1619.

Example 7

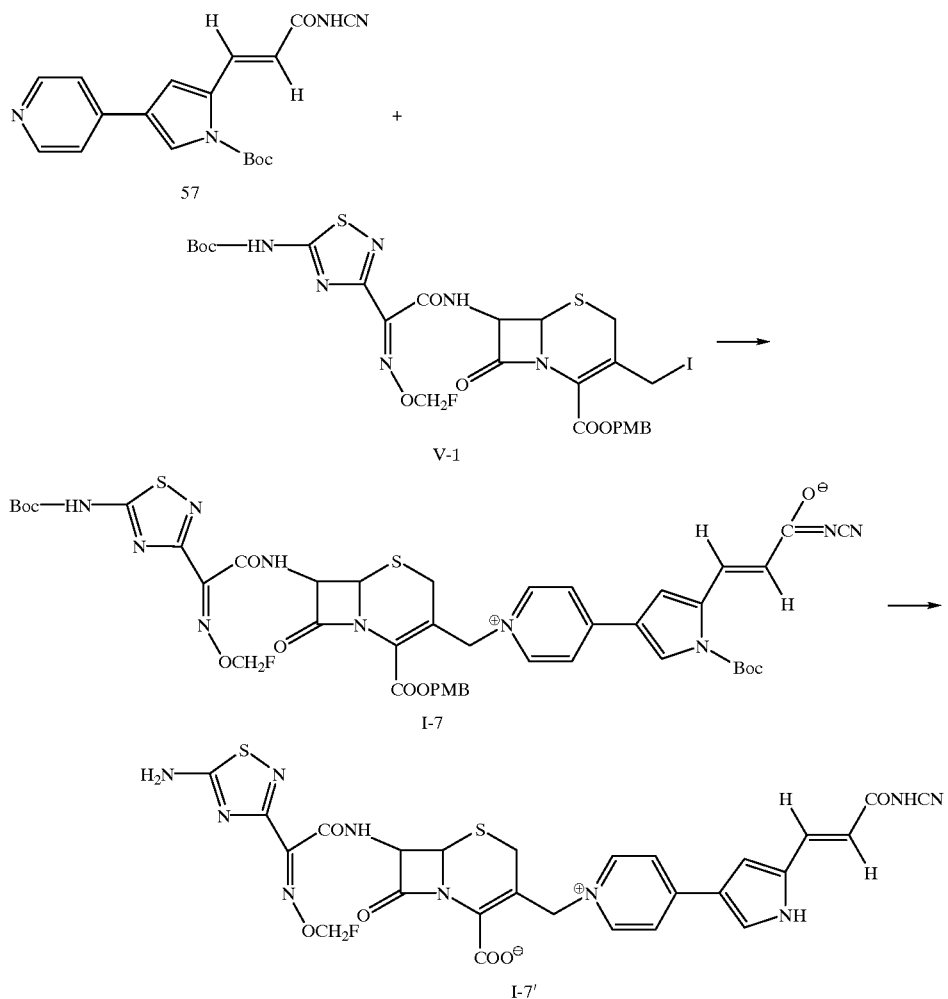

(1) To a suspension of 57 (508 mg, 150 mmol) in 10 ml of DMSO was added N,O-bis(trimethylsilyl)acetamide (403 μl, 1.63 mmol), and the mixture was stirred. After adding V-1 (1.24 g, 1.63 mmol), the mixture was stirred at room temperature for 95 minutes. The resulting reaction solution was added dropwise to an aqueous 5% NaCl solution. The precipitated insoluble materials were collected by filtration, and dissolved in 50 ml of acetonitrile. After adding 100 ml of ethyl acetate, the solution was concentrated under reduced pressure. To the concentrate was added 100 ml of ethyl acetate, and the precipitated insoluble materials were filtered off to obtain 1.45 g of I-7 (yield 98%).

Compound I-7: NMR ($d_6$-DMSO) δ: 1.51 (9H, s), 1.64 (9H, s), 3.54 (2H, bs), 3.73 (3H, s), 5.17~5.31 (2H, m), 5.25 (1H, d, J=4.6 Hz), 5.47 (2H, bs), 5.81 (2H, d, J=55.4 Hz), 6.00 (1H, dd, J=4.6 Hz, 8.2 Hz), 6.45 (1H, d, J=15.4 Hz), 6.91 (2H, d, J=8.4 Hz), 7.35 (2H, d, J=8.4 Hz), 7.65 (1H, bs), 8.01 (1H, d, J=15.4 Hz), 8.44 (2H, d, J=6.4 Hz), 8.56 (1H, bs), 8.82 (2H, d, J=6.4 Hz), 9.89 (1H, d), 12.67 (1H, bs).

IR (KBr) ν $cm^{-1}$: 2234, 2150, 1770, 1715, 1615.

(2) To a solution of I-7 (473 mg, 0.49 mmol) in 8 ml of $CH_2Cl_2$ and 3 ml of $CH_3NO_2$ was added anisole (640 μl, 5.89 mmol). After cooling to −4° C., 4.41 ml of a solution of $TiCl_4$ in $CH_2Cl_2$ (1M) was added, and the mixture was stirred under ice cooling for 30 minutes. The reaction solution was poured into a mixture of 50 ml of 1N NCl and ethanol (50 ml) previously stirred under ice cooling. The insoluble materials were filtered off from the resulting suspension, and dissolved in an aqueous $NaHCO_3$ solution. A small amount of the insoluble materials were filtered, and the solution was separated and purified by HP-20SS column chromatography (2–4% acetonitrile/$H_2O$). The eluent was adjusted to about pH 3.05 with 1N HCl, and concentrated under reduced pressure. The precipitated insoluble materials were filtered off to obtain 137 mg of I-7' (yield 36%).

Compound I-7': NMR ($d_6$-DMSO) δ: 3.29, 3.56 (2H, ABq, J=18.0 Hz), 5.18, 5.43 (2H, ABq, J=14.6 Hz), 5.19 (1H, d, J=5.0 Hz), 5.75 (2H, d, J=54.0 Hz), 5.85 (1H, dd, J=5.0, 8.2 Hz), 6.34 (1H, d, J=15.6 Hz), 7.20 (1H, bs), 7.28 (1H, d, J=15.6 Hz), 8.12 (1H, bs), 8.19 (2H, d, J=6.6 Hz), 8.81 (2H, d, J=6.6 Hz), 8.81 (1H, d, J=8.2 Hz).

IR (KBr) ν $cm^{-1}$: 2228, 2146, 1772, 1680, 1620.

Example 8

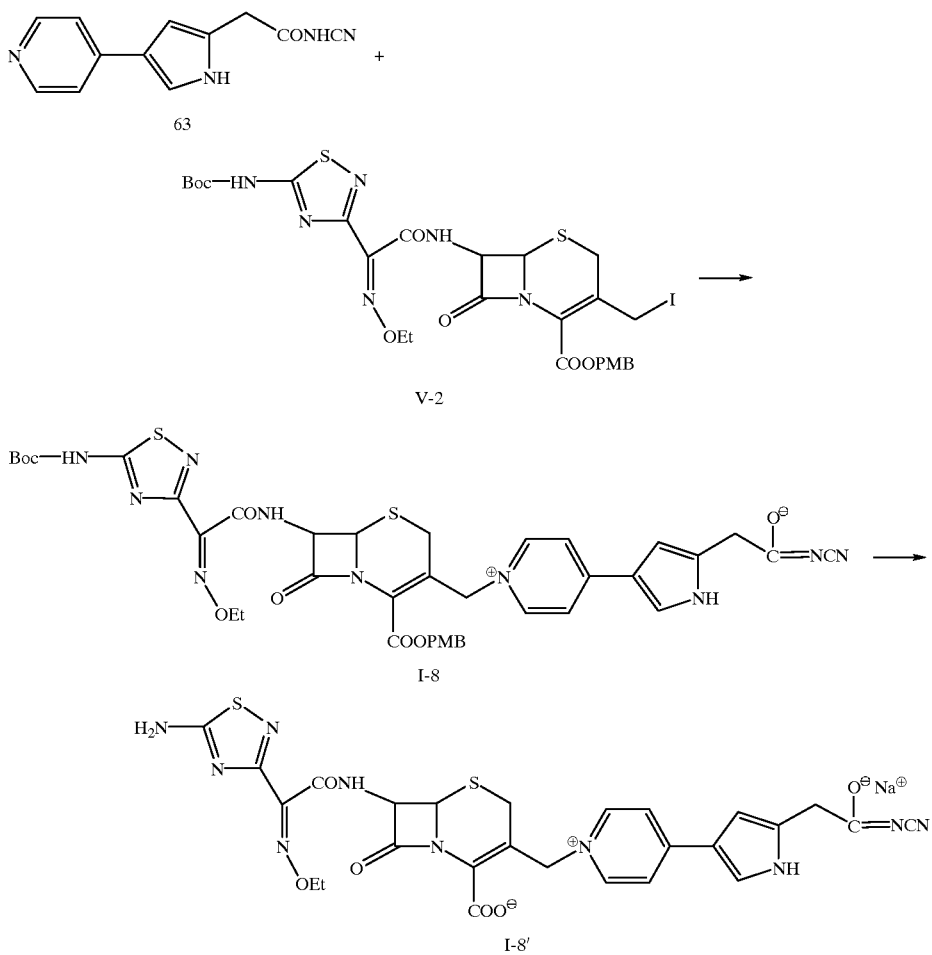

(1) To a solution of 63 (100 mg, 0.44 mmol) in 10 ml of DMSO was added V-2 (402 mg, 0.53 mmol), and the mixture was stirred at room temperature for 30 minutes. The reaction solution was added dropwise to 200 ml of ethyl ether with stirring, and the mother liquor was decanted to obtain an oily insoluble material, which was dissolved in 10 ml of $CH_2Cl_2$. The solution was again added dropwise to 200 ml of ethyl ether with stirring. The precipitated insoluble materials were filtered off to obtain 37.4 mg of I-8 (yield 86%).

Compound I-8: NMR ($d_6$-DMSO) δ: 1.24 (3H, t, J=7.0 Hz), 1.51 (9H, s), 3.44–3.62 (2H, m), 3.70 (2H, s), 3.74 (3H, s), 4.20 (2H, q, J=7.0 Hz), 5.24 (1H, d, J=5.2 Hz), 5.25 (2H, bs), 5.36 (2H, bs), 5.99 (1H, dd, J=5.2, 8.8 Hz), 6.68 (1H, bs), 6.93 (2H, d, J=8.6 Hz), 7.37 (2H, d, J=8.6 Hz), 7.97 (1H, bs), 8.10 (2H, d, J=7.0 Hz), 8.58 (2H, d, J=7.0 Hz), 9.71 (1H, d, J=8.8 Hz), 11.62 (1H, bs), 11.78 (1H, bs), 12.61 (1H, bs).

IR (KBr) ν $cm^{-1}$: 2250, 2156, 1784, 1715.

(2) To a solution of I-8 (370 mg, 0.38 mmol) in 6 ml of $CH_2Cl_2$ and 6 ml of $CH_3NO_2$ was added anisole (490 ml, 4.51 mmol). After adding 3.38 ml of a solution of $AlCl_3$ in $CH_3NO_2$ (1M) at −20° C., the mixture was stirred at the same temperature for 30 minutes. The reaction solution was poured into a mixture of a solution of $CH_3COONa$ (863 mg, 10.5 mmol) in $H_2O$ (100 ml), ethanol (100 ml) and ethyl ether (200 ml) previously stirred under ice cooling. The insoluble materials were filtered from the aqueous layer, and dissolved in $NaHCO_3$ solution. A small amount of the insoluble materials were filtered. The mother liquor was separated and purified by column chromatography (10% methanol/0.05N $NaHCO_3$). The solution was concentrated under reduced pressure, adjusted to about pH 6.0 with 1N HCl, and desalted to obtain 70 mg of I-8' (yield 28%).

Compound I-8': NMR ($d_6$-DMSO) δ: 1.20 (3H, t, J=7.2 Hz), 3.05, 3.49 (2H, ABq, J=18.3 Hz), 4.11 (2H, q, J=7.2 Hz), 4.84, 5.43 (2H, ABq, J=14.0 Hz), 5.06 (1H, d, J=5.0 Hz), 5.67 (1H, dd, J=5.0, 8.4 Hz), 6.50 (1H, bs), 7.78 (1H, bs), 8.05 (2H, d, J=7.0 Hz), 9.01 (2H, d, J=7.0 Hz), 9.47 (1H, d, J=8.4 Hz), 9.87 (1H, s), 11.54 (1H, bs).

IR (KBr) ν $cm^{-1}$: 2156, 1764, 1681, 1634.

In the following Examples,

represents

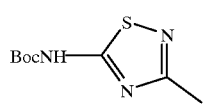

Example 9

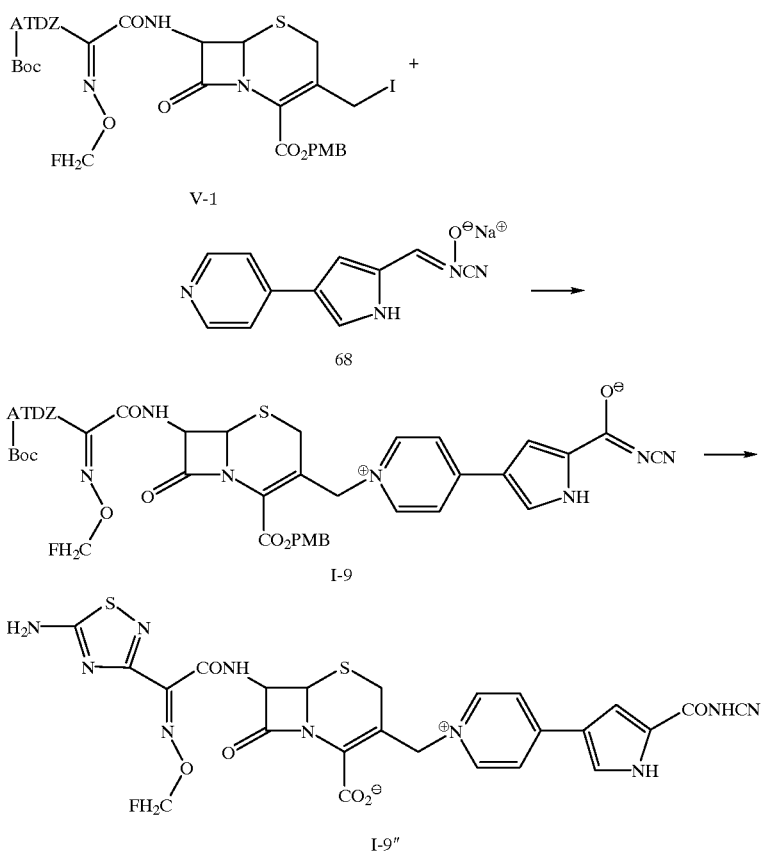

(1) To a solution of 68 (234 mg, 1 mmol) in anhydrous DMSO (7 ml) was added V-1 (830 mg, 1.09 mmol) at room temperature under $N_2$ gas flow, and the mixture was stirred for 1 hour. The reaction solution was poured into 70 ml of a 5% saline solution. The precipitated solids were collected by filtration, and dissolved in a mixed solution of acetonitrile (40 ml)/CHCl$_3$ (20 ml). The solution was dried over MgSO$_4$ and concentrated under reduced pressure. The resulting residue was added to ethyl acetate (50 ml). The resultant precipitates were collected by filtration and dried to obtain 739 mg of a yellow powder I-9 (yield 87%).

Compound I-9: NMR (d$_6$-DMSO) δ: 12.67 (1H, bs), 12.12 (1H, bs), 9.90 (1H, d, J=8.7 Hz), 8.58 (2H, d, J=7.2 Hz), 8.19 (2H, d, 6.9 Hz), 7.92 (1H, bs), 7.35 (2H, d, J=8.4 Hz), 7.22 (1H, s), 6.92 (2H, d, J=8.4 Hz), 5.99 (1H, dd, J=11.5 Hz, 7.3 Hz), 5.90 (1H, s), 5.72 (1H, s), 5.21–5.34 (5H, m), 3.73 (3H, s), 3.43, 3.58 (2H, ABq, J=19 Hz), 1.51 (9H, s).

IR (KBr) ν cm$^{-1}$: 2970, 2148, 1784, 1711, 1635, 1548.

(2) A suspension of I-9 (729 mg, 0.86 mmol) in 20 ml of anhydrous CH$_2$Cl$_2$ and 50 ml of anhydrous CH$_3$NO$_2$ was cooled to −3° C. In a N$_2$ gas flow, to the suspension were added dropwise anisole (1.1 ml, 10.32 mmol), and then a solution (5.16 ml, 5.16 mmol) of TiCl$_4$ (1 mole)/CH$_2$Cl$_2$ over 10 minutes, and the mixture was stirred at 0° C. for 1 hour. The reaction solution was then added dropwise to a mixed solution of 10 ml of 1N HCl and 10 ml of a 5% saline solution under ice cooling. To the mixture was added ethyl ether (80 ml). The precipitated solids were collected by filtration, washed with 1N HCl and H$_2$O, dissolved in NaHCO$_3$, and purified by column. The portion eluted with 7% acetonitrile/0.05 N NaHCO$_3$ was adjusted to pH 2.9 and concentrated under reduced pressure. The precipitated solid was collected by filtration, washed in turn with H$_2$O, isopropanol and ethyl ether to obtain 266 mg of a pale yellow powder I-9" (yield 49.4%).

The same results were obtained by using a solution of AlCl$_3$ (1 mole)/CH$_3$NO$_2$ as Lewis acid.

Compound I-9": NMR (d$_6$-DMSO) δ: 12.11 (1H, bs), 8.67 (2H, d, J=6.9 Hz), 8.22 (2H, d, J=7.2 Hz), 8.20 (2H, s), 7.90 (1H, s), 7.21 (1H, s), 5.90 (1H, dd, J=8.4, 4.8 Hz), 5.85 (1H, s), 5.66 (1H, s), 5.38, 5.22 (2H, ABq, J=18 Hz), 5.21 (1H, d, J=5.1 Hz), 3.56, 3.36 (2H, ABq, J=18 Hz).

IR (KBr) ν cm$^{-1}$: 3412, 2256, 2156, 1777, 1677, 1636, 1569, 1219, 1149.

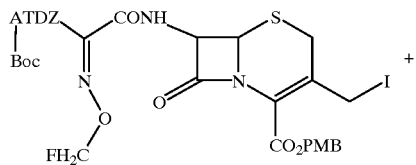
V-1
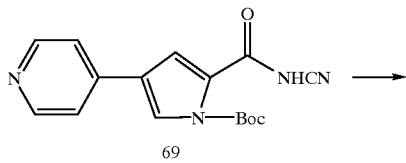
69
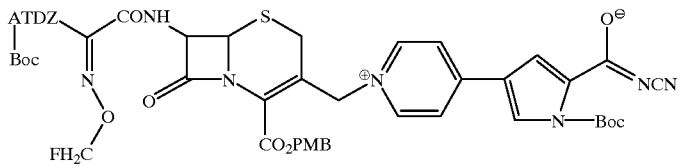
I-9'
(3) In a manner similar to that described above, 7.35 g of a yellowish brown powder I-9' (yield 76%) was obtained from V-1(4.118 g, 9.92 mmol) and 69 (2.811 g, 9 mmol).
Compound I-9' 3: NMR (d$_6$-DMSO) δ: 12.68 (1H, bs), 9.95 (1H, d, J=10.3 Hz), 8.76 (2H, d, J=7.90 Hz), 8.43 (1H, s), 8.37 (2H, d, J=7.50 Hz), 7.37 (3H, d, J=7.90 Hz), 6.91 (2H, d, J=8.69 Hz), 6.00 (1H, dd, J=8.77, 6.32 Hz), 5.90 (1H, bs), 5.71 (1H, bs), 5.15~5.50 (5H, m), 3.72 (3H, s), 3.49, 3.59 (2H, ABq, J=19.7 Hz), 1.56 (9H, s), 1.51 (9H, s).
IR (KBr) ν cm$^{-1}$: 2970, 2150, 1788, 1714, 1634, 1246, 1149.
Example 10
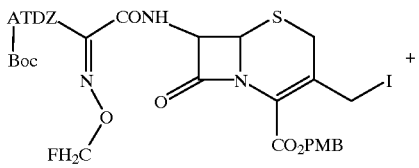
V-1
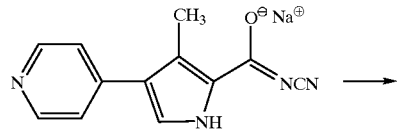
70
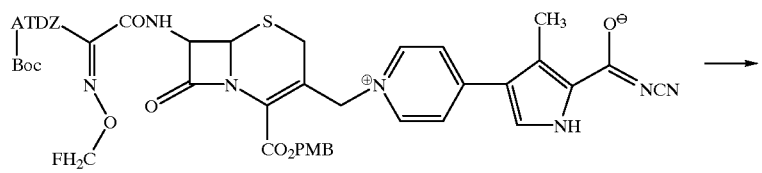
I-10

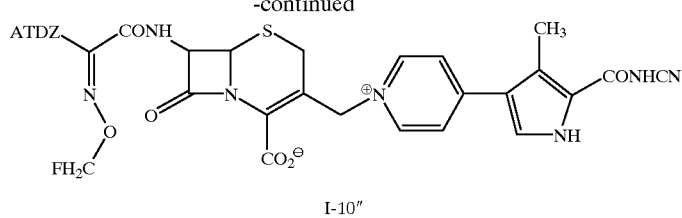

I-10''

(1) In a manner similar to that described above, 4.75 g of a yellow powder I-10 was obtained from 70 (1.24 g, 5.0 mmol) and V-1 (4.14 g, 5.0 mmol). Further, in a manner similar to that described above, 1.3 g of a pale yellow powder I-10'' (yield 41%) was obtained from 1-10 (4.75 g, 5 mmol).

Compound I-10: NMR ($d_6$-DMSO) δ: 12.67 (1H, bs), 11.84 (1H, bs), 9.90 (1H, d, J=8.1 Hz), 8.60 (2H, d, J=4.9 Hz), 8.09 (2H, d, J=6.9 Hz), 7.69 (1H, d, J=3.3 Hz), 7.36 (2H, d, J=8.4 Hz), 6.91 (2H, d, J=8.7 Hz), 6.04 (1H, dd, J=8.4, 4.8 Hz), 5.90 (1H, bs), 5.72 (1H, bs), 5.20~5.44 (5H, m), 3.72 (3H, s), 2.63 (3H, s), 1.51 (9H, s).

IR (KBr) ν $cm^{-1}$: 2970, 2150, 1784, 1711, 1633.

Compound I-10'': NMR ($d_6$-DMSO) δ: 11.83 (1H, bs), 9.80 (1H, d, J=8.2 Hz), 8.70 (2H, d, J=6.60 Hz), 8.20 (2H, s), 8.13 (2H, d, J=6.60 Hz), 7.68 (1H, d, J=3.40 Hz), 5.89 (2H, m), 5.62 (1H, s), 5.43, 5.23 (2H, ABq, J=14 Hz), 5.20 (1H, d, J=5.0 Hz), 5.59, 5.37 (2H, ABq, J=18.5 Hz), 2.64 (3H, s).

IR (Nujol) ν $cm^{-1}$: 3184, 2144, 1773, 1675, 1633, 1215.

(2) In a manner similar to that described above, 45.1 mg of a yellowish brown powder I-10' was obtained from 7 (150 mg, 0.43 mmol) protected with Boc and V-1 (328 mg, 0.43 mmol).

Compound I-10': NMR ($CDCl_3$) δ: 9.04 (1H, d, J=7.0 Hz), 8.05 (2H, d, J=6.4 Hz), 7.91 (1H, s), 7.34 (2H, d, J=10.5 Hz), 6.90 (2H, d, J=8.6 Hz), 6.0 (1H, d, J=5.0 Hz), 5.93 (1H, m), 5.64 (1H, m), 5.20~5.30 (5H, m), 3.81 (3H, s), 3.42, 3.59 (2H, ABq, J=19 Hz), 2.36 (3H, s), 1.61 (9H, s), 1.57 (9H, s).

IR ($CHCl_3$) ν $cm^{-1}$: 2980, 2250, 2154, 1769, 1716, 1634, 1543, 1245, 1149.

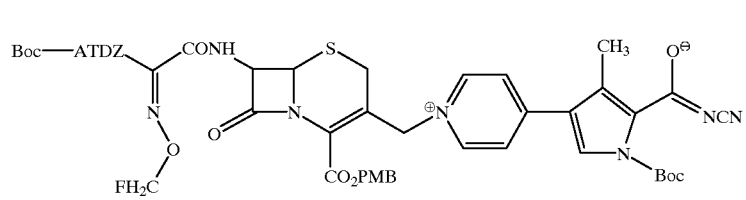

I-10'

Example 11

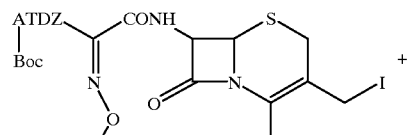

V-2

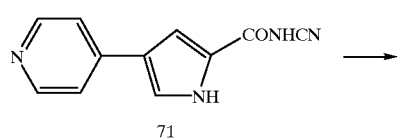

71

-continued

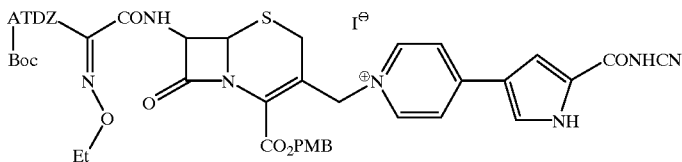

I-11

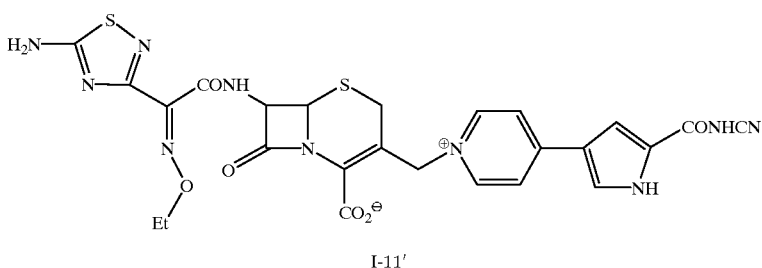

I-11'

(1) Compound 71 (500 mg, 2.36 mmol) was added to 20 ml of anhydrous DMSO, and V-2 (2.324 g, 3.06 mmol) was added thereto at room temperature under $N_2$ gas flow, and the mixture was stirred for 2 hours. The reaction solution was added dropwise to 500 ml of ethyl ether to obtain a precipitated oily product, which was dissolved in 8 ml of $CH_2Cl_2$. The $CH_2Cl_2$ solution was slowly added dropwise to 500 ml of stirred ethyl ether. The resultant precipitates were filtered off and dried to obtain 2.5 g of a yellow powder I-11.

Compound I-11: NMR ($d_6$-DMSO) δ: 12.65 (1H, bs), 12.60 (1H, bs), 9.70 (1H, d, J=8 Hz), 8.68 (2H, d, J=6 Hz), 8.18 (2H, d, J=7.5 Hz), 8.15 (1H, bs), 7.45 (1H, bs), 7.37 (2H, d, J=8.5 Hz), 6.84 (2H, d, J=8.5 Hz), 5.98 (1H, dd, J=10, 5 Hz), 5.12~5.43 (5H, m), 4.20 (2H, q, J=7.25 Hz), 3.73 (3H, s), 3.4~3.7 (2H, m), 1.50 (9H, s), 1.23 (3H, t, J=7.5 Hz).

IR ($CHCl_3$) ν $cm^{-1}$: 2986, 2250, 2150, 1772, 1715, 1633.

(2) In a manner similar to that described above, 68 mg of a pale yellow powder I-11' (yield 37%) was obtained from I-11 (290 mg, 0.3 mmol).

Compound I-11': NMR ($d_6$-DMSO) δ: 12.11 (1H, bs), 9.60 (1H, d, J=8.1 Hz), 8.67 (2H, d, J=6.9 Hz), 8.23 (2H, d, J=6.9 Hz), 8.14 (2H, s), 7.90 (1H, s), 7.21 (1H, s), 5.90 (1H, dd, J=9, 5.2 Hz), 5.38, 5.21 (2H, ABq, J=15.8 Hz), 5.19 (1H, d, J=5.1 Hz), 4.14 (2H, q, J=6.9 Hz), 3.52, 3.38 (2H, ABq, J=19.5 Hz), 1.21 (3H, t, J=7.05 Hz).

IR (KBr) ν $cm^{-1}$: 2989, 2257, 2155, 1775, 1674, 1636, 1569, 1335, 1162.

Example 12

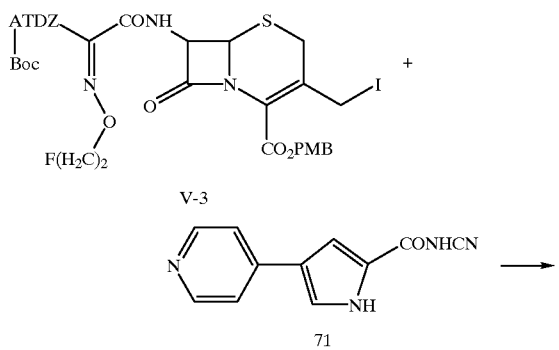

71

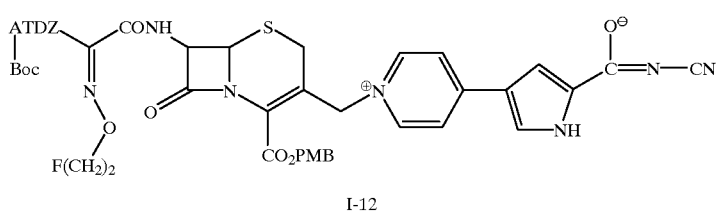

I-12

-continued

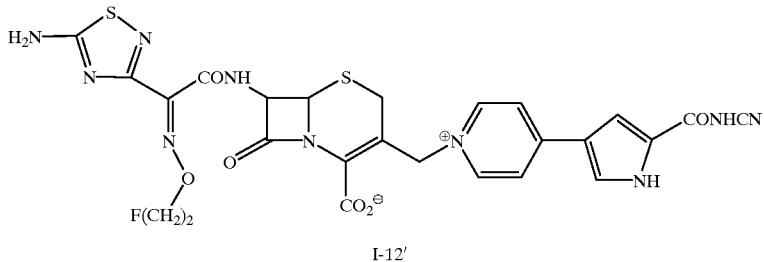

I-12'

(1) In a manner similar to that described above, 937 mg of a yellow powder I-12 (yield 95%) was obtained from V-3 (777 mg, 1 mmol) and 71 (212 mg, 1 mmol).

Compound I-12: NMR (d$_6$-DMSO) δ: 12.86 (1H, m), 12.64 (1H, m), 9.76 (1H, d, J=7.5 Hz), 8.70 (2H, d, J=7.5 Hz), 8.21 (1H, m), 8.19 (2H, d, J=6 Hz), 7.56 (1H, s), 7.38 (2H, d, J=9 Hz), 6.92 (2H, d, J=9 Hz), 6.00 (1H, dd, J=9, 5 Hz), 5.10~5.50 (5H, m), 4.78 (1H, m), 4.54 (2H, m), 4.32 (1H, m), 3.72 (3H, s), 1.50 (9H, s).

IR (CHCl$_3$) ν cm$^{-1}$: 3012, 2400, 2250, 1771, 1715, 1686, 1549, 1246, 1151.

(2) In a manner similar to that described above, 117 mg of a pale yellow powder I-12' (yield 19%) was obtained from the raw material I-12 (930 mg, 0.94 mmol).

Compound I-12': NMR (d$_6$-DMSO) δ: 12.11 (1H, bs), 9.67 (1H, d, J=9 Hz), 8.68 (2H, d, J=6.6 Hz), 8.23 (2H, d, J=6.8 Hz), 8.16 (2H, s), 7.90 (1H, s), 7.21 (1H, s), 5.90 (1H, dd, J=9, 5 Hz), 5.38, 5.20 (2H, ABq, J=14.5 Hz), 5.19 (1H, d, J=5.0 Hz), 4.75 (1H, m), 4.51 (1H, m), 4.42 (1H, m), 4.27 (1H, m), 3.55, 3.26 (2H, ABq, J=19.5 Hz).

IR (KBr) ν cm$^{-1}$: 2256, 2154, 1776, 1676, 1636, 1569, 1334, 1161.

Example 13

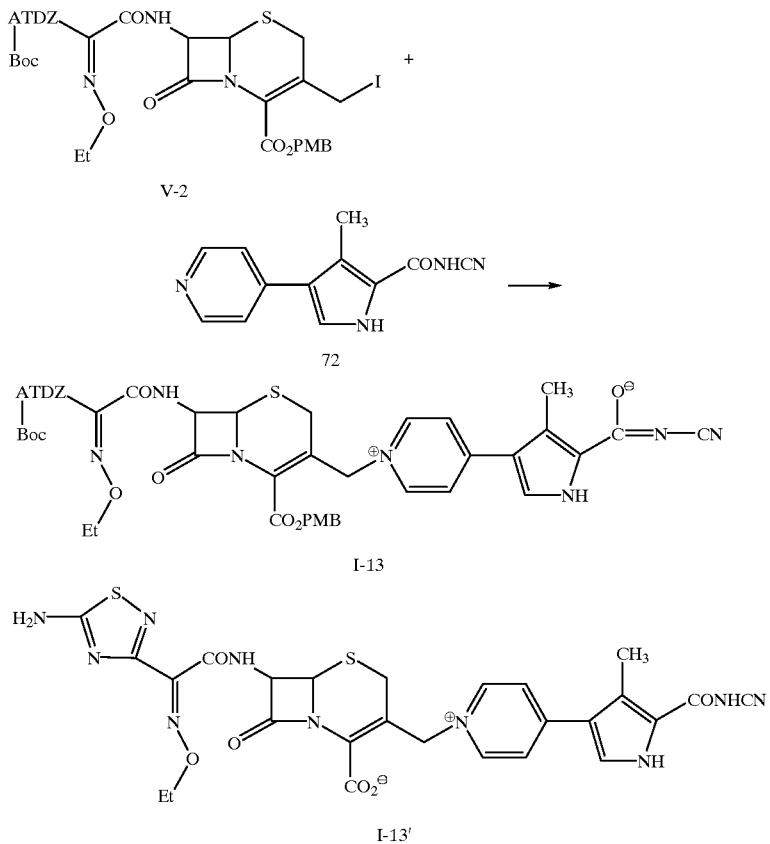

(1) In a manner similar to that described above, 1.57 g of a yellow powder I-13 was obtained from V-2 (910 mg, 1.2 mmol) and 72 (226 mg, 1 mmol).

Compound I-13: NMR (d$_6$-DMSO) δ: 12.61 (1H, m), 11.96 (1H, m), 9.71 (1H, d, J=9 Hz), 8.60 (2H, d, J=6.5 Hz), 8.20 (1H, m), 8.11 (2H, d, J=7 Hz), 7.78 (1H, s), 7.38 (2H, d, J=9.0 Hz), 6.96 (2H, d, J=9.0 Hz), 5.99 (1H, m), 5.10~5.56 (5H, m), 4.20 (2H, q, J=6.0 Hz), 3.73 (3H, s), 2.55 (3H, s), 3.40~3.62 (2H, m), 1.51 (9H, s), 1.23 (3H, t, J=7 Hz).

IR (CHCl₃) ν cm⁻¹: 2988, 2154, 1772, 1715, 1540, 1245, 1220.

(2) In a manner similar to that described above, 21 mg of a pale yellow powder I-13' (yield 3.3%) was obtained from I-13 (985 mg, 1 mmol).

Compound I-13': NMR (d₆-DMSO) δ: 11.83 (1H, bs), 9.59 (1H, d, J=9 Hz), 8.71 (2H, d, J=6.5 Hz), 8.14 (4H, m), 7.69 (1H, d, J=3.0 Hz), 5.88 (1H, dd, J=8.2, 5.1 Hz), 5.43, 5.19 (2H, ABq, J=13.6 Hz), 5.18 (1H, d, J=5.0 Hz), 4.15 (2H, q, J=6.3 Hz), 3.57, 3.29 (2H, ABq, J=19 Hz), 2.64 (3H, s), 1.21 (3H, t, J=6.9 Hz).

IR (KBr) ν cm⁻¹: 2253, 2155, 1779, 1634, 1563, 1391, 1156.

Example 14

6.38 (1H, d, J=15 Hz), 5.99 (1H, dd, J=9.8, 5 Hz), 5.43 (2H, ABq, J=15.8 Hz), 5.24 (3H, d, J=5.1 Hz), 4.20 (2H, q, J=7.2 Hz), 3.73 (3H, s), 3.38, 3.58 (2H, ABq, J=9.8 Hz), 1.50 (9H, s), 1.24 (3H, t, J=7.05 Hz).

IR (CHCl₃) ν cm⁻¹: 2988, 2362, 1774, 1716, 1601, 1540, 1243.

(2) In a manner similar to that described above, 536 mg of a pale yellow powder I-14' (yield 40%) was obtained from the raw material I-14 (2.256 g, 2.07 mmol).

Compound I-14': NMR (d₆-DMSO) δ: 12.06 (1H, bs), 9.60 (1H, d, J=9 Hz), 8.89 (2H, d, J=6.6 Hz), 8.03 (2H, d, J=6.9 Hz), 7.71 (1H, s), 7.57 (1H, d, J=15.3 Hz), 7.48 (1H,

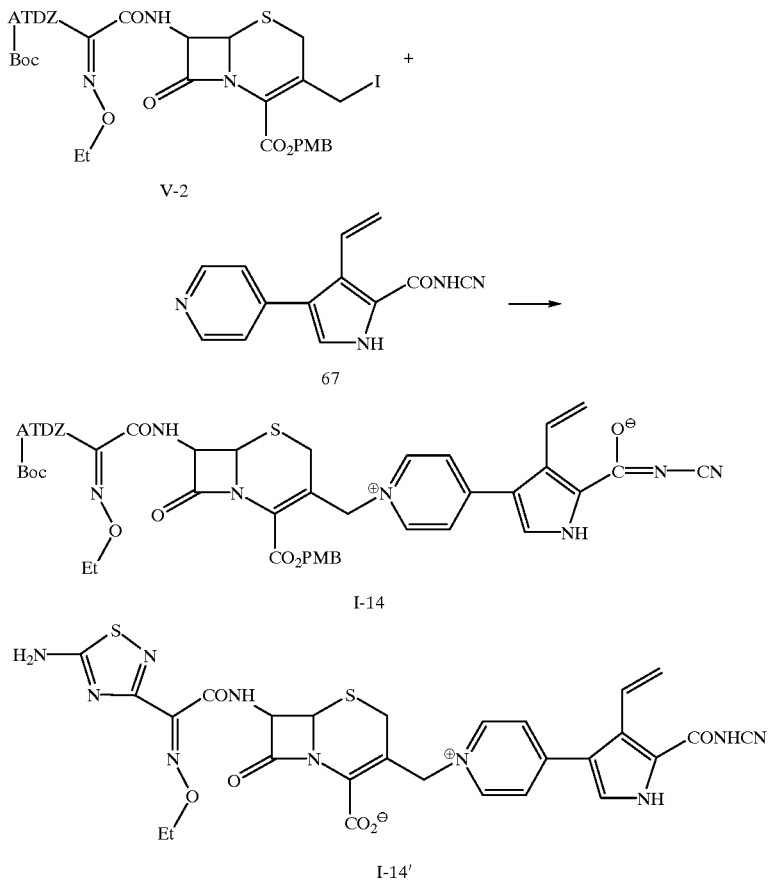

(1) In a manner similar to that described above, 2.27 g of a yellow powder I-14 was obtained from V-2 (1.89 g, 2.48 mmol) and 67 (506 mg, 2.07 mmol).

Compound I-14: NMR (d₆-DMSO) δ: 12.61 (1H, s), 12.27 (1H, s), 9.71 (1H, d, J=9 Hz), 8.78 (2H, d, J=6.9 Hz), 8.05 (2H, d, J=6.9 Hz), 7.83 (1H, s), 7.79 (1H, s), 7.71 (1H, d, J=16.5 Hz), 7.36 (2H, d, J=9 Hz), 6.92 (2H, d, J=8.4 Hz), s), 6.25 (1H, d, J=15.6 Hz), 5.83 (1H, dd, J=8.3, 6 Hz), 5.44, 5.23 (2H, ABq, J=15 Hz), 5.18 (1H, d, J=6 Hz), 4.14 (2H, q, J=6.9 Hz), 3.60, 3.37 (2H, ABq, J=18 Hz), 1.22 (3H, d, J=7.05 Hz).

IR (KBr) ν cm⁻¹: 2980, 2242, 2156, 1774, 1671, 1634, 1539, 1391, 1169.

Example 15

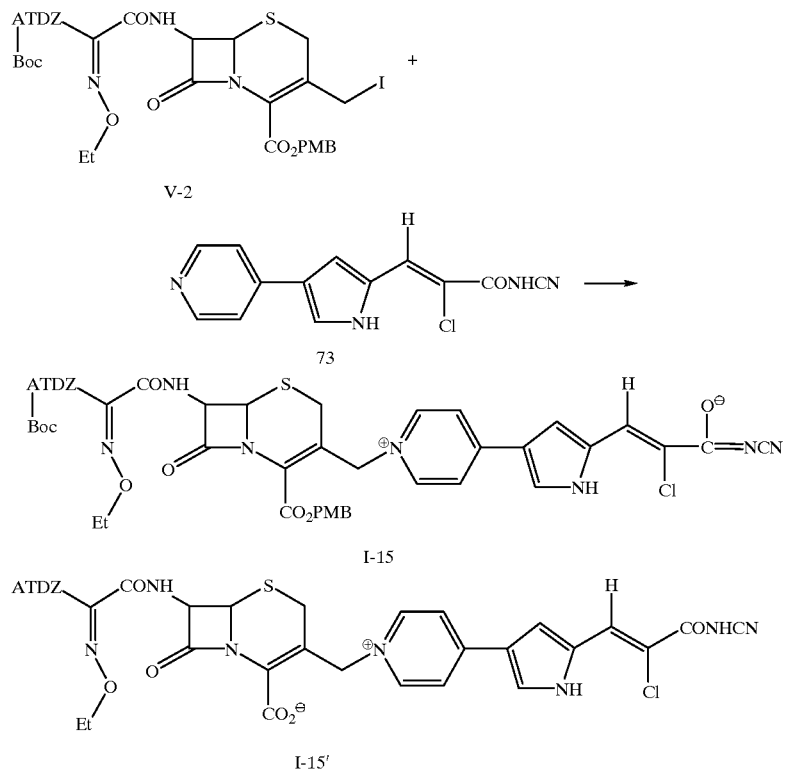

(1) In a manner similar to that described above, 1.12 g of a yellowish brown powder I-15 was obtained from V-2 (911 mg, 1.2 mmol) and 73 (273 mg, 1 mmol).

Compound I-15: NMR (d$_6$-DMSO) δ: 12.60 (1H, m), 12.31 (1H, m), 9.70 (1H, d, J=9 Hz), 8.66 (2H, d, J=7.0 Hz), 8.29 (1H, s), 8.22 (2H, d, J=8.5 Hz), 7.79 (1H, s), 7.61 (1H, s), 7.38 (2H, d, J=9 Hz), 6.95 (2H, d, J=9.1 Hz), 5.99 (1H, dd, J=9.5 Hz), 5.40 (2H, m), 5.24 (3H, m), 4.20 (2H, q, J=7.5 Hz), 3.73 (3H, s), 3.30~3.60 (2H, m), 1.50 (9H, s), 1.23 (3H, t, J=7.5 Hz).

IR (Nujol) ν cm$^{-1}$: 2978, 2158, 1772, 1716, 1542, 1369, 1245.

(2) In a manner similar to that described above, 282 mg of a yellow powder I-15' (yield 41%) was obtained from I-15 (1.1 g, 1.0 mmol).

Compound I-15': NMR (d$_6$-DMSO) δ: 12.22 (1H, bs), 9.60 (1H, d, J=9.0 Hz), 8.79 (2H, d, J=6.8 Hz), 8.14 (3H, s), 7.74 (1H, s), 7.55 (1H, s), 5.87 (1H, dd, J=8.5, 5 Hz), 5.41, 5.23 (2H, ABq, J=15 Hz), 5.18 (1H, d, J=5.0 Hz), 4.14 (2H, q, J=7.0 Hz), 3.36~3.60 (2H, m), 1.21 (3H, t, J=7.1 Hz).

IR (KBr) ν cm$^{-1}$: 2984, 2257, 2157, 1775, 1671, 1623, 1564, 1348, 1155.

Example 16

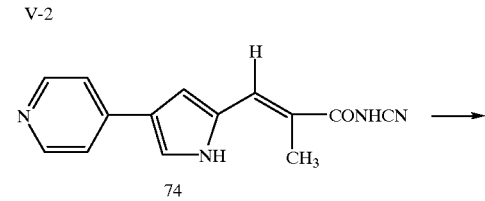

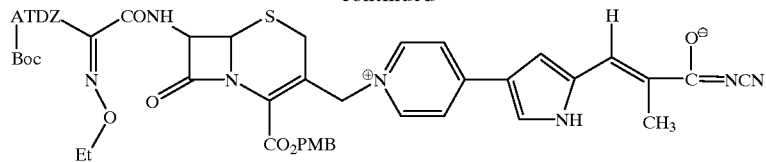

I-16

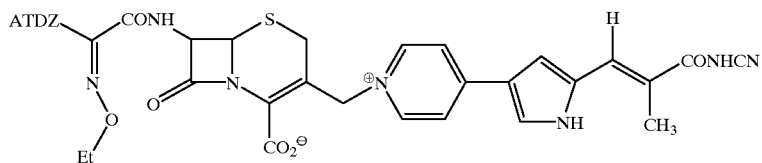

I-16'

(1) In a manner similar to that described above, 2.26 g of a yellow powder I-16 was obtained from V-2 (1.82 g, 2.4 mmol) and 74 (5.0 mg, 2 mmol).

Compound I-16: NMR (d$_6$-DMSO) δ: 12.61 (1H, s), 12.30 (1H, s), 9.70 (1H, d, J=9 Hz), 8.68 (2H, d, J=6.6 Hz), 8.29 (2H, d, J=6.9 Hz), 8.13 (1H, s), 7.37 (2H, d, J=8.7 Hz), 7.31 (1H, s), 6.92 (2H, d, J=8.4 Hz), 5.99 (1H, dd, J=9.5 Hz), 5.39 (2H, brs), 5.24 (3H, m), 4.20 (2H, q, J=7.2 Hz), 3.73 (3H, s), 3.51 (2H, ABq, J=19.5 Hz), 2.15 (3H, s), 1.50 (9H, s), 1.23 (3H, t, J=7.2 Hz).

IR (CHCl$_3$) ν cm$^{-1}$: 2990, 2234, 2144, 1771, 1716, 1682, 1629, 1245, 1543.

(2) In a manner similar to that described above, 476 mg of a yellow powder I-16' (yield 36%) was obtained from I-16 (2.02 g, 2 mmol).

Compound I-16': NMR (d$_6$-DMSO) δ: 12.10 (1H, bs), 9.62 (1H, d, J=9 Hz), 8.73 (2H, d, J=6.9 Hz), 8.24 (2H, d, J=7.2 Hz), 8.12 (2H, s), 8.08 (1H, d, J=1.2 Hz), 7.36 (1H, s), 7.11 (1H, s), 5.86 (1H, dd, J=9.8, 5.1 Hz), 5.41, 5.20 (2H, ABq, J=14 Hz), 5.18 (1H, d, J=4.8 Hz), 4.15 (2H, q, J=6.9 Hz), 3.58, 3.33 (2H, ABq, J=18 Hz), 2.09 (3H, s), 1.22 (3H, t, J=7.2 Hz).

IR (KBr) ν cm$^{-1}$: 2987, 2243, 2150, 1775, 1672, 1631, 1530, 1355, 1152.

I-16'

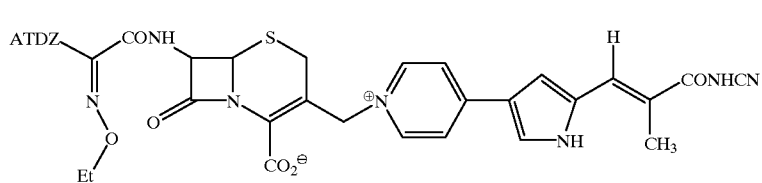

Example 17

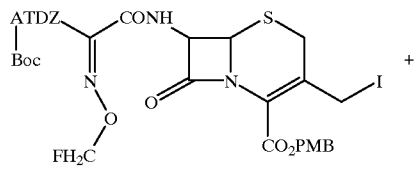

V-1

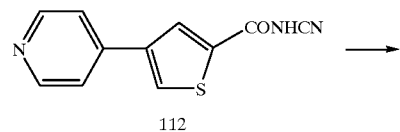

112

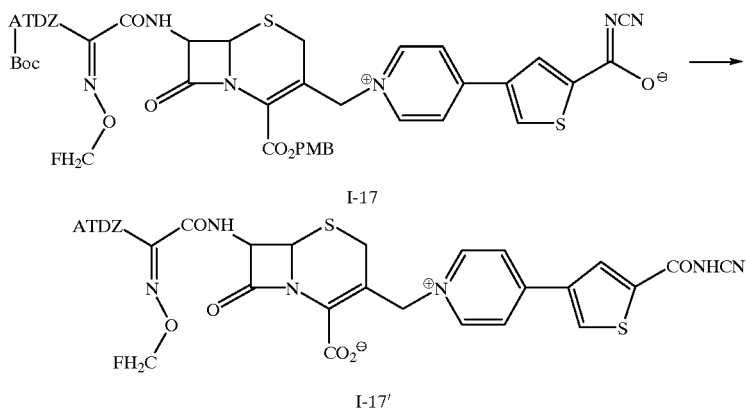

I-17

I-17'

(1) To a suspension of 112 (229 mg, 1 mmol) in 7 ml of anhydrous DMSO was added and V-1 (957 mg, 1.2 mmol) was added at room temperature under N₂ gas flow, and the mixture was stirred at room temperature for 100 minutes. The insoluble materials were removed by filtration and the filtrate was added dropwise to a 5% saline solution. The precipitated solids were collected by filtration, washed with a 5% saline solution, and dissolved in acetonitrile/CHCl₃ (3/1). The organic layer was taken and dried over MgSO₄. After MgSO₄ was removed by filtration, the filtrate was concentrated under reduced pressure. The residue was then poured into 100 ml of ethyl acetate. The precipitated solids were collected by filtration, and dried to obtain 344 mg of a yellow powder I-17 (yield 40%).

Compound I-17: NMR (d₆-DMSO) δ: 12.69 (1H, bs), 9.90 (1H, d, J=8.2 Hz), 8.85 (2H, d, J=7 Hz), 8.71 (1H, s), 8.49 (2H, d, J=7 Hz), 8.24 (3H, s), 7.37 (2H, d, J=8 Hz), 6.90 (2H, d, J=8 Hz), 5.99 (1H, dd, J=8.2, 4.8 Hz), 5.94 (1H, s), 5.67 (1H, bs), 5.47 (2H, bs), 5.14–5.26 (3H, m), 3.72 (3H, s), 3.40–3.70 (2H, m), 1.51 (9H, s).

IR (KBr) ν cm⁻¹: 2970, 2166, 1787, 1712, 1632, 1539, 1245, 1151, 855.

(2) In a manner similar to that described above, 25 mg of a yellowish white powder I-17' (yield 10%) was obtained from I-17 (335 mg, 0.388 mmol).

Compound I-17': NMR (d₆-DMSO) δ: 9.79 (1H, d, J=8.1 Hz), 8.98 (2H, d, J=6.6 Hz), 8.66 (1H, d, J=1.8 Hz), 8.53 (2H, d, J=6.9 Hz), 8.19 (3H, s), 5.89 (1H, dd, J=8.0, 5.3 Hz), 5.84 (1H, s), 5.66 (1H, s), 5.51, 5.32 (2H, ABq, J=14.6 Hz), 5.20 (1H, d, J=5.1 Hz), 3.56, 3.37 (2H, ABq, J=18.3 Hz).

IR (KBr) ν cm⁻¹: 2170, 1777, 1675, 1633, 1538, 1349, 1154, 1062, 989.

Example 18

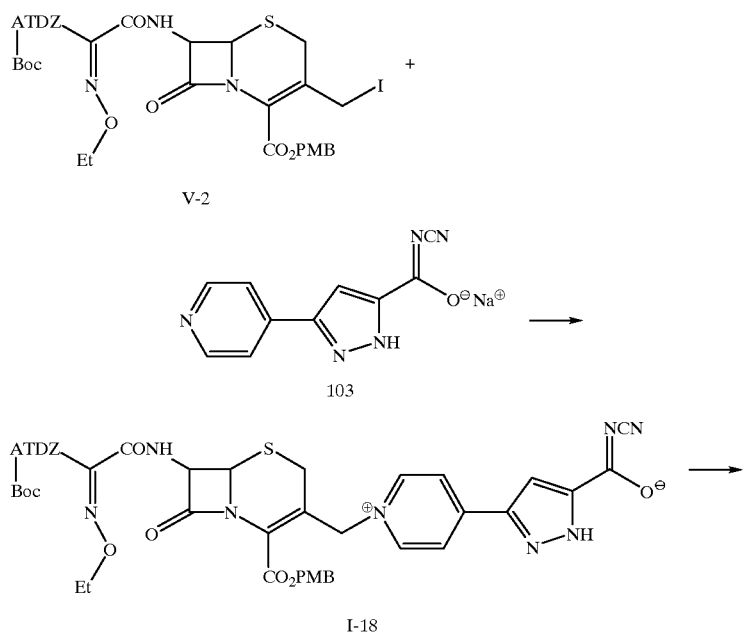

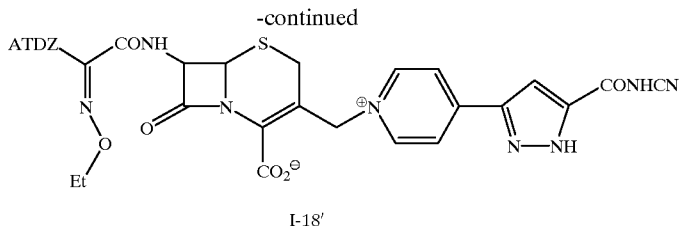

I-18′

(1) In a manner similar to that described above, 1.462 g of a yellow powder I-18 (yield 96%) was obtained from V-2 (1.749 g, 1.844 mmol) and 103 (413 mg, 1.756 mmol).

Compound I-18: NMR ($d_6$-DMSO) δ: 14.11 (1H, bs), 12.60 (1H, bs), 9.70 (1H, d, J=8.4 Hz), 8.85 (2H, d, J=6.8 Hz), 8.47 (2H, d, J=6.8 Hz), 7.49 (1H, s), 7.35 (2H, d, J=8.6 Hz), 6.91 (2H, d, J=8.6 Hz), 5.99 (1H, dd, J=8.6, 5.0 Hz), 5.43, 5.51 (2H, ABq, J=16.5 Hz), 5.16–5.33 (3H, m), 4.19 (2H, q, J=7.0 Hz), 3.72 (3H, s), 3.60, 3.47 (2H, ABq, J=19 Hz), 1.50 (9H, s), 1.23 (3H, t, J=7.2 Hz).

IR (KBr) ν $cm^{-1}$: 2970, 2154, 1789, 1713, 1636, 1538, 1341, 1245, 1151, 1034.

(2) In a manner similar to that described above, 330 mg of a white powder I-18′ (yield 32%) was obtained from I-18 (1.452 g, 1.677 mmol).

Compound I-18: NMR ($d_6$-DMSO) δ: 14.09 (1H, bs), 9.60 (1H, d, J=8.4 Hz), 8.92 (2H, d, J=6.9 Hz), 8.51 (2H, d, J=6.9 Hz), 8.12 (2H, s), 7.47 (1H, s), 5.91 (1H, dd, J=8.4, 4.8 Hz), 5.52, 5.38 (2H, ABq, J=14.9 Hz), 5.19 (1H, d, J=5.1 Hz), 4.14 (2H, q, J=7.2 Hz), 3.56, 3.41 (2H, ABq, J=19.5 Hz), 1.21 (3H, t, J=7.05 Hz).

IR (KBr) ν $cm^{-1}$: 2970, 2158, 1774, 1671, 1636, 1526, 1403, 1345, 1154, 1036.

Example 19

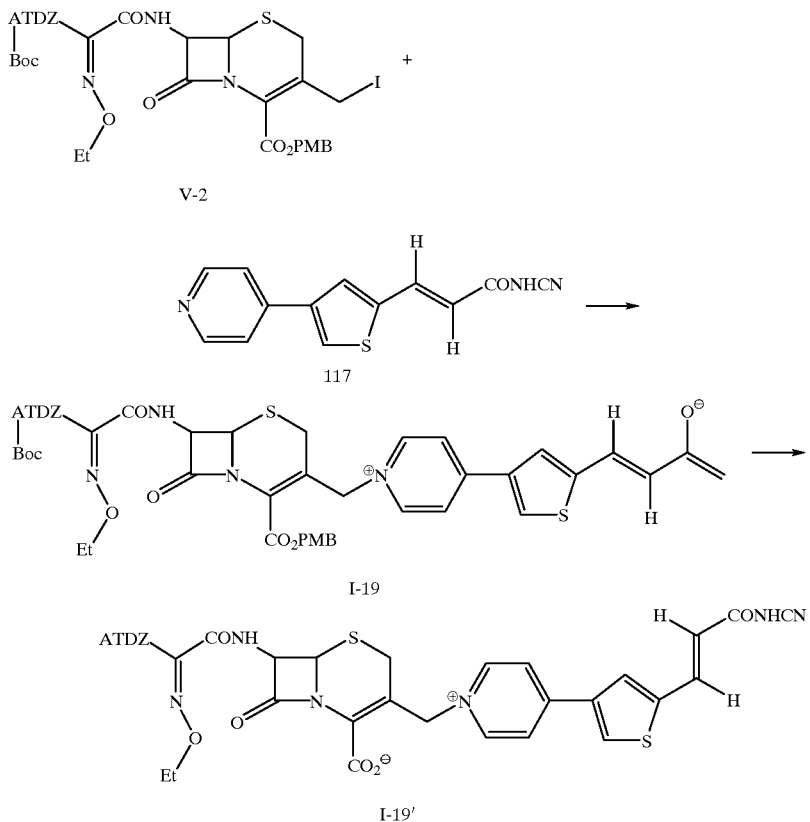

(1) To a suspension of 117 (306 mg, 1.2 mmol) in 6 ml of anhydrous DMSO was added dropwise N,O-bis(trimethylsilyl)-acetamide (292 μl, 1.2 mmol) under $N_2$ gas flow with stirring. After adding V-2 (1.195 g, 1.26 mmol), the mixture was stirred at room temperature for 85 minutes. The reaction solution was then added dropwise to 65 ml of a 5% saturated saline solution. The precipitated solids were collected by filtration and washed with $H_2O$. The yellow solids were dissolved in acetonitrile/$CHCl_3$ (80 ml/30 ml) and the solution was dried over $MgSO_4$. After $MgSO_4$ was removed by filtration, the filtrate was concentrated under reduced pressure. The residue was poured into 50 ml of ethyl acetate, and 100 ml of ethyl ether was further added. The precipitated solids were collected by filtration, and dried to obtain 840 mg of a yellow powder I-19 (yield 79%).

Compound I-19: NMR (d$_6$-DMSO) δ: 12.60 (1H, bs), 9.69 (1H, d, J=8.4 Hz), 8.91 (2H, d, J=7.2 Hz), 8.78 (1H, s), 8.44 (2H, d, J=6.9 Hz), 8.19 (1H, s), 7.63 (1H, d, J=15.6 Hz), 7.35 (2H, d, J=8.7 Hz), 6.91 (2H, d, J=8.7 Hz), 6.39 (1H, d, J=15.6 Hz), 5.99 (1H, dd, J=8.6 Hz, 5.0 Hz), 5.53, 5.46 (2H, ABq, J=13.5 Hz), 5.17–5.26 (3H, m), 4.20 (2H, q, J=7.2 Hz), 3.72 (3H, s), 3.54, 3.59 (2H, ABq, J=17.3 Hz), 1.50 (9H, s), 1.23 (3H, t, J=7 Hz).

IR (KBr) ν cm$^{-1}$: 2970, 2228, 2148, 1788, 1713, 1630, 1537, 1514, 1369, 1245, 1153, 1033.

(2) In a manner similar to that described above, 232 mg of a yellowish white powder I-19' (yield 37%) was obtained from I-19 (831 mg, 0.94 mmol).

Compound I-19': NMR (d$_6$-DMSO, D$_2$O) δ: 9.62 (1H, d, J=7.5 Hz), 9.00 (2H, d, J=6.0 Hz), 8.70 (1H, s), 8.44 (2H, d, J=4.8 Hz), 8.12 (1H, s), 7.58 (1H, d, J=15.3 Hz), 6.35 (1H, d, J=15.2 Hz), 5.87 (1H, d, J=6 Hz), 5.54, 5.33 (2H, ABq, J=15 Hz), 5.17 (1H, d, J=6 Hz), 4.13 (2H, q, J=7.5 Hz), 3.77, 3.37 (2H, ABq, J=18 Hz), 1.22 (3H, t, J=6.8 Hz).

IR (KBr) ν cm$^{-1}$: 2257, 2158, 1776, 1674, 1623, 1536, 1357, 1156, 1038.

Example 20

(1) In a manner similar to that described above, 393 mg of a yellow powder I-20 (quantitative) was obtained from 96 (E) (123 mg, 0.488 mmol) and V-2 (458 mg, 0.58 mmol).

Compound I-20: NMR (d$_6$-DMSO) δ: 12.60 (1H, bs), 12.49 (1H, bs), 9.69 (1H, d, J=8.1 Hz), 8.68 (2H, d, J=6.9 Hz), 8.24 (2H, d, J=6.6 Hz), 8.22 (1H, s), 7.41 (1H, s), 7.35 (2H, d, J=8.7 Hz), 6.92 (2H, d, J=8.7 Hz), 6.27 (1H, d, J=0.6 Hz), 5.99 (1H, dd, J=8.25, 4.95 Hz), 5.41, 5.38 (2H, ABq, J=9 Hz), 5.16–5.25 (3H, m), 4.20 (2H, q, J=7.2 Hz), 3.73 (3H, s), 3.57, 3.49 (2H, ABq, J=17.3 Hz), 1.50 (9H, s), 1.24 (3H, t, J=7.05 Hz).

IR (KBr) ν cm$^{-1}$: 2972, 2230, 2144, 1786, 1711, 1633, 1610, 1543, 1245, 1153, 1033, 931.

(2) In a manner similar to that described above, 75 mg of a yellowish green powder I-20' (yield 26%) was obtained from I-2 (382 mg, 0.43 mmol).

Compound I-20': NMR (d$_6$-DMSO) δ: 12.26 (1H, bs), 9.55 (1H, d, J=7.8 Hz), 8.84 (2H, d, J=6 Hz), 8.21 (2H, d, J=6 Hz), 8.13 (2H, s), 8.08 (1H, s), 7.25 (1H, s), 6.31 (1H, s), 5.84 (1H, dd, J=9, 5.4 Hz), 5.39, 5.16 (2H, ABq, J=14 Hz), 5.14 (1H, d, J=5.4 Hz), 4.14 (2H, q, J=6.3 Hz), 3.58, 3.26 (2H, ABq, J=20 Hz), 2.50 (3H, s), 1.21 (3H, t, J=6.9 Hz).

IR (KBr) ν cm$^{-1}$: 2238, 2147, 1775, 1676, 1635, 1605, 1525, 1353, 1154, 1037, 933.

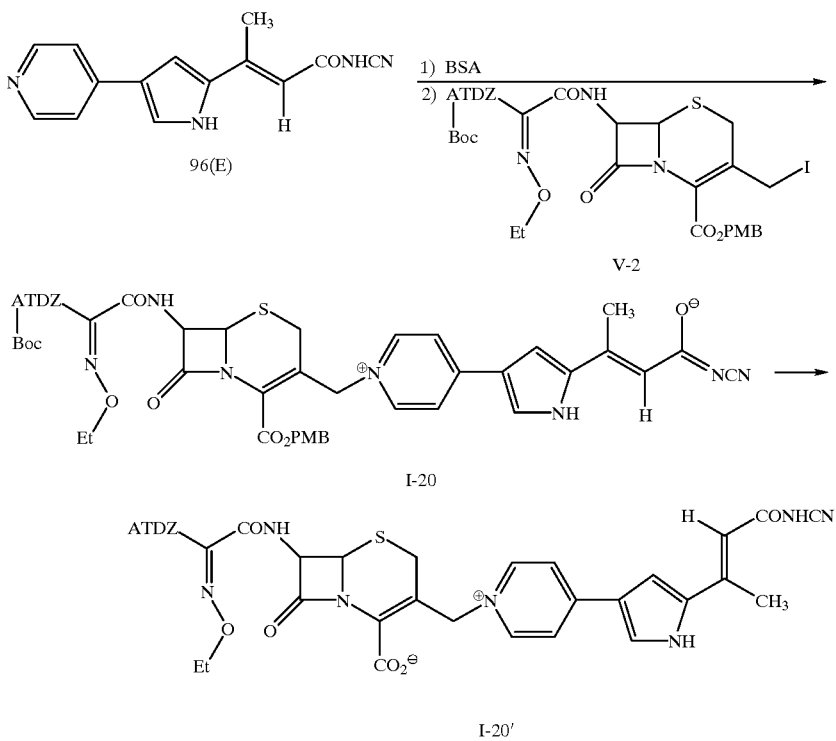

Example 21

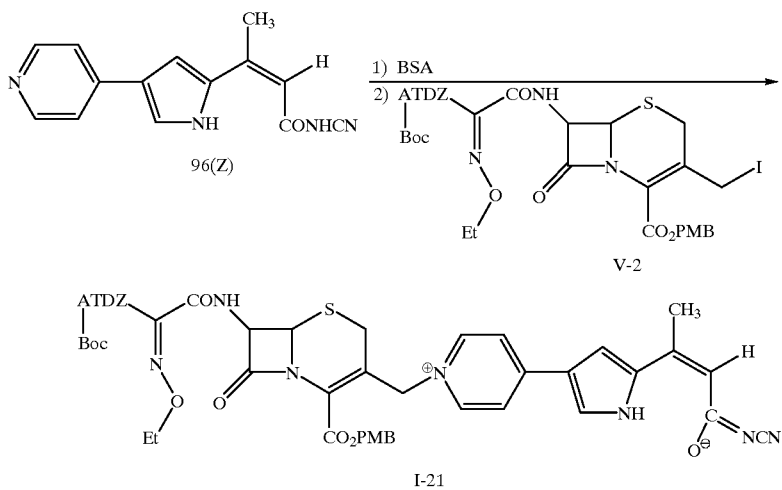

In a manner similar to that described above, 485 mg (99%) of a yellowish brown powder I-21 was obtained from 96 (Z) (162 mg, 0.642 mmol) and V-2 (552 mg, 0.706 mmol).

Compound I-21: NMR ($d_6$-DMSO) δ: 12.60 (1H, bs), 12.42 (1H, bs), 9.69 (1H, d, J=8.1 Hz), 8.65 (2H, d, J=6.6 Hz), 8.22 (2H, dd, J=6.6, 0.6 Hz), 8.16 (1H, d, J=3.0 Hz), 7.36 (2H, d, J=8.4 Hz), 7.33 (1H, d, J=3.0 Hz), 6.92 (2H, d, J=8.4 Hz), 5.98 (1H, dd, J=8.9, 4.5 Hz), 5.71 (1H, s), 5.39, 5.37 (2H, ABq, J=8 Hz), 5.13–5.26 (3H, m), 4.20 (2H, q, J=6.9 Hz), 3.73 (3H, s), 3.48, 3.56 (2H, ABq, J=18.8 Hz), 2.24 (3H, s), 1.50 (9H, s), 1.23 (3H, t, J=7.2 Hz).

IR (KBr) ν $cm^{-1}$: 2970, 2240, 2144, 1787, 1712, 1632, 1546, 1514, 1246, 1154, 1033, 932.

Test 1

The minimal inhibitory concentration (MIC) was determined by an agar dilution method. That is, 1.0 ml each of an aqueous solution of a test compound diluted in series was poured into a petri dish. Trypticase soy agar (9 ml) was poured into the solution, and mixed. A suspension (about $10^6$ CFU/ml) of test bacteria was smeared on the mixed agar plate. After culturing at 37° C. overnight, the minimum concentration of the test compound required to completely inhibit the growth of the test bacteria was taken as MIC.

Test Bacteria:

Gram-positive bacteria; S. pyogenes C-203, S. agalactiae ATCC13813, S. pneumoniae Type I, S. pneumoniae SR16675 (PC-R), S. mitis ATCC9811 Gram-negative bacteria: K. pneumoniae SR1, P. mirabilis PR-4 and P. vulgaris CN-329.

Results:

TABLE 1

| Inoculation amount: | MIC(μg/ml) | | | |
|---|---|---|---|---|
| | Compound of the present invention | | | |
| $10^6$ CFU/ml | I-1' | I-9" | Control compound | |
| Test bacteria | (Example 1) | (Example 9) | (1) | (2) |
| Gram-positive bacteria | | | | |
| S. pyogenes C-203 | 0.006 | 0.006 | 0.013 | 0.006 |
| S. agalactiae ATCC13813 | 0.025 | 0.013 | 0.1 | 0.025 |
| S. pneumoniae Type I | 0.013 | 0.006 | 0.05 | 0.006 |
| S. pneumoniae SR16675 (PC-R) | 0.2 | 0.2 | 0.78 | 0.39 |
| S. mitis ATCC9811 | 0.05 | 0.025 | 0.1 | 0.025 |
| Gram-negative bacteria | | | | |
| K. pneumoniae R1 | 0.006 | 0.006 | 0.05 | 0.013 |
| P. mirabilis PR-4 | 0.013 | 0.013 | 0.1 | 0.05 |
| P. vulgaris CN-329 | 0.013 | 0.013 | 0.1 | 0.025 |

(Control compound)

(1)

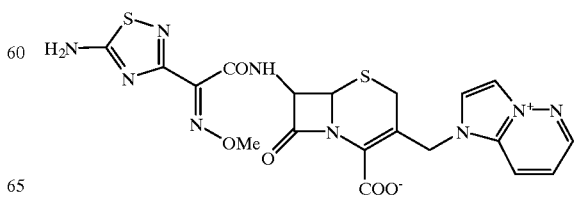

TABLE 1-continued

| | MIC(μg/ml) | | |
|---|---|---|---|
| Inoculation amount: | Compound of the present invention | | |
| $10^6$ CFU/ml | I-1' | I-9" | Control compound |
| Test bacteria | (Example 1) | (Example 9) | (1) (2) |

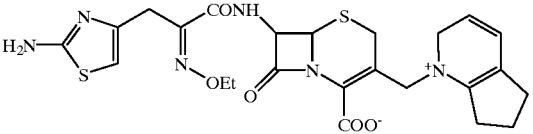

(2)

As is apparent from Table 1, the compound of the present invention exerts excellent and well-balanced antibacterial activity to typical strains of pathogenic bacteria, which are considered important from clinical point of view.

Test 2

The blood half-life and the treating effect on infections in mouse were examined by using the compound I-9" and control compound (1) as used in Test 1 above.

The results are shown in Table 2 and Table 3.

TABLE 2

| | Half-life in Blood (h) | |
|---|---|---|
| | I-9" | Control compound (1) |
| Mouse | 0.96 | 0.39 |
| Monkey | 2.48 | 1.28 |

For the exertion of antibacterial activity to Pseudomonas, it is necessary that a drug contacts with bacteria for a long-term. Accordingly, the longer the blood half-life ($T_{1/2}$), the more advantageous. The above results show that the compound of the present invention is effective on infectious diseases caused by Pseudomonas.

TABLE 3

| Treating Effect on Infections in Mouse, $ED_{50}$ (mg/kg) | | |
|---|---|---|
| | I-9" | Control compound (1) |
| S. aureus Smith | 0.41 | 0.76 |
| S. pneumoniae Type I | 0.042 | 0.69 |
| P. vulgaris GN-329 | 0.009 | 0.61 |
| P. aeruginosa SR24 | 0.38 | 1.52 |
| P. aeruginosa E-2 | 0.79 | 4.73 |

The above results show that the compound of the present invention is effective in vivo.

What we claim is:

1. A cephem compound shown by the formula I:

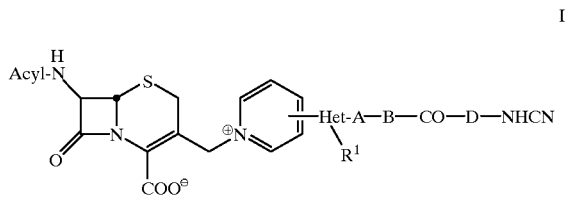

I wherein

Acyl is selected from the group consisting of formyl, ($C_1$–$C_6$) alkylcarbonyl, ($C_3$–$C_5$) alkenoyl, ($C_3$–$C_{10}$) cycloalkyl-carbonyl, ($C_5$–$C_6$)cycloalkenyl-carbonyl, arylcarbonyl, aralkyl carbonyl, 5- or 6-membered aromatic heterocyclic carbonyl, 5- or 6-membered aromatic heterocyclic acetyl, alkoxycarbonyl, aryloxycarbonyl, aralkyloxycarbonyl, aminoalkylcarbonyl, monoalkylaminoalkylcarbonyl, and dialkylaminoalkylcarbonyl, optionally substituted with one to three substituents independently selected from the group consisting of amino, nitro, halogen, hydroxy, oxo, carbamoyl, ($C_1$–$C_4$) alkyl, ($C_1$–$C_4$) alkoxy, ($C_1$–$C_4$) alkoxycarbonyl, ($C_1$–$C_4$) alkoxyimino optionally substituted with carboxyl or halogen, hydroxyimino and 4-ethyl-2,3-dioxopiperadinocarbonylamino, or acyl is represented by formula III:

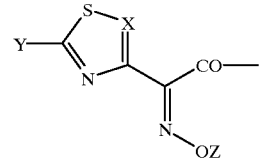

III wherein X is CH or N; Y is an optionally protected amino; and Z is hydrogen or an optionally substituted hydrocarbon group;

Het is a mono- or polycyclic heterocyclic group comprising one or more hetero atoms selected from the group consisting of N, O and S which may be the same or different from each other; $R^1$ is hydrogen, a straight or branched lower alkyl which is optionally substituted with 1 to 3 substituents independently selected from the group consisting of $C_{2-6}$ alkenyl, cycloalkyl, aryl which is optionally substituted with hydroxy, $C_{1-4}$ alkyl, or $C_{1-4}$ alkoxy, an aromatic heterocyclic group comprising 1 to 4 hetero atoms selected from the group consisting of N, O, and S, a bi- or tricyclic aromatic condensed heterocyclic group comprising 1 to 5 hetero atoms selected from the group consisting of N, O, and S, which is formed by condensing one or two 5- or 6-membered-aromatic heterocyclic groups comprising 1 to 4 hetero atoms selected from N, O, and S, a non-aromatic heterocyclic group, amino, mono- or di-alkyl amino, amidino, $C_{1-6}$ alkanoyl, carbamoyl, mono- or di-lower alkylcarbamoyl, sulfamoyl, mono- or di-lower alkyl sulfamoyl, carboxyl, lower alkoxycarbonyl, hydroxyl, lower alkoxy, lower alkenyloxy, cycloalkyloxy, aralkyloxy, aryloxy, mercapto, lower alkylthio, aralkylthio, arylthio, sulfo, cyano, azide, nitro, nitroso and halogen, or a straight or branched lower alkenyl which is optionally substituted with 1 to 3 substituents independently selected from the group consisting of $C_{2-6}$ alkenyl, cycloalkyl, aryl which is optionally substituted with hydroxy, $C_{1-4}$ alkyl, or $C_{1-4}$ alkoxy, an aromatic heterocyclic group comprising 1 to 4 hetero atoms selected from the group consisting of N, O, and S, a bi- or tricyclic aromatic condensed heterocyclic group comprising 1 to 5 hetero atoms selected from the group consisting of N, O, and S, which is formed by condensing one or two 5- or 6-membered aromatic heterocyclic groups comprising 1 to 4 hetero atoms selected from N, O, and S, a non-aromatic heterocyclic group, amino, mono- or di-alkyl amino, amidino, $C_{1-6}$ alkanoyl, carbamoyl, mono- or di-lower alkylcarbamoyl, sulfamoyl, mono- or di-lower alkyl sulfamoyl, carboxyl, lower alkoxycarbonyl, hydroxyl, lower alkoxy, lower alkenyloxy, cycloalkyloxy, aralkyloxy, aryloxy, mercapto, lower alkylthio, aralkylthio, arylthio, sulfo, cyano, azide, nitro, nitroso and halogen; A is a lower alkylene which is optionally substituted with 1 to 3 substituents independently selected from the group consisting of $C_{2-6}$ alkenyl, cycloalkyl, aryl which is optionally substituted with hydroxy, $C_{1-4}$ alkyl, or $C_{1-4}$ alkoxy, an aromatic heterocyclic group comprising 1 to 4 hetero atoms selected from the group consisting of N, O, and S, a bi- or tricyclic aromatic condensed heterocyclic group comprising 1 to 5 hetero atoms selected from the group consisting of N, O, and S, which is formed by condensing one or two 5- or 6-membered aromatic heterocyclic groups comprising 1 to 4 hetero atoms selected from N, O, and S, a non-aromatic heterocyclic group, amino, mono- or di-alkyl amino, amidino, $C_{1-6}$ alkanoyl, carbamoyl, mono- or di-lower alkylcarbamoyl, sulfamoyl, mono- or di-lower alkyl sulfamoyl, carboxyl, lower alkoxycarbonyl, hydroxyl, lower alkoxy, lower alkenyloxy, cycloalkyloxy, aralkyloxy, aryloxy, mercapto, lower alkylthio, aralkylthio, arylthio, sulfo, cyano, azide, nitro, nitroso and halogen, a lower alkenylene which is optionally substituted with 1 to 3 substituents independently selected from the group consisting of $C_{2-6}$ alkenyl, cycloalkyl, aryl which is optionally substituted with hydroxy, $C_{1-4}$ alkyl, or $C_{1-4}$ alkoxy, an aromatic heterocyclic group comprising 1 to 4 hetero atoms selected from the group consisting of N, O, and S, a bi- or tricyclic aromatic condensed heterocyclic group comprising 1 to 5 hetero atoms selected from the group consisting of N, O, and S, which is formed by condensing one or two 5- or 6-membered aromatic heterocyclic groups comprising 1 to 4 hetero atoms selected from N, O, and S, a non-aromatic heterocyclic group, amino, mono- or di-alkyl amino, amidino, $C_{1-6}$ alkanoyl, carbamoyl, mono- or di-lower alkylcarbamoyl, sulfamoyl, mono- or di-lower alkyl sulfamoyl, carboxyl, lower alkoxycarbonyl, hydroxyl, lower alkoxy, lower alkenyloxy, cycloalkyloxy, aralkyloxy, aryloxy, mercapto, lower alkylthio, aralkylthio, arylthio, sulfo, cyano, azide, nitro, nitroso and halogen or a single bond; B is —NH— or a single bond; and D is a single bond or a group of the formula:

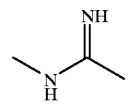

or an ester, a salt or a hydrate thereof.

2. A pharmaceutical composition comprising a compound of claim 1 in association with pharmaceutically acceptable carriers.

3. The compound of claim 1, wherein the Acyl is represented by the formula III:

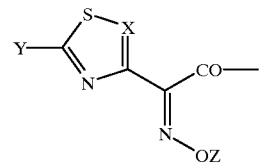

wherein X is CH or N; Y is an optionally protected amino; and Z is hydrogen or an optionally substituted hydrocarbon group.

4. The compound of claim 1, wherein Het is a 5- or 6-membered hetero cyclic group comprising one to four hetero atoms selected from the group consisting of N, O and S which may be the same or different from each other.

5. The compound of claim 1, wherein Het is a group of the formula IV:

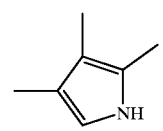

6. The compound of claim 1, wherein A is a single bond or a vinyl group; B is a single bond; and D is a single bond.

7. The compound of claim 1, wherein Acyl is a group of the formula III:

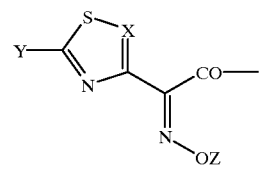

wherein X is CH or N, Y is an optionally protected amino and Z is hydrogen or an optionally substituted hydrocarbon group; Het is a 5- or 6-membered hetero cyclic group comprising one to four hetero atoms selected from the group consisting of N, O and S which may be the same or different from each other; A is a single bond or a vinyl group; B is a single bond; and D is a single bond.

* * * * *